(12) United States Patent
Reynolds

(10) Patent No.: US 11,661,610 B2
(45) Date of Patent: *May 30, 2023

(54) INSECTICIDAL PROTEINS

(71) Applicant: Syngenta Participations AG, Basel (CH)

(72) Inventor: Clarence Michael Reynolds, Research Triangle Park, NC (US)

(73) Assignee: Syngenta Participations SG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/468,905

(22) Filed: Sep. 8, 2021

(65) Prior Publication Data

US 2021/0403938 A1 Dec. 30, 2021

Related U.S. Application Data

(63) Continuation of application No. 16/322,162, filed as application No. PCT/US2017/045256 on Aug. 3, 2017, now Pat. No. 11,136,593.

(60) Provisional application No. 62/372,375, filed on Aug. 9, 2016.

(51) Int. Cl.
*C12N 15/82* (2006.01)
*C07K 14/195* (2006.01)
*A01N 63/50* (2020.01)
*C07K 14/20* (2006.01)
*A01N 63/20* (2020.01)

(52) U.S. Cl.
CPC ........ *C12N 15/8286* (2013.01); *A01N 63/20* (2020.01); *A01N 63/50* (2020.01); *C07K 14/195* (2013.01); *C07K 14/20* (2013.01)

(58) Field of Classification Search
None
See application file for complete search history.

(56) References Cited

U.S. PATENT DOCUMENTS

| 9,061,059 | B2 | 6/2015 | Chakraborty et al. |
| 10,023,877 | B2 | 7/2018 | Cong et al. |
| 2010/0064386 | A1 | 3/2010 | Park et al. |
| 2014/0274885 | A1 | 9/2014 | Cong et al. |
| 2015/0020236 | A1 | 1/2015 | Lee et al. |

FOREIGN PATENT DOCUMENTS

| BR | PI0804546 A2 | 7/2010 |
| WO | 2014150914 A1 | 9/2014 |
| WO | 2016033265 A1 | 3/2016 |

OTHER PUBLICATIONS

UniProtKB F7KHG1_9FIRM (2011, https://www.uniprot.org/uniprotkb/F7KHG1/entry).*
Amir et al., International Journal of Systematic and Evolutionary Microbiology. Mar. 2014, Epub Nov. 26, 2013, vol. 64, No. 3, Genbank Supplement, pp. 1-2.
International Search Report dated Dec. 15, 2017 in International Application No. PCT/US2017/045256.
UniProtKB T1JGB9, 2013, https://www.uniprot.org/uniprot/T1JGB9.
GenBank KJZ10850 (2015, https://www.ncbi.nlm.nih.gov/protein/KJZ10850.1).
Guo et al., 2004, Proc. Natl. Acad. Sci. USA 101; pp. 9205-9210.
Reboul et al., 2016, Biochim, Biophys. Acta 1858, pp. 475-486.
Supplementary European Search Report for EP Application No. 17849253 dated Apr. 9, 2020.
Database EMBL [Online]; "*Lachnospiraceae* bacterium 3_1_57AA_CT1 hypothetical protein", XP002798025; Database Assession No. EGN33025, Jun. 13, 2013.
"SubNameL Full=Uncharacterized protein (Eco:0000313: EMBL: egn33025.1);" xp002798026 retrieved from EBI Assession No. UNIPROT: F7KHG1, Database Assession No. F7KHG1, Sep. 21, 2011.
Database UniParc [Online]; XP002798030; Database Assession No. UPI0002134059, Sep. 21, 2011.
Pakula A.A. et al., Genetic analysis of protein stability and function. Annual Review of Genetics, 1989, No. 23, pp. 289-310.
Xu et al., Acta Cryst. F66: 1297-1305, 2010.
Meehan et al, 2014, Genome Biol. Evol. 6:703-713, including Supplementary table S2).
Ward et al., GenBank Accession No. ACTP02000009, https://www.ncbi.nlm.gov/nuccore/ACTP02000009, 2013.
Klock et al, 2008, Proteins 71:982-994.

* cited by examiner

*Primary Examiner* — Anne Kubelik
(74) *Attorney, Agent, or Firm* — Katherine Seguin

(57) ABSTRACT

Compositions and methods for controlling plant pests are disclosed. In particular, novel insecticidal proteins having toxicity Coleopteran and/or Lepidopteran insect pests are provided. Nucleic acid molecules encoding the novel insecticidal proteins are also provided. Methods of making the insecticidal proteins and methods of using the insecticidal proteins and nucleic acids encoding the insecticidal proteins of the invention, for example in transgenic plants to confer protection from insect damage, are also disclosed.

9 Claims, No Drawings
Specification includes a Sequence Listing.

INSECTICIDAL PROTEINS

RELATED APPLICATION INFORMATION

This application is a continuation of U.S. application Ser. No. 16/322,162 filed Jan. 31, 2019, which is a 371 of International Application No. PCT/US2017/045256, filed Aug. 3, 2017, which claims priority to U.S. Provisional Application No. 62/372,375, filed Aug. 9, 2016, the contents of each of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled "81094 ST25.txt", 86 kilobytes in size, generated on Sep. 1, 2021 and filed via EFSWeb is provided in lieu of a paper copy. This Sequence Listing is hereby incorporated by reference into the specification for its disclosures.

FIELD OF THE INVENTION

The present invention relates to the fields of protein engineering, plant molecular biology and pest control. More particularly the invention relates to a novel protein and its variants having insecticidal activity, nucleic acids whose expression results in the insecticidal proteins, and methods of making and methods of using the insecticidal proteins and corresponding nucleic acids to control insects.

BACKGROUND

Insect pests are a major cause of crop losses. In the US alone, billions of dollars are lost every year due to infestation by various genera of insects. In addition to losses in field crops, insect pests are also a burden to vegetable and fruit growers, to producers of ornamental flowers, and they are a nuisance to gardeners and homeowners.

Species of corn rootworm are considered to be the most destructive corn pests. In the United States, the three important species are *Diabrotica virgifera virgifera*, the western corn rootworm, *D. longicornis barberi*, the northern corn rootworm and *D. undecimpunctata howardi*, the southern corn rootworm. Only western and northern corn rootworms are considered primary pests of corn in the US Corn Belt. Additionally, an important corn rootworm pest in the Southern US is the Mexican corn rootworm, *Diabrotica virgifera zeae*. Corn rootworm larvae cause the most substantial plant damage by feeding almost exclusively on corn roots. This injury has been shown to increase plant lodging, to reduce grain yield and vegetative yield as well as alter the nutrient content of the grain. Larval feeding also causes indirect effects on corn by opening avenues through the roots for bacterial and fungal infections which lead to root and stalk rot diseases. Adult corn rootworms are active in cornfields in late summer where they feed on ears, silks and pollen, thus interfering with normal pollination.

Corn rootworms are mainly controlled by intensive applications of chemical pesticides, which are active through inhibition of insect growth, prevention of insect feeding or reproduction, or cause death. Good corn rootworm control can thus be reached, but these chemicals can sometimes also affect other, beneficial organisms. Another problem resulting from the wide use of chemical pesticides is the appearance of resistant insect varieties. Yet another problem is due to the fact that corn rootworm larvae feed underground thus making it difficult to apply rescue treatments of insecticides. Therefore, most insecticide applications are made prophylactically at the time of planting. This practice results in a large environmental burden. This has been partially alleviated by various farm management practices, but there is an increasing need for alternative pest control mechanisms.

Biological pest control agents, such as *Bacillus thuringiensis* (Bt) strains expressing pesticidal toxins like δ-endotoxins (delta-endotoxins; also called crystal toxins or Cry proteins), have been applied to crop plants with satisfactory results against insect pests. The δ-endotoxins are proteins held within a crystalline matrix that are known to possess insecticidal activity when ingested by certain insects. Several native Cry proteins from *Bacillus thuringiensis*, or engineered Cry proteins, have been expressed in transgenic crop plants and exploited commercially to control certain lepidopteran and coleopteran insect pests. For example, starting in 2003, transgenic corn hybrids that control corn rootworm by expressing a Cry3Bb1, Cry34Ab1/Cry35Ab1 or modified Cry3A (mCry3A) or Cry3Ab (eCry3.1Ab) protein have been available commercially in the US.

Although the usage of transgenic plants expressing Cry proteins has been shown to be extremely effective, insect pests that now have resistance against the Cry proteins expressed in certain transgenic plants are known. Therefore, there remains a need to identity new and effective pest control agents that provide an economic benefit to farmers and that are environmentally acceptable. Particularly needed are proteins that are toxic to *Diabrotica* species, a major pest of corn, that have a different mode of action than existing insect control products as a way to mitigate the development of resistance. Furthermore, delivery of insect control agents through products that minimize the burden on the environment, as through transgenic plants, are desirable.

SUMMARY

In view of these needs, the present invention provides novel insecticidal proteins, namely LachbCRW, its variants, and proteins which are substantially identical to LachbCRW and its variants. The proteins of the invention have toxicity to corn rootworm (*Diabrotica* spp). The invention is further drawn to nucleic acid molecules that encode LachbCRW or its variants, their complements, or which are substantially identical to LachbCRW and its variants.

Also included in the invention are vectors containing such recombinant (or complementary thereto) nucleic acids; a plant or microorganism which includes and enables expression of such nucleic acids; plants transformed with such nucleic acids, for example transgenic corn plants; the progeny of such plants which contain the nucleic acids stably incorporated and hereditable in a Mendelian manner, and/or the seeds of such plants and such progeny. The invention also includes methods of breeding to introduce a transgene comprising a nucleic acid molecule of the invention into a progeny plant and into various germplasms.

The invention also includes compositions and formulations containing LachbCRW or its variants, which are capable of inhibiting the ability of insect pests to survive, grow and/or reproduce, or of limiting insect-related damage or loss to crop plants, for example applying LachbCRW or its variants as part of compositions or formulations to insect-infested areas or plants, or to prophylactically treat insect-susceptible areas or plants to confer protection against the insect pests.

The invention is further drawn to a method of making LachbCRW or its variants and to methods of using the nucleic acids, for example in microorganisms to control insects or in transgenic plants to confer protection from insect damage.

The novel proteins described herein are active against insects. For example, in embodiments, the proteins of the present invention can be used to control economically important insect pests, including Coleopteran insects such as western corn rootworm (WCR), northern corn rootworm (NCR), southern corn rootworm (SCR) and/or Mexican corn rootworm (*D. virgifera zeae*). In embodiments, proteins of the present invention are also insecticidal against Lepidopeeran insect pests such as *Agrotis ipsilon* (black cutworm), *Diatraea saccharalis* (sugar cane borer) and/or *Diatraea grandiosella* (southwestern corn borer). The insecticidal proteins of the invention can be used singly or in combination with other insect control strategies to confer enhanced pest control efficiency against the same insect pest and/or to increase the spectrum of target insects with minimal environmental impact.

Other aspects and advantages of the present invention will become apparent to those skilled in the art from a study of the following description of the invention and non-limiting examples.

BRIEF DESCRIPTION OF THE SEQUENCES IN THE SEQUENCE LISTING

SEQ ID NO: 1 is the LachbCRW amino acid sequence.
SEQ ID NO: 2 is the LachbCRW Y164W amino acid sequence
SEQ ID NO: 3 is the LachbCRW Y164F amino acid sequence.
SEQ ID NO: 4 is the LachbCRW Y164W/I169L amino acid sequence.
SEQ ID NO: 5 is the LachbCRW Y164W/Y385W amino acid sequence.
SEQ ID NO: 6 is the LachbCRW Y164W/Y400W amino acid sequence.
SEQ ID NO: 7 is the LachbCRW Y164W/Y402W amino acid sequence.
SEQ ID NO: 8 is the LachbCRW Y164W/Y431W amino acid sequence.
SEQ ID NO: 9 is the LachbCRW Y164F/I169L amino acid sequence.
SEQ ID NO: 10 is the LachbCRW Y164F/T166S amino acid sequence.
SEQ ID NO: 11 is a fragment of LachbCRW motif amino acid sequence.
SEQ ID NO: 12 is a fragment of LachbCRW Y164W amino acid sequence.
SEQ ID NO: 13 is a fragment of LachbCRW Y164F amino acid sequence.
SEQ ID NO: 14 is a fragment of LachbCRW I169L amino acid sequence.
SEQ ID NO: 15 is a fragment of LachbCRW Y164W/I169L amino acid sequence.
SEQ ID NO: 16 is a fragment of LachbCRW Y164F/I169L amino acid sequence.
SEQ ID NO: 17 is the LachbCRW nucleotide sequence.
SEQ ID NO: 18 is the LachbCRW *E. coli* optimized nucleotide sequence.
SEQ ID NO: 19 is the LachbCRW Y164W *E. coli* optimized nucleotide sequence.
SEQ ID NO: 20 is the LachbCRW Y164F *E. coli* optimized nucleotide sequence.
SEQ ID NO: 21 is the LachbCRW Y164W/I169L *E. coli* optimized nucleotide sequence.
SEQ ID NO: 22 is the LachbCRW Y164W/Y385W *E. coli* optimized nucleotide sequence.
SEQ ID NO: 23 is the LachbCRW Y164W/Y400W *E. coli* optimized nucleotide sequence.
SEQ ID NO: 24 is the LachbCRW Y164W/Y402W *E. coli* optimized nucleotide sequence.
SEQ ID NO: 25 is the LachbCRW Y164W/Y431W *E. coli* optimized nucleotide sequence.
SEQ ID NO: 26 is the LachbCRW Y164F/I169L *E. coli* optimized nucleotide sequence.
SEQ ID NO: 27 is the LachbCRW Y164F/T166S *E. coli* optimized nucleotide sequence.
SEQ ID NO: 28 is the LachbCRW maize codon-optimized nucleotide sequence.
SEQ ID NO: 29 is the LachbCRW Y164W maize codon-optimized nucleotide sequence.
SEQ ID NO: 30 is the LachbCRW Y164F maize codon-optimized nucleotide sequence.
SEQ ID NO: 31 is the LachbCRW Y164F/I169L maize codon-optimized nucleotide sequence.
SEQ ID NO: 32 is the LachbCRW Y164W/Y385W maize codon-optimized nucleotide sequence.
SEQ ID NO: 33 is the LachbCRW Y164W/Y400W maize codon-optimized nucleotide sequence.
SEQ ID NO: 34 is the LachbCRW Y164W/Y402W maize codon-optimized nucleotide sequence.
SEQ ID NO: 35 is the LachbCRW Y164W/Y431W maize codon-optimized nucleotide sequence.
SEQ ID NO: 36 is the LachbCRW Y164W/I169L maize codon-optimized nucleotide sequence.
SEQ ID NO: 37 is the LachbCRW Y164W/T166S maize codon-optimized nucleotide sequence.

Definitions

For clarity, certain terms used in the specification are defined and presented as follows:

"Activity" of the insecticidal proteins of the invention is meant that the insecticidal proteins function as orally active insect control agents, have a toxic effect, and/or are able to disrupt or deter insect feeding, which may or may not cause death of the insect. When an insecticidal protein of the invention is delivered to the insect, the result is typically death of the insect, or the insect does not feed upon the source that makes the insecticidal protein available to the insect. "Pesticidal" is defined as a toxic biological activity capable of controlling a pest, such as an insect, nematode, fungus, bacteria, or virus, preferably by killing or destroying them. "Insecticidal" is defined as a toxic biological activity capable of controlling insects, preferably by killing them. A "pesticidal agent" is an agent that has pesticidal activity. An "insecticidal agent" is an agent that has insecticidal activity.

"Associated with/operatively linked" refer to two nucleic acids that are related physically or functionally. For example, a promoter or regulatory DNA sequence is said to be "associated with" a DNA sequence that codes for RNA or a protein if the two sequences are operatively linked, or situated such that the regulatory DNA sequence will affect the expression level of the coding or structural DNA sequence.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" an insecticidal protein means that the insecticidal protein comes in contact with an insect, resulting in a toxic effect and control of the insect. The insecticidal protein may be delivered in many recognized ways, e.g., through a transgenic plant expressing the insecticidal protein, formulated protein composition(s), sprayable protein composition(s), a bait matrix, or any other art-recognized toxin delivery system.

"Effective insect-controlling amount" means that concentration of an insecticidal protein that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may have at least one of its components heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used. Any available terminator known to function in plants can be used in the context of this invention.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. Inembodiments, "expression" refers to the transcription and stable accumulation of sense (mRNA) or functional RNA. "Expression" may also refer to the production of protein.

A "gene" is a defined region that is located within a genome and comprises a coding nucleic acid sequence and typically also comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

"Gene of interest" refers to any nucleic acid molecule which, when transferred to a plant, confers upon the plant a desired trait such as antibiotic resistance, virus resistance, insect resistance, disease resistance, or resistance to other pests, herbicide tolerance, abiotic stress tolerance, male sterility, modified fatty acid metabolism, modified carbohydrate metabolism, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence or nucleic acid molecule is a nucleic acid sequence or nucleic acid molecule not naturally associated with a host cell into which it is introduced, including non-naturally occurring multiple copies of a naturally occurring nucleic acid sequence. A heterologous nucleic acid sequence or nucleic acid molecule may comprise a chimeric sequence such as a chimeric expression cassette, where the promoter and the coding region are derived from multiple source organisms. The promoter sequence may be a constitutive promoter sequence, a tissue-specific promoter sequence, a chemically-inducible promoter sequence, a wound-inducible promoter sequence, a stress-inducible promoter sequence, or a developmental stage-specific promoter sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Identity" or "percent identity" refers to the degree of similarity between two nucleic acid or protein sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or at least about 85%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. *Nuc. Acids Res.*, 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Another indication that two nucleic acids are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

A further indication that two nucleic acids or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated toxin is a nucleic acid molecule or toxin that, by the hand of man, exists apart from its native environment and is therefore not a product of nature. An isolated nucleic acid molecule or toxin may exist in a purified form or may exist in a non-native environment such as, for example without limitation, a recombinant microbial cell, plant cell, plant tissue, or plant.

A "nucleic acid molecule" or "nucleic acid sequence" is a segment of single- or double-stranded DNA or RNA that can be isolated from any source. In the context of the present invention, the nucleic acid molecule is typically a segment of DNA. In some embodiments, the nucleic acid molecules of the invention are isolated nucleic acid molecules.

The terms "protein," "peptide" and "polypeptide" are used interchangeably herein.

As used herein, "codon optimized" sequence means the nucleotide sequence of a recombinant, transgenic, or synthetic polynucleotide wherein the codons are chosen to reflect the particular codon bias that a host cell may have. This is done in such a way so as to preserve the amino acid sequence of the polypeptide encoded by the codon optimized polynucleotide. In certain embodiments, the nucleotide sequence of the recombinant DNA construct includes a sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase and initiates transcription of the DNA. The promoter region may also include other elements that act as regulators of gene expression.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

"Transformation" is a process for introducing heterologous nucleic acid into a host cell or organism. In particular embodiments?, "transformation" means the stable integration of a DNA molecule into the genome (nuclear or plastid) of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations:

adenine (A), cytosine (C), thymine (T), and guanine (G) Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DETAILED DESCRIPTION

This invention relates to novel insecticidal proteins which have activity against coleopterans, for example, *Diabrotica virgifera virgifera* (western corn rootworm; WCR), *Diabrotica barberi* (northern corn rootworm; NCR), and/or *Diabrotica undecimpunctata howardi* (southern corn rootworm; SCR) and/or other *Diabrotica* species including *Diabrotica virgifera zeae* (Mexican corn rootworm), and/or Colorado Potato Beetle. In embodiments, a novel insecticidal protein of the invention may have activity against Lepidopteran species, including without limitation *Agrotis ipsilon* (black cutworm), *Diatraea saccharalis* (sugar cane borer) and/or *Diatraea grandiosella* (southwestern corn borer). The present invention also relates to nucleic acids whose expression results in insecticidal proteins of the invention, and to the making and using of the insecticidal proteins to control insect pests. In embodiments, the expression of the nucleic acids results in insecticidal proteins that can be used to control coleopteran insects such as western, northern and/or southern corn rootworm, particularly when expressed in a transgenic plant such as a transgenic corn plant.

The present invention further encompasses a nucleic acid molecule comprising a nucleotide sequence that encodes an insecticidal protein of the invention. The nucleotide sequence may be optimized for expression in bacteria, such as *Escherichia coli*, or for expression in a plant, such as *Zea mays*. A nucleotide sequence optimized for expression in a heterologous organism, such as a species of bacteria different from where it originated or a plant, is not naturally occurring. In one aspect of this embodiment, the nucleic acid molecule comprises a nucleotide sequence selected from the group consisting of SEQ ID NO: 18-37. Specifically exemplified teachings of methods to make nucleic acid molecules that encode the insecticidal proteins of the invention can be found in the examples of the present application. Those skilled in the art will recognize that modifications can be made to the exemplified methods to make the insecticidal proteins encompassed by the present invention.

A skilled person would recognize that a transgene for commercial use, such as a nucleic acid molecule that comprises any of SEQ ID NO: 17-37, may have relatively minor modifications to the nucleic acid sequence to comply with governmental regulatory standards. Such modifications would not affect the function of the resulting molecule, which would be substantially identical to SEQ ID NO: 17-37. A skilled person would recognize that the modified nucleic acid molecule would be essentially the same as the starting molecule, and is encompassed by the present invention.

The present invention also encompasses a nucleic acid molecule that comprises (a) a nucleotide sequence of any one of SEQ ID NOs: 17-37; (b) a nucleotide sequence that is at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of any one of SEQ ID NOs: 18-37; (c) a nucleotide sequence that encodes a polypeptide, wherein the amino acid sequence of the polypeptide comprises any one of SEQ ID NOs: 1-16, and has insect control activity; (d) a nucleotide sequence that encodes a polypeptide, wherein the amino acid sequence of the polypeptide is at least 80%, at least 85%, at least 90%, at least 91%, at least 92%, at least 93%, at least 94%, at least 95%, at least 96%, at least 97%, at least 98%, at least 99%, or is 100% identical to the amino acid sequence of any one of SEQ ID NOs: 1-16; or (e) a nucleotide sequence that is complementary to the nucleotide sequence of any one of (a) to (d) above.

The present invention further encompasses an expression cassette comprising a promoter operably linked to a heterologous nucleotide sequence that comprises: (a) a nucleotide sequence of any one of SEQ ID NOs: 17-37; (b) a nucleotide sequence that is at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of any one of SEQ ID NOs: 18-37; (c) a nucleotide sequence that encodes a polypeptide, wherein the amino acid sequence of the polypeptide comprises any one of SEQ ID NOs: 1-16, and has insect control activity; (d) a nucleotide sequence that encodes a polypeptide, wherein the amino acid sequence of the polypeptide is at least 80%, at least 85%, at least 90%, at least 91%, at least 92%, at least 93%, at least 94%, at least 95%, at least 96%, at least 97%, at least 98%, at least 99%, or is 100% identical to the amino acid sequence of any one of SEQ ID NOs: 1-16; or (e) a nucleotide sequence that is complementary to the nucleotide sequence of any one of (a) to (d) above. The expression cassette comprises a promoter operably linked to a heterologous nucleotide sequence and is not naturally occurring.

The present invention further comprises a polypeptide comprising an amino acid sequence of any one of SEQ ID NO: 2-10 or SEQ ID NO: 12-16. SEQ ID NOs: 2-10 or SEQ ID NOs: 12-16 contain engineered mutations or modifications and the sequences are not naturally occurring. Proteins comprising SEQ ID NOs: 2-10 or SEQ ID NO: 12-16, are exemplified in the present application as possessing insecticidal activity. Those skilled in the art will recognize that modifications can be made to the exemplified methods to make the insecticidal proteins encompassed by the present invention. Such modifications and substantially identical nucleic acid or amino acid molecules are encompassed by the present invention.

The present invention also encompasses recombinant vectors or constructs, which may also be referred to as vectors or constructs, comprising the expression cassettes and/or the nucleic acid molecules of this invention. In such vectors, the nucleic acids are preferably in expression cassettes comprising regulatory elements for expression of the nucleotide molecules in a host cell capable of expressing the nucleotide molecules. Such regulatory elements usually comprise promoter and termination signals and preferably also comprise elements allowing efficient translation of polypeptides encoded by the nucleic acids of the present invention. Vectors comprising the nucleic acids are may be capable of replication in particular host cells, preferably as extrachromosomal molecules, and are therefore used to amplify the nucleic acids of this invention in the host cells. The present invention also encompasses a host cell that contains an expression cassette or a nucleic acid molecule of the invention. In one embodiment, host cells for such vectors are microorganisms, such as bacteria, in particular *Bacillus thuringiensis* or *E. coli*, or such as fungi such as yeast. In another embodiment, host cells for such recombinant vectors are endophytes or epiphytes. In yet another embodiment, such vectors are viral vectors and are used for replication of the nucleotide sequences in particular host cells, e.g. insect cells or plant cells. Recombinant vectors are also used for transformation of the nucleotide molecules of this invention into host cells, whereby the nucleotide molecules are stably integrated into the DNA of a transgenic host. In one embodiment, the transgenic host is plant, for example a monocot plant, such as corn plant. In embodiments, the transgenic host plant is a dicot plant, such as a soybean plant or cotton plant.

In another embodiment, at least one of the nucleic acids of the invention is inserted into an appropriate expression cassette, comprising a promoter and termination signal. Expression of the nucleic acid may be constitutive, or an inducible promoter responding to various types of stimuli to initiate transcription may be used. In another embodiment, the cell in which the insecticidal protein of the invention is expressed is a microorganism, such as a virus, bacteria, or a fungus. In yet another embodiment, a virus, such as a baculovirus, contains a nucleic acid of the invention in its genome and expresses large amounts of the corresponding insecticidal protein after infection of appropriate eukaryotic cells that are suitable for virus replication and expression of the nucleic acid. The insecticidal protein thus produced is used as an insecticidal agent. Alternatively, baculoviruses engineered to include the nucleic acid are used to infect insects in vivo and kill them either by expression of the insecticidal toxin or by a combination of viral infection and expression of the insecticidal toxin. In a further embodiment, the present invention also encompasses a method for producing a polypeptide with insecticidal activity, comprising culturing the host cell under conditions in which the nucleic acid molecule encoding the polypeptide is expressed.

Bacterial cells are also hosts for the expression of the nucleic acids of the invention. In one embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleic acids for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In:Industrial Microorganisms:Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreekrishna, In:Industrial microorganisms:basic and applied molecular genetics, Baltz, Hegeman, and Skatrud eds., American Society for Microbiology, Washington (1993); Dequin & Barre, Biotechnology L2:173-177 (1994); van den Berg et al., Biotechnology 8:135-139 (1990)).

The insecticidal proteins of the present invention have insect control activity when tested against insect pests in bioassays. In one embodiment, the insecticidal proteins of the invention are active against coleopteran and/or lepidopteran insects. Insects in the order Lepidoptera include without limitation any insect now known or later identified that is classified as a lepidopteran, including those insect species within suborders Zeugloptera, Glossata, and Heterobathmiina, and any combination thereof. Exemplary lepidopteran insects include, but are not limited to, *Ostrinia* spp. such as *O. nubilalis* (European corn borer); *Plutella* spp. such as *P. xylostella* (diamondback moth); *Spodoptera* spp. such as *S. frugiperda* (fall armyworm), *S. ornithogalli* (yellowstriped armyworm), *S. praefica* (western yellowstriped armyworm), *S. eridania* (southern armyworm) and *S. exigua* (beet armyworm); *Agrotis* spp. such as *A. ipsilon* (black cutworm), *A. segetum* (common cutworm), *A. gladiaria* (claybacked cutworm), and *A. orthogonia* (pale western cutworm); *Striacosta* spp. such as *S. albicosta* (western bean cutworm); *Helicoverpa* spp. such as *H. zea* (corn earworm), *H. punctigera* (native budworm), *S. littoralis* (Egyptian cotton leafworm) and *H. armigera* (cotton bollworm); *Heliothis* spp. such as *H. virescens* (tobacco budworm); *Diatraea* spp. such as *D. grandiosella* (southwestern corn borer) and *D. saccharalis* (sugarcane borer); *Trichoplusia* spp. such as *T. ni* (cabbage looper); *Sesamia* spp. such as *S. nonagroides* (Mediterranean corn borer); *Pectinophora* spp. such as *P. gossypiella* (pink bollworm); *Cochylis* spp. such as *C. hospes* (banded sunflower moth); *Manduca* spp. such as *M. sexta* (tobacco hornworm) and *M. quinquemaculata* (tomato hornworm); *Elasmopalpus* spp. such as *E. lignosellus* (lesser cornstalk borer); *Pseudoplusia* spp. such as *P. includens* (soybean looper); *Anticarsia* spp. such as *A. gemmatalis* (velvetbean caterpillar); *Plathypena* spp. such as *P. scabra* (green cloverworm); *Pieris* spp. such as *P. brassicae* (cabbage butterfly), *Papaipema* spp. such as *P. nebris* (stalk borer); *Pseudaletia* spp. such as *P. unipuncta* (common armyworm); *Peridroma* spp. such as *P. saucia* (variegated cutworm); *Keiferia* spp. such as *K. lycopersicella* (tomato pinworm); *Artogeia* spp. such as *A. rapae* (imported cabbageworm); *Phthorimaea* spp. such as *P. operculella* (potato tuberworm); *Crymodes* spp. such as *C. devastator* (glassy cutworm); *Feltia* spp. such as *F. ducens* (dingy cutworm); and any combination of the foregoing. In one aspect of this embodiment, the insecticidal proteins of the invention are active against black cutworm, sugar cane borer, and/or southwestern corn borer.

Insects in the order Coleoptera include but are not limited to any coleopteran insect now known or later identified including those in suborders Archostemata, Myxophaga, Adephaga and Polyphaga, and any combination thereof.

In one aspect of this embodiment, the insecticidal proteins of the invention are active against *Diabrotica* spp. *Diabrotica* is a genus of beetles of the order Coleoptera commonly referred to as "corn rootworms" or "cucumber beetles." Exemplary *Diabrotica* species include without limitation *Diabrotica barberi* (northern corn rootworm), *D. virgifera virgifera* (western corn rootworm), *D. undecimpunctata howardii* (southern corn rootworm), *D. balteata* (banded cucumber beetle), *D. undecimpunctata undecimpunctata* (western spotted cucumber beetle), *D. significata* (3-spotted leaf beetle), *D. speciosa* (chrysanthemum beetle), *D. virgifera zeae* (Mexican corn rootworm), *D. beniensis, D. cristata, D. curviplustalata, D. dissimilis, D. elegantula, D. emorsitans, D. graminea, D. hispanloe, D. lemniscata, D. linsleyi, D. milleri, D. nummularis, D. occlusal, D. porrecea, D. scutellata, D. tibialis, D. trifasciata* and *D. viridula*; and any combination thereof.

Other nonlimiting examples of Coleopteran insect pests according to the present invention include *Leptinotarsa* spp. such as *L. decemlineata* (Colorado potato beetle); *Chrysomela* spp. such as *C. scripta* (cottonwood leaf beetle); *Hypothenemus* spp. such as *H. hampei* (coffee berry borer); *Sitophilus* spp. such as *S. zeamais* (maize weevil); *Epitrix* spp. such as *E. hirtipennis* (tobacco flea beetle) and *E. cucumeris* (potato flea beetle); *Phyllotreta* spp. such as *P. cruciferae* (crucifer flea beetle) and *P. pusilla* (western black flea beetle); *Anthonomus* spp. such as *A. eugenii* (pepper weevil); *Hemicrepidus* spp. such as *H. memnonius* (wireworms); *Melanotus* spp. such as *M. communis* (wireworm); *Ceutorhychus* spp. such as *C. assimilis* (cabbage seedpod weevil); *Phyllotreta* spp. such as *P. cruciferae* (crucifer flea beetle); *Aeolus* spp. such as *A. mellillus* (wireworm); *Aeolus* spp. such as *A. mancus* (wheat wireworm); *Horistonotus* spp. such as *H. uhlerii* (sand wireworm); *Sphenophorus* spp. such as *S. maidis* (maize billbug), *S. zeae* (timothy billbug), *S. parvulus* (bluegrass billbug), and *S. callosus* (southern corn billbug); *Phyllophaga* spp. (White grubs); *Chaetocnema* spp. such as *C. pulicaria* (corn flea beetle); *Popillia* spp. such as *P. japonica* (Japanese beetle); *Epilachna* spp. such as *E. varivestis* (Mexican bean beetle); *Cerotoma* spp. such as *C. trifurcate* (Bean leaf beetle); *Epicauta* spp. such as *E. pestifera* and *E. lemniscata* (Blister beetles); and any combination of the foregoing.

The insecticidal proteins of the invention may also be active against Hemipteran, Dipteran, *Lygus* spp., and/or other piercing and sucking insects, for example of the order Orthoptera or Thysanoptera. Insects in the order Diptera include but are not limited to any dipteran insect now known or later identified including but not limited to *Liriomyza* spp. such as *L. trifolii* (leafminer) and *L. sativae* (vegetable leafminer); *Scrobipalpula* spp. such as *S. absoluta* (tomato leafminer); *Delia* spp. such as *D. platura* (seedcorn maggot), *D. brassicae* (cabbage maggot) and *D. radicum* (cabbage root fly); *Psilia* spp. such as *P. rosae* (carrot rust fly); *Tetanops* spp. such as *T. myopaeformis* (sugarbeet root maggot); and any combination of the foregoing.

Insects in the order Orthoptera include but are not limited to any orthopteran insect now known or later identified including but not limited to *Melanoplus* spp. such as *M. differentialis* (Differential grasshopper), *M. femurrubrum* (Redlegged grasshopper), *M. bivittatus* (Twostriped grasshopper); and any combination thereof.

Insects in the order Thysanoptera include but are not limited to any thysanopteran insect now known or later identified including but not limited to *Frankliniella* spp. such as *F. occidentalis* (western flower thrips) and *F. fusca* (tobacco thrips); and *Thrips* spp. such as *T. tabaci* (onion thrips), *T. palmi* (melon thrips); and any combination of the foregoing.

The insecticidal proteins of the invention may also be active against nematodes. The term "nematode" as used herein encompasses any organism that is now known or later identified that is classified in the animal kingdom, phylum Nematoda, including without limitation nematodes within class Adenophorea (including for example, orders Enoplida, Isolaimida, Mononchida, Dorylaimida, Trichocephalida, Mermithida, Muspiceida, Araeolaimida, Chromadorida, Desmoscolecida, Desmodorida and Monhysterida) and/or class Secernentea (including, for example, orders Rhabdita, Strongylida, Ascaridida, Spirurida, Camallanida, Diplogasterida, Tylenchida and Aphelenchida).

Nematodes include but are not limited to parasitic nematodes such as root-knot nematodes, cyst nematodes and/or lesion nematodes. Exemplary genera of nematodes according to the present invention include but are not limited to, *Meloidogyne* (root-knot nematodes), *Heterodera* (cyst nematodes), *Globodera* (cyst nematodes), *Radopholus* (burrowing nematodes), *Rotylenchulus* (reniform nematodes), *Pratylenchus* (lesion nematodes), *Aphelenchoides* (foliar nematodes), *Helicotylenchus* (spiral nematodes), *Hoplolaimus* (lance nematodes), *Paratrichodorus* (stubby-root nematodes), *Longidorus, Nacobbus* (false root-knot nematodes), *Subanguina, Belonlaimus* (sting nematodes), *Criconemella, Criconemoides* (ring nematodes), *Ditylenchus, Dolichodorus, Hemicriconemoides, Hemicycliophora, Hirschmaniella, Hypsoperine, Macroposthonia, Melinius, Punctodera, Quinisulcius, Scutellonema, Xiphinema* (dagger nematodes), *Tylenchorhynchus* (stunt nematodes), *Tylenchulus, Bursaphelenchus* (round worms), and any combination thereof.

Exemplary plant parasitic nematodes according to the present invention include, but are not limited to, *Belonolaimus gracilis, Belonolaimus longicaudatus, Bursaphelenchus xylophilus* (pine wood nematode), *Criconemoides ornata, Ditylenchus destructor* (potato rot nematode), *Ditylenchus dipsaci* (stem and bulb nematode), *Globodera pallida* (potato cyst nematode), *Globodera rostochiensis* (golden nematode), *Heterodera glycines* (soybean cyst nematode), *Heterodera schachtii* (sugar beet cyst nematode); *Heterodera zeae* (corn cyst nematode), *Heterodera avenae* (cereal cyst nematode), *Heterodera carotae, Heterodera trifolii, Hoplolaimus columbus, Hoplolaimus galeatus, Hoplolaimus magnistylus, Longidorus breviannulatus, Meloidogyne arenaria, Meloidogyne chitwoodi, Meloidogyne hapla, Meloidogyne incognita, Meloidogyne javanica, Mesocriconema xenoplax, Nacobbus aberrans, Naccobus dorsalis, Paratrichodorus christiei, Paratrichodorus minor, Pratylenchus brachyurus, Pratylenchus crenatus, Pratylenchus hexincisus, Pratylenchus neglectus, Pratylenchus penetrans, Pratylenchus projectus, Pratylenchus scribneri, Pratylenchus tenuicaudatus, Pratylenchus thornei, Pratylenchus zeae, Punctodera chaccoensis, Quinisulcius acutus, Radopholus similis, Rotylenchulus reniformis, Tylenchorhynchus dubius, Tylenchulus semipenetrans* (citrus nematode), *Siphinema americanum, X. Mediterraneum*, and any combination of the foregoing.

In another embodiment, the invention encompasses a method of producing a insecticidal protein that is active against insects, comprising: (a) obtaining a host cell comprising a gene, which itself comprises an expression cassette and/or a nucleic acid molecule of the invention; and (b) growing the transgenic host cell in such a manner to express an insecticidal protein that is active against insects.

In yet a further embodiment, the invention encompasses a method of controlling insects, comprising delivering to the insects an effective insect-controlling amount of an insecticidal protein of the invention.

In one embodiment, at least one of the insecticidal proteins of the invention is expressed in a higher organism such as a plant. In this case, transgenic plants expressing effective insect-controlling amounts of the insecticidal protein protect themselves from insect pests. When the insect starts feeding on such a transgenic plant, it also ingests the expressed insecticidal protein. This will deter the insect from further biting into the plant tissue and/or may even harm or kill the insect. A nucleic acid of the present invention is inserted into an expression cassette, which may then be stably integrated in the genome of the plant. In another embodiment, the nucleic acid is included in a non-pathogenic self-replicating virus. Plants transformed in accordance with the present invention may be monocotyledonous or dicotyledonous and include, but are not limited to, corn, wheat, oat, turfgrass, pasture grass, flax, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, *papaya*, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

In another embodiment, the invention encompasses a method of producing a plant or plant part having enhanced insect resistance as compared to a control plant or plant part, comprising: (a) introducing a nucleic acid molecule comprising an expression cassette of the invention; and (b) growing the plant part into a plant that expresses the heterologous nucleic acid molecule of the expression cassette and that has enhanced insect resistance as compared to a control plant or plant part that has not been transformed with a nucleic acid molecule comprising the expression cassette. In a preferred embodiment, the expression cassette may encode a polypeptide comprising an amino acid sequence that is at least 80%, at least 85%, at least 90%, at least 91%, at least 92%, at least 93%, at least 94%, at least 95%, at least 96%, at least 97%, at least 98%, at least 99%, or is 100% identical or similar to any one of SEQ ID NO: 1-16. In a preferred embodiment, the expression cassette may encode a polypeptide comprising an amino acid sequence that is at least 80% identical to SEQ ID NO: 9. "Enhanced" insect resistance may be measured as an increase insecticidal activity Enhanced insect resistance may be greater than 0%, at least 1%, at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, at least 100%, at least 125%, at least 150%, at least 200%, at least 300%, at least 400%, at least 500%, at least 600%, at least 700%, at least 800%, at least 900%, or at least 1000% greater insecticidal activity compared to a control plant. A plant or plant part having enhance insect resistance as compared to a control plant or plant part may be produced by methods of plant transformation, plant tissue culture, or breeding. The plant or plant part may be produced by methods of sexual or asexual propagation. Any suitable control plant or plant part can be used, for example a plant of the same or similar genetic background grown in the same environment. In embodiments, the control plant or plant part is of the same genetic background and is growing in the same environment as the described plant, but it does not comprise a molecule of the invention, while the described plant does comprise a molecule of the invention.

In another embodiment, the invention encompasses a method of enhancing insect resistance in a plant or plant part as compared to a control plant or plant part, comprising expressing in the plant or plant part a nucleic acid molecule or an expression cassette of the invention, wherein expression of the heterologous nucleic acid of the expression cassette results in enhanced insect resistance in a plant or plant part as compared to a control plant or plant part. In embodiments, the expression cassette or nucleic acid molecule comprises a promoter operably linked to a heterologous nucleic acid molecule comprising a nucleotide sequence that comprises: (a) a nucleotide sequence of any one of SEQ ID NOs: 18-37; (b) a nucleotide sequence that is at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of any one of SEQ ID NOs: 18-37; (c) a nucleotide sequence that encodes a polypeptide, wherein the amino acid sequence of the polypeptide comprises any one of SEQ ID NOs: 1-16, and has insect control activity; (d) a nucleotide sequence that encodes a polypeptide, wherein the amino acid sequence of the polypeptide is at least 80%, at least 85%, at least 90%, at least 91%, at least 92%, at least 93%, at least 94%, at least 95%, at least 96%, at least 97%, at least 98%, at least 99%, or is 100% identical to the amino acid sequence of any one of SEQ ID NOs: 1-16; or (e) a nucleotide sequence that is complementary to the nucleotide sequence of any one of (a) to (d) above. The nucleic acid molecule or expression cassette may be introduced into the plant. In some embodiments, the nucleic acid molecule or expression cassette may be introduced into a plant part and a plant comprising the nucleic acid molecule or expression cassette may be produced from the plant part.

In another embodiment, the invention encompasses a method of producing a plant having enhanced insect resistance as compared to a control plant, comprising detecting, in a plant part, a heterologous nucleic acid comprising a nucleic acid molecule or an expression cassette of the invention and producing a plant from the plant part, thereby producing a plant having enhanced insect resistance as compared to a control plant. In a further embodiment, the invention encompasses a method of identifying a plant or plant part having enhanced insect resistance as compared to a control plant or plant part, comprising detecting, in the plant or plant part, a nucleic acid molecule or an expression cassette of the invention, thereby identifying a plant or plant part having enhanced insect resistance. In a further embodiment, the expression cassette or a diagnostic fragment thereof is detected in an amplification product from a nucleic acid sample from the plant or plant part. The diagnostic fragment may be a nucleic acid molecule at least 10 contiguous nucleotides long which is unique to the expression cassette of the invention.

In yet another embodiment, the invention encompasses a method of producing a plant having enhanced insect resistance as compared to a control plant or plant part, comprising crossing a first parent plant with a second parent plant, wherein at least the first parent plant comprises within its genome a heterologous nucleic acid that comprises a nucleic acid molecule or an expression cassette of the invention and producing a progeny generation, wherein the progeny generation comprises at least one plant that possesses the heterologous nucleic acid within its genome and that exhibits enhanced insect resistance as compared to a control plant.

In preferred embodiments, the methods of the invention confer enhanced insect resistance in a plant or plant part against a coleopteran and/or a lepidopteran insect pest. Insect control of both lepidopteran and coleopteran insect pests are demonstrated in the Examples. In further embodiments, the methods of the invention confer enhanced insect resistance in a plant or plant part against *Diabrotica* species, including *Diabrotica virgifera virgifera, Diabrotica barberi, Diabrotica undecimpunctata howardi, Diabrotica virgifera zeae*, and/or *Diabrotica speciosa*, and/or related species. In further embodiments, the methods of the invention confer enhanced insect resistance in a plant or plant part against *Diabrotica virgifera virgifera, Diabrotica barberi*, and/or *Diabrotica undecimpunctata howardi*.

In preferred embodiments, the methods of the invention confer enhanced insect resistance in a monocotyledonous plant.

The present invention further encompasses a transgenic plant comprising a a heterologous nucleic acid molecule or an expression cassette of the invention, which when transcribed and translated confers enhanced insect resistance. In preferred embodiments, the heterologous nucleic acid molecule comprises a sequence at least 80%, at least 85%, at least 90%, at least 91% at least 92%, at least 93%, at least 94%, at least 95%, at least 96%, at least 97%, at least 98% at least 99%, or 100% identical to any one of SEQ ID NOs: 17-37. In a further embodiment, the transgenic plant comprises a heterologous nucleic acid molecule comprising a sequence at least 80%, at least 85%, at least 90%, at least 91% at least 92%, at least 93%, at least 94%, at least 95%, at least 96%, at least 97%, at least 98% at least 99%, or 100% identical to SEQ ID NO: 37. In embodiments, the transgenic plant is a dicotyledonous plant. In preferred embodiments, the transgenic plant is a monocotyledonous plant. In further embodiments, the transgenic plant is alfalfa, aneth, apple, apricot, artichoke, arugula, asparagus, avocado, banana, beans, beet, blackberry, blueberry, broccoli, brussel sprouts, cabbage, canola, cantaloupe, carrot, cassava, cauliflower, celery, cherry, cilantro, citrus, clementine, coffee, corn, cotton, cucumber, Douglas fir, eggplant, endive, escarole, *eucalyptus*, fennel, figs, gourd, grape, grapefruit, honey dew, jicama, kiwifruit, lettuce, leeks, lemon, lime, Loblolly pine, mango, melon, mushroom, nut, okra, onion, orange, an ornamental plant, *papaya*, parsley, pea, peach, peanut, pear, pepper, persimmon, pine, pineapple, plantain, plum, pomegranate, poplar, potato, pumpkin, quince, *radiata* pine, radicchio, radish, raspberry, rice, rye, sorghum, Southern pine, soybean, spinach, squash, strawberry, sugarbeet, sunflower, sweet potato, sweetgum, tangerine, tea, tobacco, tomato, turf, a vine, watermelon, yams, or zucchini. In preferred embodiments, the transgenic plant is millet, switchgrass, maize, sorghum, wheat, oat, turf grass, pasture grass, flax, rice, sugarcane, oilseed rape, or barley.

In yet another embodiment, a transgenic plant of the invention comprises a heterologous nucleic acid molecule comprising a promoter sequence. In yet another embodiment, a transgenic plant of the invention may comprise a heterologous nucleic acid molecule which encodes for at least one additional desired trait. The additional trait may be encoded on the same heterologous nucleic acid molecule as a molecule of the invention, or it may be encoded on a second heterologous nucleic acid molecule. The additional desired trait may confer insect resistance to a second insect pest, insect resistance to the same insect pest, abiotic stress tolerance, male sterility, herbicide resistance, bacterial disease resistance, fungal disease resistance, viral disease resistance, nematode resistance, modified fatty acid metabolism, modified carbohydrate metabolism, improved nutritional value, improved performance in an industrial process or altered reproductive capability. The additional desired trait may also induce production within the plant of a commercially valuable enzyme or metabolite.

In embodiments, the desired added trait is a second pesticidal agent. The second pesticidal agent may be active on any plant pest, including insects, nematodes, fungi, viruses or bacteria. Examples of insect plant pests include and are not limited to *Nilaparvata* spp. (e.g. *N. lugens* (brown planthopper)); *Laodelphax* spp. (e.g. *L. striatellus* (small brown planthopper)); *Nephotettix* spp. (e.g. *N. virescens* or *N. cincticeps* (green leafhopper), or *N. nigropictus* (rice leafhopper)); *Sogatella* spp. (e.g. *S. furcifera* (whitebacked planthopper)); *Blissus* spp. (e.g. *B. leucopterus leucopterus* (chinch bug)); *Scotinophora* spp. (e.g. *S. vermidulate* (rice blackbug)); *Acrosternum* spp. (e.g. *A. hilare* (green stink bug)); *Parnara* spp. (e.g. *P. guttata* (rice skipper)); *Chilo* spp. (e.g. *C. suppressalis* (rice striped stem borer), *C. auricilius* (gold-fringed stem borer), or *C. polychrysus* (dark-headed stem borer)); *Chilotraea* spp. (e.g. *C. polychrysa* (rice stalk borer)); *Sesamia* spp. (e.g. *S. inferens* (pink rice borer)); *Tryporyza* spp. (e.g. *T. innotata* (white rice borer), or *T. incertulas* (yellow rice borer)); *Cnaphalocrocis* spp. (e.g. *C. medinalis* (rice leafroller)); *Agromyza* spp. (e.g. *A. oryzae* (leafminer), or *A. parvicornis* (corn blot leafminer)); *Diatraea* spp. (e.g. *D. saccharalis* (sugarcane borer), or *D. grandiosella* (southwestern corn borer)); *Narnaga* spp. (e.g. *N. aenescens* (green rice caterpillar)); *Xanthodes* spp. (e.g. *X. transversa* (green caterpillar)); *Spodoptera* spp. (e.g. *S. frugiperda* (fall armyworm), *S. exigua* (beet armyworm), *S. littoralis* (climbing cutworm) or *S. praefica* (western yellowstriped armyworm)); *Mythimna* spp. (e.g. Mythmna (*Pseudaletia*) seperata (armyworm)); *Helicoverpa* spp. (e.g. *H. zea* (corn earworm)); *Colaspis* spp. (e.g. *C. brunnea* (grape *colaspis*)); *Lissorhoptrus* spp. (e.g. *L. oryzophilus* (rice water weevil)); *Echinocnemus* spp. (e.g. *E. squamos* (rice plant weevil)); *Diclodispa* spp. (e.g. *D. armigera* (rice hispa)); *Oulema* spp. (e.g. *O. oryzae* (leaf beetle); *Sitophilus* spp. (e.g. *S. oryzae* (rice weevil)); *Pachydiplosis* spp. (e.g. *P. oryzae* (rice gall midge)); *Hydrellia* spp. (e.g. *H. griseola* (small rice leafminer), or *H. sasakii* (rice stem maggot)); *Chlorops* spp. (e.g. *C. oryzae* (stem maggot)); *Diabrotica* spp. (e.g. *D. virgifera virgifera* (western corn rootworm), *D. barberi* (northern corn rootworm), *D. undecimpunctata howardi* (southern corn rootworm), *D. virgifera zeae* (Mexican corn rootworm); *D. balteata* (banded cucumber beetle)); *Ostrinia* spp. (e.g. *O. nubilalis* (European corn borer)); *Agrotis* spp. (e.g. *A. ipsilon* (black cutworm)); *Elasmopalpus* spp. (e.g. *E. lignosellus* (lesser cornstalk borer)); *Melanotus* spp. (wireworms); *Cyclocephala* spp. (e.g. *C. borealis* (northern masked chafer), or *C. immaculata* (southern masked chafer)); *Popillia* spp. (e.g. *P. japonica* (Japanese beetle)); *Chaetocnema* spp. (e.g. *C. pulicaria* (corn flea beetle)); *Sphenophorus* spp. (e.g. *S. maidis* (maize billbug)); *Rhopalosiphum* spp. (e.g. *R. maidis* (corn leaf aphid)); *Anuraphis* spp. (e.g. *A. maidiradicis* (corn root aphid)); *Melanoplus* spp. (e.g. *M. femurrubrum* (red-legged grasshopper) *M. differentialis* (differential grasshopper) or *M. sanguinipes* (migratory grasshopper)); *Hylemya* spp. (e.g. *H. platura* (seedcorn maggot)); *Anaphothrips* spp.

(e.g. *A. obscrurus* (grass thrips)); *Solenopsis* spp. (e.g. *S. milesta* (thief ant)); or spp. (e.g. *T. urticae* (twospotted spider mite), *T. cinnabarinus* (carmine spider mite); *Helicoverpa* spp. (e.g. *H. zea* (cotton bollworm), or *H. armigera* (American bollworm)); *Pectinophora* spp. (e.g. *P. gossypiella* (pink bollworm)); *Earias* spp. (e.g. *E. vittella* (spotted bollworm)); *Heliothis* spp. (e.g. *H. virescens* (tobacco budworm)); *Anthonomus* spp. (e.g. *A. grandis* (boll weevil)); *Pseudatomoscelis* spp. (e.g. *P. seriatus* (cotton fleahopper)); *Trialeurodes* spp. (e.g. *T. abutiloneus* (banded-winged whitefly) *T. vaporariorum* (greenhouse whitefly)); *Bemisia* spp. (e.g. *B. argentifolii* (silverleaf whitefly)); *Aphis* spp. (e.g. *A. gossypii* (cotton aphid)); *Lygus* spp. (e.g. *L. lineolaris* (tarnished plant bug) or *L. hesperus* (western tarnished plant bug)); *Euschistus* spp. (e.g. *E. conspersus* (consperse stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion *thrips*)); *Frankliniella* spp. (e.g. *F. fusca* (tobacco *thrips*), or *F. occidentalis* (western flower *thrips*)); *Leptinotarsa* spp. (e.g. *L. decemlineata* (Colorado potato beetle), *L. juncta* (false potato beetle), or *L. texana* (Texan false potato beetle)); *Lema* spp. (e.g. *L. trilineata* (three-lined potato beetle)); *Epitrix* spp. (e.g. *E. cucumeris* (potato flea beetle), *E. hirtipennis* (flea beetle), or *E. tuberis* (tuber flea beetle)); *Epicauta* spp. (e.g. *E. vittata* (striped blister beetle)); *Phaedon* spp. (e.g. *P. cochleariae* (mustard leaf beetle)); *Epilachna* spp. (e.g. *E. varivetis* (mexican bean beetle)); *Acheta* spp. (e.g. *A. domesticus* (house cricket)); *Empoasca* spp. (e.g. *E. fabae* (potato leafhopper)); *Myzus* spp. (e.g. *M. persicae* (green peach aphid)); *Paratrioza* spp. (e.g. *P. cockerelli* (psyllid)); *Conoderus* spp. (e.g. *C. falli* (southern potato wireworm), or *C. vespertinus* (tobacco wireworm)); *Phthorimaea* spp. (e.g. *P. operculella* (potato tuberworm)); *Macrosiphum* spp. (e.g. *M. euphorbiae* (potato aphid)); *Thyanta* spp. (e.g. *T. pallidovirens* (redshouldered stinkbug)); *Phthorimaea* spp. (e.g. *P. operculella* (potato tuberworm)); *Helicoverpa* spp. (e.g. *H. zea* (tomato fruitworm); *Keiferia* spp. (e.g. *K. lycopersicella* (tomato pinworm)); *Limonius* spp. (wireworms); *Manduca* spp. (e.g. *M. sexta* (tobacco hornworm), or *M. quinquemaculata* (tomato hornworm)); *Liriomyza* spp. (e.g. *L. sativae, L. trifolli* or *L. huidobrensis* (leafminer)); *Drosophilla* spp. (e.g. *D. melanogaster, D. yakuba, D. pseudoobscura* or *D. simulans*); *Carabus* spp. (e.g. *C. granulatus*); *Chironomus* spp. (e.g. *C. tentanus*); *Ctenocephalides* spp. (e.g. *C. felis* (cat flea)); *Diaprepes* spp. (e.g. *D. abbreviatus* (root weevil)); *Ips* spp. (e.g. *I. pini* (pine engraver)); *Tribolium* spp. (e.g. *T. castaneum* (red floor beetle)); *Glossina* spp. (e.g. *G. morsitans* (tsetse fly)); *Anopheles* spp. (e.g. *A. gambiae* (malaria mosquito)); *Helicoverpa* spp. (e.g. *H. armigera* (African Bollworm)); *Acyrthosiphon* spp. (e.g. *A. pisum* (pea aphid)); Apis spp. (e.g. *A. melifera* (honey bee)); Homalodisca spp. (e.g. H. coagulate (glassy-winged sharpshooter)); *Aedes* spp. (e.g. *Ae. aegypti* (yellow fever mosquito)); *Bombyx* spp. (e.g. *B. mori* (silkworm)); *Locusta* spp. (e.g. *L. migratoria* (migratory locust)); *Boophilus* spp. (e.g. *B. microplus* (cattle tick)); *Acanthoscurria* spp. (e.g. *A. gomesiana* (red-haired chololate bird eater)); *Diploptera* spp. (e.g. *D. punctata* (pacific beetle cockroach)); *Heliconius* spp. (e.g. *H. erato* (red passion flower butterfly) or *H. melpomene* (postman butterfly)); *Curculio* spp. (e.g. *C. glandium* (acorn weevil)); *Plutella* spp. (e.g. *P. xylostella* (diamondback moth)); *Amblyomma* spp. (e.g. *A. variegatum* (cattle tick)); *Anteraea* spp. (e.g. *A. yamamai* (silkmoth)); and *Armigeres* spp. (e.g. *A. subalbatus*).

The insecticidal proteins of the invention can be used in combination with other pesticidal agents (e.g. Bt Cry proteins) to increase pest target range. Furthermore, the use of the insecticidal proteins of the invention in combination with an insecticidal agent which has a different mode of action or target a different receptor in the insect gut has particular utility for the prevention and/or management of insect resistance.

The second pesticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP (Vegetative Insecticidal Protein, disclosed in U.S. Pat. Nos. 5,849,870 and 5,877,012, herein incorporated by reference), a TIC900 or related protein, a TIC901, TIC1201, TIC407, TIC417,a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A (U.S. Pat. No. 7,276,583, incorporated by reference herein), eCry3.1Ab (U.S. Pat. No. 8,309,516, incorporated by reference herein), and Vip3A proteins, including Vip3Aa (U.S. Pat. No. 6,137,033, incorporated by reference herein).

In other embodiments, a transgenic plant of the invention may comprise a second pesticidal agent which may be derived from sources other than *B. thuringiensis*. The second insecticidal agent can be an agent selected from the group comprising an a amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabus, Serratia,* or *Yersinia*. In other embodiments. The insecticidal protein may be an ADP-ribosyltransferase derived from an insecticidal bacteria, such as *Photorhabdus* ssp. In still other embodiments, the insecticidal protein may Axmi205 or derived from Axmi205 (U.S. Pat. Nos. 8,575,425 and 9,394,345, each incorporated herein by reference). In other embodiments, the insecticidal protein may be a VIP protein, such as VIP1 and/or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In some embodiments, the transgenic plant of the invention may comprise at least a second pesticidal agent which is non-proteinaceous. In preferred embodiments, the second pesticidal agent is an interfering RNA molecule. An interfering RNA typically comprises at least a RNA fragment against a target gene, a spacer sequence, and a second RNA fragment which is complementary to the first, so that a double-stranded RNA structure can be formed. RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Interfering RNAs are known in the art to be useful for insect control (see, for example, publication WO2013/192256, incorporated by reference herein). An interfering RNA designed for use in insect control produces a non-naturally occurring double-stranded RNA, which takes advantage of the native RNAi pathways in the insect to trigger down-regulation of target genes that may lead to the cessation of feeding and/or growth and may result in the death of the insect pest. The interfering RNA molecule may confer insect resistance against the same target pest as the protein of the invention, or may target a different pest. The targeted insect plant pest may feed by chewing, sucking, or piercing. Interfering RNAs are known in the art to be useful for insect control. In other embodiments, the interfering RNA may confer resistance against a non-insect plant pest, such as a nematode pest or a virus pest.

The co-expression of more than one pesticidal agent in the same transgenic plant can be achieved by making a single recombinant vector comprising coding sequences of more than one pesticidal agent in a so called molecular stack and genetically engineering a plant to contain and express all the pesticidal agents in the transgenic plant. Such molecular stacks may be also be made by using mini-chromosomes as described, for example in U.S. Pat. No. 7,235,716. Alternatively, a transgenic plant comprising one nucleic acid encoding a first pesticidal agent can be re-transformed with a different nucleic acid encoding a second pesticidal agent and so forth. Alternatively, a plant, Parent 1, can be genetically engineered for the expression of genes of the present invention. A second plant, Parent 2, can be genetically engineered for the expression of a second pesticidal agent. By crossing Parent 1 with Parent 2, progeny plants are obtained which express all the genes introduced into Parents 1 and 2.

Transgenic plants or seed comprising an insecticidal protein of the invention can also be treated with an insecticide or insecticidal seed coating as described in U.S. Pat. Nos. 5,849,320 and 5,876,739, herein incorporated by reference. Where both the insecticide or insecticidal seed coating and the transgenic plant or seed of the invention are active against the same target insect, for example a Coleopteran pest or a *Diabrotica* target pest, the combination is useful (i) in a method for further enhancing activity of the composition of the invention against the target insect, and (ii) in a method for preventing development of resistance to the composition of the invention by providing yet another mechanism of action against the target insect. Thus, the invention provides a method of enhancing control of a *Diabrotica* insect population comprising providing a transgenic plant or seed of the invention and applying to the plant or the seed an insecticide or insecticidal seed coating to a transgenic plant or seed of the invention.

Even where the insecticidal seed coating is active against a different insect, the insecticidal seed coating is useful to expand the range of insect control, for example by adding an insecticidal seed coating that has activity against lepidopteran insects to a transgenic seed of the invention, which, in some embodiments, has activity against coleopteran and some lepidopteran insects, the coated transgenic seed produced controls both lepidopteran and coleopteran insect pests.

Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan® (carbofuran), Lanate® (methomyl, metomil, mesomile), Sevin® (carbaryl), Talstar® (bifenthrin), Force® (tefluthrin), Ammo® (cypermethrin), Cymbush® (cypermethrin), Delta Gold® (deltamethrin), Karate® (lambda-cyhalothrin), Ambush® (permethrin), Pounce® (permethrin), Brigade® (bifenthrin), Capture® (bifenthrin), ProShield® (tefluthrin), Warrior® (lambda-cyhalothrin), Dursban® (chlorphyrifos), Fortress® (chlorethoxyfos), Mocap® (ethoprop), Thimet® (phorate), AAstar® (phorate, flucythinate), Rampart® (phorate), Counter® (terbufos), Cygon® (dimethoate), Dicapthon, Regent® (fipronil), Cruiser® (thiamethoxam), Gaucho® (imidacloprid), Prescribe® (imidacloprid), Poncho® (clothianidin) and Aztec® (cyfluthrin, tebupirimphos).

The present invention also encompasses a composition comprising an effective insect-controlling amount of an insecticidal protein according to the invention. In further embodiments, the composition comprises a suitable agricultural carrier and a polypeptide of the invention with insecticidal activity. The agricultural carrier may include adjuvants, mixers, enhancers, etc. beneficial for application of an active ingredient, such as a polypeptide of the invention, including a polypeptide comprising an amino acid sequence that is at least 80%, at least 85%, at least 90%, at least 95%, or 100% identical to of any of SEQ ID NO: 1-16. Suitable carriers should not be phytotoxic to valuable crops, particularly at the concentrations employed in applying the compositions in the presence of crops, and should not react chemically with the compounds of the active ingredient herein, namely a polypeptide of the invention, or other composition ingredients. Such mixtures can be designed for application directly to crops, or can be concentrates or formulations which are normally diluted with additional carriers and adjuvants before application. They may include inert or active components and can be solids, such as, for example, dusts, powders, granules, water dispersible granules, or wettable powders, or liquids, such as, for example, emulsifiable concentrates, solutions, emulsions or suspensions. Suitable agricultural carriers may include liquid carriers, for example water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers may include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like. In another embodiment, a polypeptide of the invention may be encapsulated in a synthetic matrix such as a polymer and applied to the surface of a host such as a plant. Ingestion of the host cells by an insect permits delivery of the insect control agents to the insect and results in a toxic effect in the insect pest.

In further embodiments, a composition of the invention may be a powder, dust, pellet, granule, spray, emulsion, colloid, or solution. A composition of the invention may be prepared by desiccation, lyophilization, homogenization, extraction, filtration, centrifugation, sedimentation, or concentration of a culture of bacterial cells. A composition of the invention may comprise at least 1%, about 5%, at least 10%, at least 20%, at least 25%, at least 30%, at least 35%, at least 40%, at least 50%, at least 60%, at least 70%, at least 80%, at least 90%, at least 95%, at least 97%, or at least 99% by weight a polypeptide of the invention. A composition of the invention may comprise at least a second pesticidal agent, which may be insecticidal, nematicidal, fungicidal, or bactericidal. At least a second pesticidal agent may be insecticidal to the same insect as a polypeptide of the invention or to a different insect. The second pesticidal agent may be a polypeptide. The pesticidal agent may be an interfering RNA. The second pesticidal agent may be a microorganism, such as a bacteria, which comprises a nucleic acid molecule that encodes for a pesticidal agent and/or contains a pesticidal agent such as a polypeptide or interfering RNA. The microorganism may be attenuated, heat-inactivated, or lyophilized. The microorganism may be dead or unable to reproduce. The second pesticidal agent may be an insecticide, for example arbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimiphos, fipronil, acetamiprid, imidacloprid, thiacloprid, thiamethoxam, endosulfan, bensultap, or a combination thereof, or a commercial product containing such insecticides and insecticidal seed coatings as described above.

A composition of the invention, for example a composition comprising a polypeptide of the invention and an agriculturally acceptable carrier, may be used in conventional agricultural methods. An agriculturally acceptable carrier is a formulation useful for applying a composition comprising a polypeptide of the invention to a plant or seed. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

The present invention also comprises a method for controlling a Lepidopteran and/or Coleopteran pest population comprising contacting said population with an effective insect-controlling amount of a polypeptide of the invention with insecticidal activity, where the polypeptide is at least 80%, at least 85%, at least 90%, at least 91%, at least 92%, at least 93%, at least 94%, at least 95%, at least 96%, at least 97%, at least 98%, at least 99%, or is 100% identical to any one of SEQ ID NO: 1-16. Contacting includes members of the pest population feeding on or ingesting the polypeptide. The polypeptide may be incorporated into insect diet food or may be expressed in or present on plant tissue which the insect then ingests. In further embodiments, controlling the Lepidopteran and/or Coleopteran pest populations includes killing the insects by contacting the insects with an effective insect-controlling amount of a polypeptide of the invention.

The present invention also comprises a method for protecting a plant from an insect pest, comprising expressing in a plant or plant cell a nucleotide sequence or expression cassette that encodes an insecticidal polypeptide of the invention. In embodiments, the nucleotide sequence is at least 80%, at least 85%, at least 90%, at least 91%, at least 92%, at least 93%, at least 94%, at least 95%, at least 96%, at least 97%, at least 98%, at least 99%, or is 100% identical to the nucleotide sequence of SEQ ID NO: 1-16 or encodes a polypeptide comprising an amino acid sequence that is at least 80%, at least 85%, at least 90%, at least 91%, at least 92%, at least 93%, at least 94%, at least 95%, at least 96%, at least 97%, at least 98%, at least 99%, or is 100% identical to any of SEQ ID NO: 1-16. In further embodiments, the plant or plant cell produces an insecticidal polypeptide having insecticidal activity against a Lepidopteran and/or Coleopteran pest.

The present invention also comprises a method for increasing yield in a plant comprising growing in a field a plant, or a seed thereof, having stably incorporated into its genome a nucleic acid molecule of an expression cassette of the invention, and wherein said field is infested with a pest against which said polypeptide has insecticidal activity.

Once a desired nucleic acid has been transformed into a particular plant species, it may be propagated in that species or moved into other varieties of the same species, particularly including commercial varieties, using traditional breeding techniques.

In embodiments, a nucleic acid of this invention is expressed in transgenic plants, thus causing the biosynthesis of the corresponding insecticidal protein in the transgenic plants. In this way, transgenic plants with enhanced resistance to insects, particularly corn rootworm, are generated. For their expression in transgenic plants, the nucleic acids of the invention may optionally be modified and optimized. Although in many cases genes from microbial organisms can be expressed in plants at high levels without modification, low expression in transgenic plants may result from microbial nucleic acids having codons that are not preferred in plants. It is known in the art that all organisms have specific preferences for codon usage, and the codons of the nucleic acids described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleic acids that have low GC contents may express poorly in plants due to the existence of ATTTA motifs that may destabilize messages, and AATAAA motifs that may cause inappropriate polyadenylation. In embodiments, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleic acids are screened for the existence of illegitimate splice sites that may cause message truncation. All changes required to be made within the nucleic acids such as those described above can be made using well known techniques of site directed mutagenesis, PCR, and synthetic gene construction, for example, using the methods described in the published patent applications EP 0 385 962, EP 0 359 472, and WO 93/07278.

In one embodiment of the invention a coding sequence for an insecticidal protein of the present invention is made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid might be derived, for example, from known gene sequences from maize. Maize codon usage for 28 genes from maize plants is found in Murray et al., Nucleic Acids Research 17:477-498 (1989), the disclosure of which is incorporated herein by reference.

In this manner, the nucleotide sequences can be optimized for expression in any plant. It is recognized that all or any part of the gene sequence may be optimized or synthetic. That is, synthetic or partially optimized sequences may also be used.

For more efficient initiation of translation, sequences adjacent to the initiating methionine may be modified. For example, they can be modified by the inclusion of sequences known to be effective in plants. Joshi has suggested an appropriate consensus for plants (NAR 15:6643-6653 (1987)) and Clontech suggests a further consensus translation initiator (1993/1994 catalog, page 210). These consensus sequences are suitable for use with the nucleic acids of this invention. In embodiments, the sequences are incorporated into constructions comprising the nucleic acids, up to and including the ATG (whilst leaving the second amino acid unmodified), or alternatively up to and including the GTC subsequent to the ATG (with the possibility of modifying the second amino acid of the transgene).

Expression of the nucleic acids in transgenic plants is driven by promoters that function in plants. The choice of promoter will vary depending on the temporal and spatial requirements for expression, and also depending on the target species. Thus, expression of the nucleic acids of this invention in leaves, in stalks or stems, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleic acids in the desired cell.

In one embodiment promoters are used that are expressed constitutively including the actin or ubiquitin or cmp promoters or the CaMV 35S and 19S promoters. The nucleic acids of this invention can also be expressed under the regulation of promoters that are chemically regulated. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

In another embodiment a category of promoters which is wound inducible can be used. Numerous promoters have been described which are expressed at wound sites and also at the sites of phytopathogen infection. Ideally, such a promoter should only be active locally at the sites of infection, and in this way the insecticidal proteins of the invention only accumulate in cells that need to synthesize the proteins to kill the invading insect pest. Preferred promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Tissue-specific or tissue-preferential promoters useful for the expression of genes encoding insecticidal proteins of the invention in plants, particularly corn, are those which direct expression in root, pith, leaf or pollen, particularly root. Such promoters, e.g. those isolated from PEPC or trpA, are disclosed in U.S. Pat. No. 5,625,136, or MTL, disclosed in U.S. Pat. No. 5,466,785. Both U. S. patents are herein incorporated by reference in their entirety.

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used.

Thus, for example, chemical-regulated promoters can be used to modulate the expression of nucleotide sequences of the invention in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces expression of a nucleotide sequence of the invention, or a chemical-repressible promoter, where application of the chemical represses expression of a nucleotide sequence of the invention.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid (e.g., the PR1a system), steroid steroid-responsive promoters (see, e.g., the glucocorticoid-inducible promoter in Schena et al. (1991) Proc. Natl. Acad. Sci. USA 88, 10421-10425 and McNellis et al. (1998) Plant J. 14, 247-257) and tetracycline-inducible and tetracycline-repressible promoters (see, e.g., Gatz et al. (1991) Mol. Gen. Genet. 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) Plant J. 11:605-612), and ecdysone-inducible system promoters.

Other non-limiting examples of inducible promoters include ABA- and turgor-inducible promoters, the auxin-binding protein gene promoter (Schwob et al. (1993) Plant J. 4:423-432), the UDP glucose flavonoid glycosyl-transferase promoter (Ralston et al. (1988) Genetics 119:185-197), the MPI proteinase inhibitor promoter (Cordero et al. (1994) Plant J. 6:141-150), and the glyceraldehyde-3-phosphate dehydrogenase promoter (Kohler et al. (1995) Plant Mol. Biol. 29:1293-1298; Martinez et al. (1989) J. Mol. Biol. 208:551-565; and Quigley et al. (1989) J. Mol. Evol. 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) Current Opinion Biotechnol. 7:168-172 and Gatz (1997) Annu. Rev. Plant Physiol. Plant Mol. Biol. 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

In further aspects, the nucleotide sequences of the invention can be operably associated with a promoter that is wound inducible or inducible by pest or pathogen infection (e.g., a insect or nematode plant pest). Numerous promoters have been described which are expressed at wound sites and/or at the sites of pest attack (e.g., insect/nematode feeding) or phytopathogen infection. Ideally, such a promoter should be active only locally at or adjacent to the sites of attack, and in this way expression of the nucleotide sequences of the invention will be focused in the cells that are being invaded or fed upon. Such promoters include, but are not limited to, those described by Stanford et al., Mol. Gen. Genet. 215:200-208 (1989), Xu et al. Plant Molec. Biol. 22:573-588 (1993), Logemann et al. Plant Cell 1:151-158 (1989), Rohrmeier and Lehle, Plant Molec. Biol. 22:783-792 (1993), Firek et al. Plant Molec. Biol. 22:129-142 (1993), Warner et al. Plant J. 3:191-201 (1993), U.S. Pat. Nos. 5,750,386, 5,955,646, 6,262,344, 6,395,963, 6,703,541, 7,078,589, 7,196,247, 7,223,901, and U.S. Patent Application Publication 2010043102.

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

Numerous other sequences can be incorporated into expression cassettes described in this invention. These include sequences that have been shown to enhance expression such as intron sequences (e.g. from Adhl and bronze1) and viral leader sequences (e.g. from TMV, MCMV and AMV).

It may be preferable to target expression of the nucleic acids of the present invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleic acid. Many such target sequences are known for the chloroplast and their functioning in heterologous constructions has been shown. The expression of the nucleic acids of the present invention is also targeted to the endoplasmic reticulum or to the vacuoles of the host cells. Techniques to achieve this are well known in the art.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors comprising the nucleic acid molecules of the present invention may also comprise genes (e.g. phosphomannose isomerase; PMI) which provide for positive selection of the transgenic plants as disclosed in U.S. Pat. Nos. 5,767,378 and 5,994,629, herein incorporated by reference. The choice of selectable marker is not, however, critical to the invention.

In embodiments, the nucleic acid can be transformed into the nuclear genome. In another embodiment, a nucleic acid of the present invention is directly transformed into the plastid genome. A major advantage of plastid transformation is that plastids are generally capable of expressing bacterial genes without substantial codon optimization, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome.

Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid of the present invention is inserted into a plastid-targeting vector and transformed into the plastid genome of a desired plant host. Plants homoplastic for plastid genomes containing a nucleic acid of the present invention are obtained, and are preferentially capable of high expression of the nucleic acid.

EXAMPLES

The invention will be further described by reference to the following detailed examples. These examples are provided for the purposes of illustration only, and are not intended to be limiting unless otherwise specified. Standard recombinant DNA and molecular cloning techniques used here are well known in the art and are described by J. Sambrook, et al., Molecular Cloning: A Laboratory Manual, 3d Ed., Cold Spring Harbor, N.Y.: Cold Spring Harbor Laboratory Press (2001); by T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, New York, John Wiley and Sons Inc., (1988), Reiter, et al., Methods in *Arabidopsis* Research, World Scientific Press (1992), and Schultz et al., Plant Molecular Biology Manual, Kluwer Academic Publishers (1998).

Example 1: Identification of a Protein with Insecticidal Activity Against Western Corn Rootworm An insecticidal protein (SEQ ID NO: 1) was identified from Lachnospiraceae bacterium 3_1_57FAA_CT1. An *E. coli*-optimized version of this gene was synthesized (SEQ ID NO: 18) and the gene was cloned into a pET29a vector, creating construct pET29a(Lachb). The pET29a(Lachb) construct was transformed into *E. coli* JM109 (DE3) and protein expression was carried out in ZYP-5052 auto-induction media at 25° C. for 24 hours. Lysates were prepared from these cultures and were tested for bioactivity on Western Corn Rootworm. Briefly, *E. coli* JM109 (DE3) lysates or purified protein were mixed with an equal volume of heated artificial insect diet (Bioserv, Inc., Frenchtown, N.J.) in 1.5 mL centrifuge tubes and then applied to small petri-dishes. After the diet-sample mixture cooled and solidified, 12 WCR larvae were added to each plate. The plates were sealed and maintained at ambient laboratory conditions with regard to temperature, lighting and relative humidity. Lysates from *E. coli* cultures harboring the empty pET29a vector were used as negative controls. Mortality was assessed on day3 and day 6.

As shown in Table 1, lysate from the culture expressing pET29a(Lachb) showed strong bioactivity against WCR. The Lachnospiraceae bacterium 3_1_57FAA_CT1 protein was renamed LachbCRW.

TABLE 1

Insecticidal Activity against Western Corn Rootworm

| Treatment | Day 3 Dead | Day 3 % Mortality | Day 6 Dead | Day 6 % Mortality | Remarks |
|---|---|---|---|---|---|
| 50 mM Tris pH 8.5, 50 mM NaCl | 0 | 0 | 0 | 0 | b |
| JM109/pET29a | 1 | 8 | 1 | 8 | b |
| JM109/pET29a (Lachb) | 7 | 58 | 10 | 83 | s, m |
| JM109/pET29a (Lachb) | 8 | 67 | 10 | 83 | s, m |
| Diet alone | 0 | 0 | 1 | 8 | b | s = small larvae,
m = medium larvae,
b = big larvae,
vb = very big larvae

Example 2: Variants of LachbCRW Possess Insecticidal Activity Against Western Corn Rootworm Mutations were introduced into LachbCRW and the protein stability and insecticidal activity was assayed. LachbCRW residue Y164 was mutated to W (SEQ ID NO: 2) and F (SEQ ID NO: 3). Lysates of these constructs were analyzed by Bio-Rad Experion analysis, and it was determined that LachbCRW Y164W variant produced 3.5-fold more soluble protein as compared to the wild type protein in *E. coli* JM109 (DE3) (21% of total protein compared to 6% total protein). A second mutation (I169L) was combined with Y164W (SEQ ID NO: 4) and the protein was produced and purified and used to determine insecticidal activity.

A bacterial cell lysate was collected from two liters of JM109 (DE3) cells harboring pET29a(LachbCRW Y164W/ I169L) that were grown in ZYP-5052 auto-induction media. The LachbCRW Y164W/I169L protein was then purified and found to be 85-90% pure. The purified protein was tested for efficacy against WCR in a diet-incorporation bioassay, performed as described in Example 1, except mortality was assessed on day 4 and day 6. As shown in Table 2, the purified protein demonstrates strong activity against WCR.

TABLE 2

Insecticidal Activity of LachbCRW Y164W/I169L against WCR

| LachbCRW Y164W/I169L (µg/mL) | Day 4 Dead | Day 4 % Mortality | Day 4 Remarks | Day 6 Dead | Day 6 % Mortality | Day 6 Remarks |
|---|---|---|---|---|---|---|
| 1× PBS only | 0 | 0 | b | 0 | 8 | b |
| 500 | 7 | 58 | s, m | 12 | 100 | s |
| 375 | 7 | 58 | s, m | 12 | 100 | s |
| 250 | 8 | 67 | s, m | 11 | 92 | s |
| 200 | 9 | 75 | s, m | 12 | 100 | s |
| 150 | 9 | 75 | s, m | 11 | 92 | s |
| 100 | 10 | 83 | s, m | 12 | 100 | s |
| 50 | 9 | 75 | s, m | 9 | 75 | s, m, b |
| Diet alone | 0 | 0 | b | 0 | 0 | b | s = small larvae,
m = medium larvae,
b = big larvae,
vb = very big larvae

Several other mutations were combined with Y164W to generate other double mutants of LachbCRW, namely Y164W/Y385W (SEQ ID NO: 5), Y164W/Y400W (SEQ ID NO: 6), Y164W/Y402W (SEQ ID NO: 7), and Y164W/Y431W (SEQ ID NO: 8). Lysates of JM109 (DE3) expressing the LachbCRW double mutants were made and tested for bioactivity to WCR using diet-incorporation assays, performed as described in Example 1 except 10 larvae were added to each plate and mortality was assessed at 120 hours (5 days) only. As shown in Table 3, all the double mutants showed bioactivity against WCR.

TABLE 3

Insecticidal Activity of LachbCRW variants against WCR

| Treatment | Dead | % Mortality | Remarks |
|---|---|---|---|
| 50 mM potassium phosphate pH 7.0, 50 mM NaCl | 0 | 0% | b |
| JM109/pet29a | 4 | 40% | b |
| JM109/LachbCRW Y164W Y385W | 10 | 100% | s |
| JM109/LachbCRW Y164W Y400W | 10 | 100% | s |
| JM109/LachbCRW Y164W Y402W | 10 | 100% | s |
| JM109/LachbCRW Y164W Y431W | 10 | 100% | s |
| JM109/LachbCRW Y164W | 10 | 100% | s | s = small larvae,
m = medium larvae,
b = big larvae,
vb = very big larvae

Other LachbCRW mutants were generated and tested for bioactivity to WCR; these mutants include Y164F (SEQ ID NO: 3), Y164F/I169L (SEQ ID NO: 9), and Y164F/T166S (SEQ ID NO: 10). Lysates of JM109 (DE3) expressing the LachbCRW double mutants were made and tested for bioactivity to WCR using diet-incorporation assays at a concentration of 0.25 mg Lachb protein/ml, performed similarly as described in Example 1 except mortality was assessed at day 5 and day 7. The WCR bioactivity data for these mutants is presented in Table 4.

TABLE 4

Insecticidal Activity of LachbCRW variants against WCR

| Treatment | Day 5 % mortality | Day 5 Remarks | Day 7 % mortality | Day 7 Remarks |
|---|---|---|---|---|
| 50 mM Tris 8.5, 50 mM NaCl | 8 | b | 8 | b |
| JM109/pET29 empty | 0 | b | 13 | b |
| JM109/LachbCRW-wt 0.25 mg/ml | 33 | s, m, b | 57 | s, m, b |
| JM109/LachbCRW Y164W 0.25 mg/ml | 50 | s, m, b | 77 | s, m, b |
| JM109/LachbCRW Y164F 0.25 mg/ml | 27 | s, m, b | 36 | s, m, b |
| JM109/LachbCRW Y164F/I169L 0.25 mg/ml | 62 | s, m, b | 86 | s, m, b |
| JM109/LachbCRW Y164F/T166S 0.25 mg/ml | 60 | s, m, b | 80 | s, m, b |
| Diet alone | 0 | b | 0 | b | s = small larvae,
m = medium larvae,
b = big larvae,
vb = very big larvae

Example 3: LachbCRW Possesses Insecticidal Activity Against Northern Corn Rootworm LachbCRW variant Y164W/I169L was purified as in Example 2 and was tested for efficacy against Northern Corn Rootworm (NCR) in a diet-incorporation assay, performed essentially as described in Example 1, except mortality was assessed on day 3 and day 7. LachbCRW Y164W/I169L was tested at two different concentrations, 0.6 mg/mL and 0.3 mg/mL. The negative control had only 1×PBS. As shown in Table 5, LachbCRW Y164W/I169L variant demonstrates insecticidal activity against NCR.

TABLE 5

Insecticidal Activity of LachbCRW variant against NCR

| Treatment | Day 3 Dead | Day 3 Mort % | Day 3 Remarks | Day 7 Dead | Day 7 Mort % | Day 7 Remarks |
|---|---|---|---|---|---|---|
| 1× PBS | 2 | 17% | mb | 3 | 25% | mb |
| 0.6 mg/mL | 8 | 67% | m | 8 | 67% | m |
| 0.3 mg/mL | 2 | 17% | sm | 4 | 33% | sm | s = small larvae,
sm = small/medium larvae,
m = medium larvae,
mb = medium/big larvae,
b = big larvae,
vb = very big larvae

Example 4: LachbCRW Possesses Insecticidal Activity Against Southern Corn Rootworm LachbCRW variant Y164W/I169L was purified as in Example 2 and was tested for efficacy against Southern Corn Rootworm (SCR) in a diet-incorporation assay, performed essentially as described in Example 1, except mortality was assessed on days 2, 5, and 7. LachbCRW Y164W/I169L was tested at two different concentrations, 0.5 mg/mL and 0.25 mg/mL. The negative control had only 1×PBS. As shown in Table 6, LachbCRW Y164W/I169L variant demonstrates some insecticidal activity against SCR.

TABLE 6

Insecticidal Activity of LachbCRW variant against SCR

| Treatment | Day 2 Dead | Mort % | Day 5 Dead | Mort %y | Day 8 Dead | Mort % | Remarks |
|---|---|---|---|---|---|---|---|
| 1× PBS | 0 | 0% | 0 | 0% | 0 | 0% | b/vb |
| 0.5 mg/ml | 0 | 0% | 0 | 0% | 2 | 17% | m/b |
| 0.25 mg/ml | 0 | 0% | 0 | 0% | 2 | 17% | m/b | s = small larvae,
sm = small/medium larvae,
m = medium larvae,
mb = medium/big larvae,
b = big larvae,
vb = very big larvae

Example 5: LachbCRW Possesses Insecticidal Activity Against Cry Resistant Western Corn Rootworm To determine if LachbCRW toxicity is through a mode of action separate from Cry proteins, LachbCRW variant Y164W/I169L was purified as in Example 2 and was tested for efficacy against a strain of WCR that is resistant to the mCry3A toxin (mCry3A-R) and against a strain of WCR that is resistant to the eCry3.1Ab toxin (eCry3.1Ab-R). Diet-incorporation assay were performed essentially as described in Example 1, except mortality was assessed on day 4 and day 7. LachbCRW Y164W/I169L was tested at two different concentrations, 0.6 mg/mL and 0.3 mg/mL. The negative control had only 1×PBS. WCR that is not resistant to mCry3A or eCry3.1Ab (sus) was also assayed. As shown in Table 7, LachbCRW Y164W/I169L variant demonstrates insecticidal activity against Cry resistant WCR strains.

TABLE 7

Insecticidal Activity of LachbCRW variant against Cry-R WCR

| Treatment | Day 4 Dead | Mort % | Remarks | Day 6 Dead | Mort % | Remarks |
|---|---|---|---|---|---|---|
| sus, 0.6 mg/mL | 2 | 17% | 10 m | 5 | 42% | 7 m |
| sus, 0.3 mg/mL | 3 | 25% | 9 m | 7 | 58% | 5 m |
| sus, 1× PBS | 0 | 0% | 12 mb | 1 | 8% | 11 mb |
| mCry3A-R, 0.6 mg/mL | 3 | 25% | 9 m | 10 | 83% | 2 m |
| mCry3A-R, 0.3 mg/mL | 0 | 0% | 12 m | 4 | 33% | 8 m |
| mCry3A-R, 1x PBS | 0 | 0% | 12 mb | 3 | 25% | 9 mb |
| eCry3.1Ab-R, 0.6 mg/mL | 1 | 8% | 11 m | 4 | 33% | 8 m |
| eCry3.1Ab-R, 0.3 mg/mL | 0 | 0% | 12 m | 2 | 17% | 10 mb |
| eCry3.1Ab-R, 1× PBS | 0 | 0% | 12 mb | 0 | 0% | 12 mb | s = small larvae,
sm = small/medium larvae,
m = medium larvae,
mb = medium/big larvae,
b = big larvae,
vb = very big larvae

Example 6: LachbCRW does not Possess Insecticidal Activity Against Fall Armyworm Lysates of JM109 (DE3)/LachbCRW-wild type were tested for bioactivity to fall armyworm (FAW) in a diet-overlay bioassay, as shown in Table 5. Briefly, *E. coli* JM109 (DE3) lysates were applied to the surface of an artificial insect diet (Bioserv, Inc., Frenchtown, N.J.) in small petri-dishes. After the diet surface dried, twelve FAW larvae were added to each plate. The plates were sealed and maintained at ambient laboratory conditions with regard to temperature, lighting and relative humidity. Lysates from cultures harboring the empty pET29a vector were used as negative controls. For bioassay experiments utilizing purified protein, 1×PBS was used as the negative control. A positive-control group consisted of larvae exposed to *E. coli* B121* (DE3) lysates expressing Vip3D. LachbCRW-wild type was not active to FAW (Table 8).

TABLE 8

Insecticidal Activity of LachbCRW against Fall Armyworm

| Treatment | Day 3 % mortality | Remarks | Day 6 % mortality | Remarks |
|---|---|---|---|---|
| 50 mM Tris 8.5, 50 mM NaCl | 0 | f | 0 | f |
| Jm109/pET29a | 0 | f | 0 | f |
| Jm109/LachbCRW | 0 | f | 0 | f |
| Vip3D (+) | 83 | nf | 92 | nf |
| Diet alone | 0 | f | 0 | f | f = feeding,
mf = medium feeding,
vsf = very slightly feeding,
nf = no feeding,
sf = slightly feeding

Example 7: LachbCRW Possesses Insecticidal Activity Against Some Lepidopterans Lysates of JM109 (DE3)/LachbCRW-wild type were tested for bioactivity on a panel of Lepidopteran insect pests using diet-overlay bioassays. European corn borer (ECB), black cutworm (BCW), corn earworm (CEW), sugar cane borer (SCB), southwestern corn borer (SWCB), soybean looper (sbl), velvet bean caterpillar (VBC), and tobacco budworm (TBW) were each tested for LachbCRW Y164W/I169L insecticidal activity by a diet-based assay similar to that of Example 6. 12 larvae were tested for each experiment, at a LachbCRW protein concentration of 1 μg/cm². *B. thuringiensis* strains C0756 (which has multiple Lepidopteran-active toxins) and AB227 (which is an acrystalliferous strain and contains no Lepidopteran-active toxins) were included as positive and negative controls, respectively. Insect diet without anything added and with 1×PBS added were also included as negative controls. As in Example 6, lysates from bacterial JM109 cultures harboring the empty pET29 vector were also used as negative controls.

TABLE 9

Insecticidal Activity of LachbCRW against Lepidopterans

| Insect | Diet | C0756 | AB227 | 1xPBS | LachbCRW/JM109 | pET29-VC/JM109 |
|---|---|---|---|---|---|---|
| ECB | 0% | 100% | 0% | 0% | 0% | 0% |
| BCW | 0% | 100% | 0% | 0% | 17% | 8% |
| FAW | 0% | 83% | 8% | 0% | 0% | 8% |
| CEW | 0% | 100% | 0% | 0% | 0% | 8% |
| SCB | 0% | 100% | 8% | 0% | 8% | 0% |
| SWCB | 0% | 100% | 17% | 8% | 17% | 0% |
| SBL | 0% | 0% | 0% | 8% | 0% | 0% |
| VBC | 0% | 100% | 0% | 0% | 0% | 17% |
| TBW | 8% | 100% | 0% | 0% | 0% | 0% |

Example 8: Transformation of Maize with LachbCRW Variant

Construct 23075 was generated for LachbCRW maize transformation experiments. The LachbCRW expression cassette contains the Y164W/I169L substitutions. Construct 23075 comprises an expression cassette comprising cPMI, which encodes for the selectable marker phosphomannose isomerase (PMI)) that confers an ability to metabolize mannose (U.S. Pat. Nos. 5,767,378 and 5,994,629), and an expression cassette comprising a maize codon-optimized nucleotide sequence encoding for LachbCRW Y164W/I169L (SEQ ID NO: 36).

Construct 23075 was transformed into *Agrobacterium tumefaciens* using standard molecular biology techniques known to those skilled in the art. To prepare the Agrobacteria for transformation, cells were cultured in liquid YPC media at 28° C. and 220 rpm overnight. *Agrobacterium* transformation of immature maize embryos was performed essentially as described in Negrotto et al., 2000, (Plant Cell Reports 19: 798-803). For this example, all media constituents are essentially as described in Negrotto et al., supra. However, various media constituents known in the art may be substituted.

Following transformation, selection, and regeneration, plants were assayed for the presence of the pmi gene and the Lachb Y164W/I169L coding sequence (SEQ ID NO: 36) using TaqMan® analysis. Plants were also tested for the presence of the vector backbone. Plants negative for the vector backbone and comprising one copy of the transgene from construct 23075 were transferred to the greenhouse and tested for resistance to WCR.

Example 9: Maize Plants Expressing LachbCRW Variant have Insecticidal Activity Against WCR Samples of maize root tissue were taken when LachbCRW-expressing maize events reached the V3-V4 stage. Maize root tissue was placed in a petri dish and then infected with 12 WCR larvae. Root tissue was evaluated for feeding holes (FH) and scarring damage at day 5. Root tissue from non-transformed (null) maize served as the negative control. Expression of LachbCRW Y164W/I169L in maize events provided protection from WCR in a majority of the LachbCRW transgenic root tissue when compared to the null sample root tissue (Table 10).

TABLE 10

Insecticidal Activity of Transgenic LachbCRW Y164W/1169L Maize against WCR

| Plant | LachbCRW ELISA (ng/mg) | | |
|---|---|---|---|
| ID | Leaf | Root | Feeding Damage |
| 8521 | 864.54 | 776.99 | 4 feeding holes (FH) light scarring |
| 8520 | 529.54 | 1633.03 | 4 FH, light scarring |
| 8519 | 293.15 | 1902.74 | 3 FH |
| 8517 | 635.14 | 1147.71 | 6 FH, light scarring |
| 8514 | 517.47 | 1298.64 | 10 FH, medium scarring |
| 8511 | 250.05 | 693.66 | 3 FH, light/medium scarring |
| 8509 | 650.78 | 335.53 | 4 FH, light scarring |
| 8506 | 136.99 | 634.50 | 10 FH, light scarring |
| 8503 | 474.43 | 970.18 | 5 FH |
| 8499 | 763.36 | 1284.51 | 4 FH |
| 8498 | 551.89 | 1229.99 | 9 FH |
| 8496 | 408.74 | 1082.70 | 21 FH, medium/heavy scarring, mite |
| 8494 | 288.14 | 833.00 | 6 FH, light scarring |
| 8488 | 112.18 | 637.88 | at least 10 FH, chewed heavily in places, all larvae dead |
| 8486 | 143.07 | 633.53 | 7 FH, medium/heavy scarring |
| 8482 | 348.24 | 1015.49 | 11 FH, heavy scarring |
| 8480 | 389.64 | 887.25 | 3 FH |
| 8478 | 330.35 | 1189.76 | 3 FH, one end of root chewed |
| 8477 | 186.19 | 347.17 | 10 FH, light scarring |
| 8474 | 420.58 | 1740.87 | 5 FH, light scarring |
| 8473 | 499.89 | 1119.01 | 5 FH |
| 8469 | 180.07 | 663.65 | 14 FH, heavy scarring |
| 8466 | 226.13 | 835.63 | 7 FH, one end of root chewed heavily |
| 8461 | 612.35 | 534.69 | 3 FH, light scarring |
| 8459 | 290.77 | 698.30 | 5 FH, all larvae dead |
| 8457 | 782.89 | 703.65 | 6 FH, light scarring |
| 8456 | 191.58 | 822.94 | 7 FH, light scarring |
| 8455 | 500.23 | 1323.00 | root completely full of holes, worse than null, all larvae dead |
| 8453 | 359.83 | 1240.18 | 4 FH, root chewed to point of breaking in 2-3 spots, all larvae dead |
| 8450 | 575.22 | 1251.08 | 9 FH, light/medium scarring |
| null | | | 15 FH, medium/heavy scarring |

FH = feeding holes

Example 10: LachbCRW Variant in Combination with an Interfering RNA have Insecticidal Activity Against WCR LachbCRW and/or a LachbCRW variant, for example LachbCRW variant Y164W/I169L, was purified as in Example 2 and dsRNA against an essential target was prepared. The dsRNA and purified protein were tested in combination for efficacy against WCR in a diet-incorporation assay, performed essentially as described in Example 1. Prophetically, the combination of the dsRNA with the LachbCRW or with the LachbCRW variant, for example LachbCRW variant Y164W/I169L, has insecticidal activity against WCR.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. A plant cell comprising an expression cassette comprising a promoter operably linked to a heterologous nucleic acid molecule comprising a nucleotide sequence that encodes a polypeptide, wherein the amino acid sequence of the polypeptide comprises SECS ID NO: 1.

2. A transgenic plant comprising a nucleic acid molecule which confers enhanced insect resistance, wherein said nucleic acid molecule comprises an expression cassette comprising a promoter operably linked to a heterologous nucleic acid molecule comprising a nucleotide sequence that encodes a polypeptide, wherein the amino acid sequence of the polypeptide comprises SEQ ID NO: 1.

3. The transgenic plant of claim 2, wherein said plant is a monocotyledonous plant.

4. The transgenic plant of claim 3, wherein said plant is maize.

5. The transgenic plant of claim 2, wherein the nucleic acid molecule comprises a nucleotide sequence which encodes for at least one additional desired trait, wherein the desired trait is selected from the group consisting of insect resistance, abiotic stress tolerance, male sterility, herbicide resistance, bacterial disease resistance, fungal disease resistance, viral disease resistance, nematode resistance, modified fatty acid metabolism, modified carbohydrate metabolism, production of a commercially valuable enzyme or metabolite, improved nutritional value, improved performance in an industrial process and altered reproductive capability.

6. A method of producing a plant having enhanced insect resistance as compared to a control plant or plant part, the method comprising crossing a first parent plant with a second parent plant, wherein at least the first parent plant is the transgenic plant of claim 2; and producing a progeny generation, wherein the progeny generation comprises at least one plant that possesses the expression cassette and that exhibits enhanced insect resistance as compared to a control plant.

7. The method of claim 6, wherein the plant is a monocotyledonous plant.

8. The method of claim 7; wherein the plant is maize.

9. A method for controlling a lepidopteran or coleopteran pest population, the method comprising contacting said population with an effective insect-controlling amount of a polypeptide with insecticidal activity, wherein the polypeptide comprises the amino acid sequence of SEQ ID NO: 1.

* * * * *

SEQUENCE LISTING

```
<160> NUMBER OF SEQ ID NOS: 37

<210> SEQ ID NO 1
<211> LENGTH: 482
```

```
<212> TYPE: PRT
<213> ORGANISM: Unknown
<220> FEATURE:
<223> OTHER INFORMATION: Lachnospiraceae bacterium.

<400> SEQUENCE: 1
```

| | | | | | | | | | | | | | | | |
|---|---|---|---|---|---|---|---|---|---|---|---|---|---|---|---|
| Met | Ser | Asn | Ile | Asp | Leu | Leu | Lys | Leu | Gln | Ser | Leu | Leu | Asp | Asp | His |
| 1 | | | | 5 | | | | | 10 | | | | | 15 | |
| Arg | His | Tyr | Leu | Leu | Gln | Gly | Tyr | Asn | Val | Val | Ser | Asn | Pro | Tyr | Leu |
| | | | 20 | | | | | 25 | | | | | 30 | | |
| Arg | Thr | Glu | Asp | Ile | Gln | Met | Ser | Asn | Thr | Ile | Leu | Asp | Lys | Asp | Lys |
| | | 35 | | | | | 40 | | | | | 45 | | | |
| Leu | Asn | Glu | Lys | Phe | Pro | Gly | Asn | Ser | Phe | Tyr | Asn | Tyr | Val | Ser | Gly |
| 50 | | | | | 55 | | | | | 60 | | | | | |
| Asn | Glu | Thr | Gly | Ser | Ile | Ser | Glu | Thr | Tyr | Ala | Gly | Asn | Thr | Leu | Tyr |
| 65 | | | | | 70 | | | | | 75 | | | | | 80 |
| Glu | Met | Glu | Asn | Ser | Phe | Gly | Thr | Lys | Asn | Thr | Ile | Ala | Tyr | Asn | Ser |
| | | | | 85 | | | | | 90 | | | | | 95 | |
| Val | Ala | Leu | Asn | Ala | Ser | Leu | Ser | Ala | Asp | Tyr | Gln | Thr | Gly | Asn | Ser |
| | | | 100 | | | | | 105 | | | | | 110 | | |
| Ile | Leu | Asp | Asn | Asn | Ile | Phe | Leu | Lys | Gln | Tyr | Gln | Ala | His | Val | Leu |
| | | | 115 | | | | | 120 | | | | | 125 | | |
| Gly | His | Ile | Tyr | Ser | Arg | Gly | Asp | Val | Ser | Asp | Leu | Arg | Glu | Cys | Leu |
| 130 | | | | | 135 | | | | | 140 | | | | | |
| Asp | Ala | His | Phe | Arg | Glu | Asp | Leu | Glu | Asn | Met | Glu | Pro | Arg | Lys | Leu |
| 145 | | | | | 150 | | | | | 155 | | | | | 160 |
| Phe | Phe | Lys | Tyr | Gly | Thr | His | Leu | Ile | Arg | Asp | Phe | Ser | Val | Gly | Gly |
| | | | | 165 | | | | | 170 | | | | | 175 | |
| Cys | Ile | Met | Leu | Asp | Met | Arg | Tyr | His | Asn | His | Met | His | Lys | Thr | Val |
| | | | 180 | | | | | 185 | | | | | 190 | | |
| Gln | Gln | Val | Ser | Ala | Asp | Ala | Ala | Ala | Tyr | Ser | Gly | Leu | Ser | Leu | |
| | | | 195 | | | | | 200 | | | | | 205 | | |
| Asp | Ser | Ser | Thr | Ser | Ala | Tyr | Lys | Asn | Ala | Val | Ser | Phe | Tyr | Gln | Asn |
| | 210 | | | | | 215 | | | | | 220 | | | | |
| Val | Ser | Val | Arg | Ile | Arg | Ser | Val | Gly | Gly | Asn | Ser | Phe | Ser | Ala | Phe |
| 225 | | | | | 230 | | | | | 235 | | | | | 240 |
| Ser | Val | Ser | Asp | Phe | Asn | Ser | Gln | Ser | Lys | Ala | Trp | Met | Asp | Ser | Leu |
| | | | | 245 | | | | | 250 | | | | | 255 | |
| Ala | Asp | Lys | Ala | Val | Pro | Phe | Arg | Ile | Asn | Arg | Asn | Gly | Ser | Leu | Pro |
| | | | 260 | | | | | 265 | | | | | 270 | | |
| Ile | Trp | Glu | Leu | Thr | Ser | Asn | Ala | Ala | Arg | Ala | Lys | Thr | Leu | Glu | Lys |
| | | | | 275 | | | | | 280 | | | | | 285 | |
| Glu | Phe | Tyr | Leu | Tyr | Asn | Ile | Asp | Val | Leu | Asp | Glu | Val | Lys | Ala | Asn |
| | | 290 | | | | | 295 | | | | | 300 | | | |
| Ile | Pro | Phe | Ile | Thr | Asp | Leu | Arg | Val | Glu | Ile | Arg | Asp | Lys | Asp | Asn |
| 305 | | | | | 310 | | | | | 315 | | | | | 320 |
| Ile | Arg | Ser | Val | Cys | Pro | Glu | Asn | Trp | Tyr | Val | Ala | Gln | Met | Asn | Pro |
| | | | | 325 | | | | | 330 | | | | | 335 | |
| Gly | Thr | Leu | Ser | Ala | Tyr | Asp | Ile | Asp | Leu | Asn | Lys | Gly | Ser | Gly | Gly |
| | | | 340 | | | | | 345 | | | | | 350 | | |
| Lys | Tyr | Ile | Tyr | Leu | Leu | Tyr | Arg | Phe | Gly | Thr | Asn | Gln | Lys | Asp | Arg |
| | | 355 | | | | | 360 | | | | | 365 | | | |
| Ile | Thr | Asp | Ile | Lys | Ile | Leu | Met | Gly | Arg | Asn | Thr | Thr | Leu | Gly | Gly |
| | 370 | | | | | 375 | | | | | 380 | | | | |

-continued

Tyr Thr Arg Ile Asp Ala Asp Leu Asn Thr Gly Ser Gly Gly Glu Tyr
385                 390                 395                 400

Ile Tyr Leu Ala Tyr Lys Lys Glu Asp Asn Lys Glu Lys Asp Gly Ile
            405                 410                 415

Tyr Gly Leu Gly Thr Thr Glu Gln Ser Ser Phe Thr Asp Asn Tyr Trp
            420                 425                 430

Arg Met Ala Lys Asp Gln Asn Asn Asn Leu Ala Asp Leu Asn Lys Gly
        435                 440                 445

Ala Gly Gly Leu Phe Ile Tyr Leu Leu Thr Tyr Arg Glu Lys Tyr Leu
    450                 455                 460

Asp Glu Ile Glu Arg Glu Lys Arg Glu Leu Gln Ala Leu Thr Asp Ser
465                 470                 475                 480

Leu Lys

<210> SEQ ID NO 2
<211> LENGTH: 482
<212> TYPE: PRT
<213> ORGANISM: Artificial Sequence
<220> FEATURE:
<223> OTHER INFORMATION: LachbCRW Y164W.

<400> SEQUENCE: 2

Met Ser Asn Ile Asp Leu Leu Lys Leu Gln Ser Leu Leu Asp Asp His
1               5                   10                  15

Arg His Tyr Leu Leu Gln Gly Tyr Asn Val Val Ser Asn Pro Tyr Leu
            20                  25                  30

Arg Thr Glu Asp Ile Gln Met Ser Asn Thr Ile Leu Asp Lys Asp Lys
        35                  40                  45

Leu Asn Glu Lys Phe Pro Gly Asn Ser Phe Tyr Asn Tyr Val Ser Gly
    50                  55                  60

Asn Glu Thr Gly Ser Ile Ser Glu Thr Tyr Ala Gly Asn Thr Leu Tyr
65                  70                  75                  80

Glu Met Glu Asn Ser Phe Gly Thr Lys Asn Thr Ile Ala Tyr Asn Ser
                85                  90                  95

Val Ala Leu Asn Ala Ser Leu Ser Ala Asp Tyr Gln Thr Gly Asn Ser
            100                 105                 110

Ile Leu Asp Asn Asn Ile Phe Leu Lys Gln Tyr Gln Ala His Val Leu
        115                 120                 125

Gly His Ile Tyr Ser Arg Gly Asp Val Ser Asp Leu Arg Glu Cys Leu
    130                 135                 140

Asp Ala His Phe Arg Glu Asp Leu Glu Asn Met Glu Pro Arg Lys Leu
145                 150                 155                 160

Phe Phe Lys Trp Gly Thr His Leu Ile Arg Asp Phe Ser Val Gly Gly
                165                 170                 175

Cys Ile Met Leu Asp Met Arg Tyr His Asn His Met His Lys Thr Val
            180                 185                 190

Gln Gln Val Ser Ala Asp Ala Ala Ala Tyr Ser Gly Leu Ser Leu
        195                 200                 205

Asp Ser Ser Thr Ser Ala Tyr Lys Asn Ala Val Ser Phe Tyr Gln Asn
    210                 215                 220

Val Ser Val Arg Ile Arg Ser Val Gly Gly Asn Ser Phe Ser Ala Phe
225                 230                 235                 240

Ser Val Ser Asp Phe Asn Ser Gln Ser Lys Ala Trp Met Asp Ser Leu
                245                 250                 255

Ala Asp Lys Ala Val Pro Phe Arg Ile Asn Arg Asn Gly Ser Leu Pro

```
                260                 265                 270
Ile Trp Glu Leu Thr Ser Asn Ala Ala Arg Ala Lys Thr Leu Glu Lys
            275                 280                 285

Glu Phe Tyr Leu Tyr Asn Ile Asp Val Leu Asp Glu Val Lys Ala Asn
        290                 295                 300

Ile Pro Phe Ile Thr Asp Leu Arg Val Glu Ile Arg Asp Lys Asp Asn
305                 310                 315                 320

Ile Arg Ser Val Cys Pro Glu Asn Trp Tyr Val Ala Gln Met Asn Pro
                325                 330                 335

Gly Thr Leu Ser Ala Tyr Asp Ile Asp Leu Asn Lys Gly Ser Gly Gly
            340                 345                 350

Lys Tyr Ile Tyr Leu Leu Tyr Arg Phe Gly Thr Asn Gln Lys Asp Arg
        355                 360                 365

Ile Thr Asp Ile Lys Ile Leu Met Gly Arg Asn Thr Thr Leu Gly Gly
        370                 375                 380

Tyr Thr Arg Ile Asp Ala Asp Leu Asn Thr Gly Ser Gly Gly Glu Tyr
385                 390                 395                 400

Ile Tyr Leu Ala Tyr Lys Lys Glu Asp Asn Lys Glu Lys Asp Gly Ile
                405                 410                 415

Tyr Gly Leu Gly Thr Thr Glu Gln Ser Ser Phe Thr Asp Asn Tyr Trp
            420                 425                 430

Arg Met Ala Lys Asp Gln Asn Asn Asn Leu Ala Asp Leu Asn Lys Gly
        435                 440                 445

Ala Gly Gly Leu Phe Ile Tyr Leu Leu Thr Tyr Arg Glu Lys Tyr Leu
        450                 455                 460

Asp Glu Ile Glu Arg Glu Lys Arg Glu Leu Gln Ala Leu Thr Asp Ser
465                 470                 475                 480

Leu Lys

<210> SEQ ID NO 3
<211> LENGTH: 482
<212> TYPE: PRT
<213> ORGANISM: Artificial Sequence
<220> FEATURE:
<223> OTHER INFORMATION: Lachnospiraceae spp.

<400> SEQUENCE: 3

Met Ser Asn Ile Asp Leu Leu Lys Leu Gln Ser Leu Leu Asp Asp His
1               5                   10                  15

Arg His Tyr Leu Leu Gln Gly Tyr Asn Val Val Ser Asn Pro Tyr Leu
            20                  25                  30

Arg Thr Glu Asp Ile Gln Met Ser Asn Thr Ile Leu Asp Lys Asp Lys
        35                  40                  45

Leu Asn Glu Lys Phe Pro Gly Asn Ser Phe Tyr Asn Tyr Val Ser Gly
    50                  55                  60

Asn Glu Thr Gly Ser Ile Ser Glu Thr Tyr Ala Gly Asn Thr Leu Tyr
65                  70                  75                  80

Glu Met Glu Asn Ser Phe Gly Thr Lys Asn Thr Ile Ala Tyr Asn Ser
                85                  90                  95

Val Ala Leu Asn Ala Ser Leu Ser Ala Asp Tyr Gln Thr Gly Asn Ser
            100                 105                 110

Ile Leu Asp Asn Asn Ile Phe Leu Lys Gln Tyr Gln Ala His Val Leu
        115                 120                 125

Gly His Ile Tyr Ser Arg Gly Asp Val Ser Asp Leu Arg Glu Cys Leu
    130                 135                 140
```

Asp Ala His Phe Arg Glu Asp Leu Glu Asn Met Glu Pro Arg Lys Leu
145                 150                 155                 160

Phe Phe Lys Phe Gly Thr His Leu Ile Arg Asp Phe Ser Val Gly Gly
            165                 170                 175

Cys Ile Met Leu Asp Met Arg Tyr His Asn His Met His Lys Thr Val
            180                 185                 190

Gln Gln Val Ser Ala Asp Ala Ala Ala Tyr Ser Gly Leu Ser Leu
        195                 200                 205

Asp Ser Ser Thr Ser Ala Tyr Lys Asn Ala Val Ser Phe Tyr Gln Asn
        210                 215                 220

Val Ser Val Arg Ile Arg Ser Val Gly Gly Asn Ser Phe Ser Ala Phe
225                 230                 235                 240

Ser Val Ser Asp Phe Asn Ser Gln Ser Lys Ala Trp Met Asp Ser Leu
            245                 250                 255

Ala Asp Lys Ala Val Pro Phe Arg Ile Asn Arg Asn Gly Ser Leu Pro
            260                 265                 270

Ile Trp Glu Leu Thr Ser Asn Ala Ala Arg Ala Lys Thr Leu Glu Lys
            275                 280                 285

Glu Phe Tyr Leu Tyr Asn Ile Asp Val Leu Asp Glu Val Lys Ala Asn
        290                 295                 300

Ile Pro Phe Ile Thr Asp Leu Arg Val Glu Ile Arg Asp Lys Asp Asn
305                 310                 315                 320

Ile Arg Ser Val Cys Pro Glu Asn Trp Tyr Val Ala Gln Met Asn Pro
            325                 330                 335

Gly Thr Leu Ser Ala Tyr Asp Ile Asp Leu Asn Lys Gly Ser Gly Gly
            340                 345                 350

Lys Tyr Ile Tyr Leu Leu Tyr Arg Phe Gly Thr Asn Gln Lys Asp Arg
        355                 360                 365

Ile Thr Asp Ile Lys Ile Leu Met Gly Arg Asn Thr Thr Leu Gly Gly
        370                 375                 380

Tyr Thr Arg Ile Asp Ala Asp Leu Asn Thr Gly Ser Gly Gly Glu Tyr
385                 390                 395                 400

Ile Tyr Leu Ala Tyr Lys Lys Glu Asp Asn Lys Glu Lys Asp Gly Ile
            405                 410                 415

Tyr Gly Leu Gly Thr Thr Glu Gln Ser Ser Phe Thr Asp Asn Tyr Trp
            420                 425                 430

Arg Met Ala Lys Asp Gln Asn Asn Asn Leu Ala Asp Leu Asn Lys Gly
            435                 440                 445

Ala Gly Gly Leu Phe Ile Tyr Leu Leu Thr Tyr Arg Glu Lys Tyr Leu
        450                 455                 460

Asp Glu Ile Glu Arg Glu Lys Arg Glu Leu Gln Ala Leu Thr Asp Ser
465                 470                 475                 480

Leu Lys

<210> SEQ ID NO 4
<211> LENGTH: 482
<212> TYPE: PRT
<213> ORGANISM: Artificial Sequence
<220> FEATURE:
<223> OTHER INFORMATION: Lachnospiraceae spp.

<400> SEQUENCE: 4

Met Ser Asn Ile Asp Leu Leu Lys Leu Gln Ser Leu Leu Asp Asp His
1               5                   10                  15

```
Arg His Tyr Leu Leu Gln Gly Tyr Asn Val Val Ser Asn Pro Tyr Leu
             20                  25                  30

Arg Thr Glu Asp Ile Gln Met Ser Asn Thr Ile Leu Asp Lys Asp Lys
         35                  40                  45

Leu Asn Glu Lys Phe Pro Gly Asn Ser Phe Tyr Asn Tyr Val Ser Gly
     50                  55                  60

Asn Glu Thr Gly Ser Ile Ser Glu Thr Tyr Ala Gly Asn Thr Leu Tyr
 65                  70                  75                  80

Glu Met Glu Asn Ser Phe Gly Thr Lys Asn Thr Ile Ala Tyr Asn Ser
                 85                  90                  95

Val Ala Leu Asn Ala Ser Leu Ser Ala Asp Tyr Gln Thr Gly Asn Ser
            100                 105                 110

Ile Leu Asp Asn Asn Ile Phe Leu Lys Gln Tyr Gln Ala His Val Leu
        115                 120                 125

Gly His Ile Tyr Ser Arg Gly Asp Val Ser Asp Leu Arg Glu Cys Leu
    130                 135                 140

Asp Ala His Phe Arg Glu Asp Leu Glu Asn Met Glu Pro Arg Lys Leu
145                 150                 155                 160

Phe Phe Lys Trp Gly Thr His Leu Leu Arg Asp Phe Ser Val Gly Gly
                165                 170                 175

Cys Ile Met Leu Asp Met Arg Tyr His Asn His Met His Lys Thr Val
            180                 185                 190

Gln Gln Val Ser Ala Asp Ala Ala Ala Tyr Ser Gly Leu Ser Leu
        195                 200                 205

Asp Ser Ser Thr Ser Ala Tyr Lys Asn Ala Val Ser Phe Tyr Gln Asn
210                 215                 220

Val Ser Val Arg Ile Arg Ser Val Gly Gly Asn Ser Phe Ser Ala Phe
225                 230                 235                 240

Ser Val Ser Asp Phe Asn Ser Gln Ser Lys Ala Trp Met Asp Ser Leu
                245                 250                 255

Ala Asp Lys Ala Val Pro Phe Arg Ile Asn Arg Asn Gly Ser Leu Pro
            260                 265                 270

Ile Trp Glu Leu Thr Ser Asn Ala Ala Arg Ala Lys Thr Leu Glu Lys
        275                 280                 285

Glu Phe Tyr Leu Tyr Asn Ile Asp Val Leu Asp Glu Val Lys Ala Asn
    290                 295                 300

Ile Pro Phe Ile Thr Asp Leu Arg Val Glu Ile Arg Asp Lys Asp Asn
305                 310                 315                 320

Ile Arg Ser Val Cys Pro Glu Asn Trp Tyr Val Ala Gln Met Asn Pro
                325                 330                 335

Gly Thr Leu Ser Ala Tyr Asp Ile Asp Leu Asn Lys Gly Ser Gly Gly
            340                 345                 350

Lys Tyr Ile Tyr Leu Leu Tyr Arg Phe Gly Thr Asn Gln Lys Asp Arg
        355                 360                 365

Ile Thr Asp Ile Lys Ile Leu Met Gly Arg Asn Thr Thr Leu Gly Gly
    370                 375                 380

Tyr Thr Arg Ile Asp Ala Asp Leu Asn Thr Gly Ser Gly Gly Glu Tyr
385                 390                 395                 400

Ile Tyr Leu Ala Tyr Lys Lys Glu Asp Asn Lys Glu Lys Asp Gly Ile
                405                 410                 415

Tyr Gly Leu Gly Thr Thr Glu Gln Ser Ser Phe Thr Asp Asn Tyr Trp
            420                 425                 430

Arg Met Ala Lys Asp Gln Asn Asn Asn Leu Ala Asp Leu Asn Lys Gly
```

```
                435                 440                 445
Ala Gly Gly Leu Phe Ile Tyr Leu Leu Thr Tyr Arg Glu Lys Tyr Leu
            450                 455                 460
Asp Glu Ile Glu Arg Glu Lys Arg Glu Leu Gln Ala Leu Thr Asp Ser
465                 470                 475                 480
Leu Lys

<210> SEQ ID NO 5
<211> LENGTH: 482
<212> TYPE: PRT
<213> ORGANISM: Artificial Sequence
<220> FEATURE:
<223> OTHER INFORMATION: Lachnospiraceae spp.

<400> SEQUENCE: 5

Met Ser Asn Ile Asp Leu Leu Lys Leu Gln Ser Leu Leu Asp Asp His
1               5                   10                  15
Arg His Tyr Leu Leu Gln Gly Tyr Asn Val Val Ser Asn Pro Tyr Leu
            20                  25                  30
Arg Thr Glu Asp Ile Gln Met Ser Asn Thr Ile Leu Asp Lys Asp Lys
        35                  40                  45
Leu Asn Glu Lys Phe Pro Gly Asn Ser Phe Tyr Asn Tyr Val Ser Gly
    50                  55                  60
Asn Glu Thr Gly Ser Ile Ser Glu Thr Tyr Ala Gly Asn Thr Leu Tyr
65                  70                  75                  80
Glu Met Glu Asn Ser Phe Gly Thr Lys Asn Thr Ile Ala Tyr Asn Ser
                85                  90                  95
Val Ala Leu Asn Ala Ser Leu Ser Ala Asp Tyr Gln Thr Gly Asn Ser
            100                 105                 110
Ile Leu Asp Asn Asn Ile Phe Leu Lys Gln Tyr Gln Ala His Val Leu
        115                 120                 125
Gly His Ile Tyr Ser Arg Gly Asp Val Ser Asp Leu Arg Glu Cys Leu
    130                 135                 140
Asp Ala His Phe Arg Glu Asp Leu Glu Asn Met Glu Pro Arg Lys Leu
145                 150                 155                 160
Phe Phe Lys Trp Gly Thr His Leu Ile Arg Asp Phe Ser Val Gly Gly
                165                 170                 175
Cys Ile Met Leu Asp Met Arg Tyr His Asn His Met His Lys Thr Val
            180                 185                 190
Gln Gln Val Ser Ala Asp Ala Ala Ala Tyr Ser Gly Leu Ser Leu
        195                 200                 205
Asp Ser Ser Thr Ser Ala Tyr Lys Asn Ala Val Ser Phe Tyr Gln Asn
    210                 215                 220
Val Ser Val Arg Ile Arg Ser Val Gly Gly Asn Ser Phe Ser Ala Phe
225                 230                 235                 240
Ser Val Ser Asp Phe Asn Ser Gln Ser Lys Ala Trp Met Asp Ser Leu
                245                 250                 255
Ala Asp Lys Ala Val Pro Phe Arg Ile Asn Arg Asn Gly Ser Leu Pro
            260                 265                 270
Ile Trp Glu Leu Thr Ser Asn Ala Ala Arg Ala Lys Thr Leu Glu Lys
        275                 280                 285
Glu Phe Tyr Leu Tyr Asn Ile Asp Val Leu Asp Glu Val Lys Ala Asn
    290                 295                 300
Ile Pro Phe Ile Thr Asp Leu Arg Val Glu Ile Arg Asp Lys Asp Asn
305                 310                 315                 320
```

```
Ile Arg Ser Val Cys Pro Glu Asn Trp Tyr Val Ala Gln Met Asn Pro
                325                 330                 335

Gly Thr Leu Ser Ala Tyr Asp Ile Asp Leu Asn Lys Gly Ser Gly Gly
            340                 345                 350

Lys Tyr Ile Tyr Leu Leu Tyr Arg Phe Gly Thr Asn Gln Lys Asp Arg
        355                 360                 365

Ile Thr Asp Ile Lys Ile Leu Met Gly Arg Asn Thr Thr Leu Gly Gly
    370                 375                 380

Trp Thr Arg Ile Asp Ala Asp Leu Asn Thr Gly Ser Gly Gly Glu Tyr
385                 390                 395                 400

Ile Tyr Leu Ala Tyr Lys Lys Glu Asp Asn Lys Glu Lys Asp Gly Ile
                405                 410                 415

Tyr Gly Leu Gly Thr Thr Glu Gln Ser Ser Phe Thr Asp Asn Tyr Trp
            420                 425                 430

Arg Met Ala Lys Asp Gln Asn Asn Asn Leu Ala Asp Leu Asn Lys Gly
        435                 440                 445

Ala Gly Gly Leu Phe Ile Tyr Leu Leu Thr Tyr Arg Glu Lys Tyr Leu
    450                 455                 460

Asp Glu Ile Glu Arg Glu Lys Arg Glu Leu Gln Ala Leu Thr Asp Ser
465                 470                 475                 480

Leu Lys

<210> SEQ ID NO 6
<211> LENGTH: 482
<212> TYPE: PRT
<213> ORGANISM: Artificial Sequence
<220> FEATURE:
<223> OTHER INFORMATION: Lachnospiraceae spp.

<400> SEQUENCE: 6

Met Ser Asn Ile Asp Leu Leu Lys Leu Gln Ser Leu Leu Asp His
1               5                   10                  15

Arg His Tyr Leu Leu Gln Gly Tyr Asn Val Val Ser Asn Pro Tyr Leu
                20                  25                  30

Arg Thr Glu Asp Ile Gln Met Ser Asn Thr Ile Leu Asp Lys Asp Lys
            35                  40                  45

Leu Asn Glu Lys Phe Pro Gly Asn Ser Phe Tyr Asn Tyr Val Ser Gly
        50                  55                  60

Asn Glu Thr Gly Ser Ile Ser Glu Thr Tyr Ala Gly Asn Thr Leu Tyr
65                  70                  75                  80

Glu Met Glu Asn Ser Phe Gly Thr Lys Asn Thr Ile Ala Tyr Asn Ser
                85                  90                  95

Val Ala Leu Asn Ala Ser Leu Ser Ala Asp Tyr Gln Thr Gly Asn Ser
            100                 105                 110

Ile Leu Asp Asn Asn Ile Phe Leu Lys Gln Tyr Gln Ala His Val Leu
        115                 120                 125

Gly His Ile Tyr Ser Arg Gly Asp Val Ser Asp Leu Arg Glu Cys Leu
    130                 135                 140

Asp Ala His Phe Arg Glu Asp Leu Glu Asn Met Glu Pro Arg Lys Leu
145                 150                 155                 160

Phe Phe Lys Trp Gly Thr His Leu Ile Arg Asp Phe Ser Val Gly Gly
                165                 170                 175

Cys Ile Met Leu Asp Met Arg Tyr His Asn His Met Lys Thr Val
            180                 185                 190
```

```
Gln Gln Val Ser Ala Asp Ala Ala Ala Tyr Ser Gly Leu Ser Leu
        195                 200                 205

Asp Ser Ser Thr Ser Ala Tyr Lys Asn Ala Val Ser Phe Tyr Gln Asn
210                 215                 220

Val Ser Val Arg Ile Arg Ser Val Gly Gly Asn Ser Phe Ser Ala Phe
225                 230                 235                 240

Ser Val Ser Asp Phe Asn Ser Gln Ser Lys Ala Trp Met Asp Ser Leu
                245                 250                 255

Ala Asp Lys Ala Val Pro Phe Arg Ile Asn Arg Asn Gly Ser Leu Pro
            260                 265                 270

Ile Trp Glu Leu Thr Ser Asn Ala Ala Arg Ala Lys Thr Leu Glu Lys
        275                 280                 285

Glu Phe Tyr Leu Tyr Asn Ile Asp Val Leu Asp Glu Val Lys Ala Asn
    290                 295                 300

Ile Pro Phe Ile Thr Asp Leu Arg Val Glu Ile Arg Asp Lys Asp Asn
305                 310                 315                 320

Ile Arg Ser Val Cys Pro Glu Asn Trp Tyr Val Ala Gln Met Asn Pro
                325                 330                 335

Gly Thr Leu Ser Ala Tyr Asp Ile Asp Leu Asn Lys Gly Ser Gly Gly
            340                 345                 350

Lys Tyr Ile Tyr Leu Leu Tyr Arg Phe Gly Thr Asn Gln Lys Asp Arg
        355                 360                 365

Ile Thr Asp Ile Lys Ile Leu Met Gly Arg Asn Thr Thr Leu Gly Gly
    370                 375                 380

Tyr Thr Arg Ile Asp Ala Asp Leu Asn Thr Gly Ser Gly Gly Glu Trp
385                 390                 395                 400

Ile Tyr Leu Ala Tyr Lys Lys Glu Asp Asn Lys Glu Lys Asp Gly Ile
                405                 410                 415

Tyr Gly Leu Gly Thr Thr Glu Gln Ser Ser Phe Thr Asp Asn Tyr Trp
            420                 425                 430

Arg Met Ala Lys Asp Gln Asn Asn Asn Leu Ala Asp Leu Asn Lys Gly
        435                 440                 445

Ala Gly Gly Leu Phe Ile Tyr Leu Leu Thr Tyr Arg Glu Lys Tyr Leu
    450                 455                 460

Asp Glu Ile Glu Arg Glu Lys Arg Glu Leu Gln Ala Leu Thr Asp Ser
465                 470                 475                 480

Leu Lys

<210> SEQ ID NO 7
<211> LENGTH: 482
<212> TYPE: PRT
<213> ORGANISM: Artificial Sequence
<220> FEATURE:
<223> OTHER INFORMATION: Lachnospiraceae spp.

<400> SEQUENCE: 7

Met Ser Asn Ile Asp Leu Leu Lys Leu Gln Ser Leu Leu Asp Asp His
1               5                   10                  15

Arg His Tyr Leu Leu Gln Gly Tyr Asn Val Val Ser Asn Pro Tyr Leu
            20                  25                  30

Arg Thr Glu Asp Ile Gln Met Ser Asn Thr Ile Leu Asp Lys Asp Lys
        35                  40                  45

Leu Asn Glu Lys Phe Pro Gly Asn Ser Phe Tyr Asn Tyr Val Ser Gly
    50                  55                  60

Asn Glu Thr Gly Ser Ile Ser Glu Thr Tyr Ala Gly Asn Thr Leu Tyr
```

```
            65                  70                  75                  80
        Glu Met Glu Asn Ser Phe Gly Thr Lys Asn Thr Ile Ala Tyr Asn Ser
                        85                  90                  95

Val Ala Leu Asn Ala Ser Leu Ser Ala Asp Tyr Gln Thr Gly Asn Ser
                        100                 105                 110

Ile Leu Asp Asn Asn Ile Phe Leu Lys Gln Tyr Gln Ala His Val Leu
                        115                 120                 125

Gly His Ile Tyr Ser Arg Gly Asp Val Ser Asp Leu Arg Glu Cys Leu
                        130                 135                 140

Asp Ala His Phe Arg Glu Asp Leu Glu Asn Met Glu Pro Arg Lys Leu
        145                 150                 155                 160

Phe Phe Lys Trp Gly Thr His Leu Ile Arg Asp Phe Ser Val Gly Gly
                        165                 170                 175

Cys Ile Met Leu Asp Met Arg Tyr His Asn His Met His Lys Thr Val
                        180                 185                 190

Gln Gln Val Ser Ala Asp Ala Ala Ala Tyr Ser Gly Leu Ser Leu
                        195                 200                 205

Asp Ser Ser Thr Ser Ala Tyr Lys Asn Ala Val Ser Phe Tyr Gln Asn
                        210                 215                 220

Val Ser Val Arg Ile Arg Ser Val Gly Gly Asn Ser Phe Ser Ala Phe
        225                 230                 235                 240

Ser Val Ser Asp Phe Asn Ser Gln Ser Lys Ala Trp Met Asp Ser Leu
                        245                 250                 255

Ala Asp Lys Ala Val Pro Phe Arg Ile Asn Arg Asn Gly Ser Leu Pro
                        260                 265                 270

Ile Trp Glu Leu Thr Ser Asn Ala Ala Arg Ala Lys Thr Leu Glu Lys
                        275                 280                 285

Glu Phe Tyr Leu Tyr Asn Ile Asp Val Leu Asp Glu Val Lys Ala Asn
                        290                 295                 300

Ile Pro Phe Ile Thr Asp Leu Arg Val Glu Ile Arg Asp Lys Asp Asn
        305                 310                 315                 320

Ile Arg Ser Val Cys Pro Glu Asn Trp Tyr Val Ala Gln Met Asn Pro
                        325                 330                 335

Gly Thr Leu Ser Ala Tyr Asp Ile Asp Leu Asn Lys Gly Ser Gly Gly
                        340                 345                 350

Lys Tyr Ile Tyr Leu Leu Tyr Arg Phe Gly Thr Asn Gln Lys Asp Arg
                        355                 360                 365

Ile Thr Asp Ile Lys Ile Leu Met Gly Arg Asn Thr Thr Leu Gly Gly
                        370                 375                 380

Tyr Thr Arg Ile Asp Ala Asp Leu Asn Thr Gly Ser Gly Gly Glu Tyr
        385                 390                 395                 400

Ile Trp Leu Ala Tyr Lys Lys Glu Asp Asn Lys Glu Lys Asp Gly Ile
                        405                 410                 415

Tyr Gly Leu Gly Thr Thr Glu Gln Ser Ser Phe Thr Asp Asn Tyr Trp
                        420                 425                 430

Arg Met Ala Lys Asp Gln Asn Asn Asn Leu Ala Asp Leu Asn Lys Gly
                        435                 440                 445

Ala Gly Gly Leu Phe Ile Tyr Leu Leu Thr Tyr Arg Glu Lys Tyr Leu
                        450                 455                 460

Asp Glu Ile Glu Arg Glu Lys Arg Glu Leu Gln Ala Leu Thr Asp Ser
        465                 470                 475                 480

Leu Lys
```

```
<210> SEQ ID NO 8
<211> LENGTH: 482
<212> TYPE: PRT
<213> ORGANISM: Artificial Sequence
<220> FEATURE:
<223> OTHER INFORMATION: Lachnospiraceae spp.

<400> SEQUENCE: 8

Met Ser Asn Ile Asp Leu Leu Lys Leu Gln Ser Leu Leu Asp Asp His
1               5                   10                  15

Arg His Tyr Leu Leu Gln Gly Tyr Asn Val Val Ser Asn Pro Tyr Leu
            20                  25                  30

Arg Thr Glu Asp Ile Gln Met Ser Asn Thr Ile Leu Asp Lys Asp Lys
        35                  40                  45

Leu Asn Glu Lys Phe Pro Gly Asn Ser Phe Tyr Asn Tyr Val Ser Gly
    50                  55                  60

Asn Glu Thr Gly Ser Ile Ser Glu Thr Tyr Ala Gly Asn Thr Leu Tyr
65                  70                  75                  80

Glu Met Glu Asn Ser Phe Gly Thr Lys Asn Thr Ile Ala Tyr Asn Ser
                85                  90                  95

Val Ala Leu Asn Ala Ser Leu Ser Ala Asp Tyr Gln Thr Gly Asn Ser
            100                 105                 110

Ile Leu Asp Asn Asn Ile Phe Leu Lys Gln Tyr Gln Ala His Val Leu
        115                 120                 125

Gly His Ile Tyr Ser Arg Gly Asp Val Ser Asp Leu Arg Glu Cys Leu
    130                 135                 140

Asp Ala His Phe Arg Glu Asp Leu Glu Asn Met Glu Pro Arg Lys Leu
145                 150                 155                 160

Phe Phe Lys Trp Gly Thr His Leu Ile Arg Asp Phe Ser Val Gly Gly
                165                 170                 175

Cys Ile Met Leu Asp Met Arg Tyr His Asn His Met His Lys Thr Val
            180                 185                 190

Gln Gln Val Ser Ala Asp Ala Ala Ala Tyr Ser Gly Leu Ser Leu
        195                 200                 205

Asp Ser Ser Thr Ser Ala Tyr Lys Asn Ala Val Ser Phe Tyr Gln Asn
    210                 215                 220

Val Ser Val Arg Ile Arg Ser Val Gly Gly Asn Ser Phe Ser Ala Phe
225                 230                 235                 240

Ser Val Ser Asp Phe Asn Ser Gln Ser Lys Ala Trp Met Asp Ser Leu
                245                 250                 255

Ala Asp Lys Ala Val Pro Phe Arg Ile Asn Arg Asn Gly Ser Leu Pro
            260                 265                 270

Ile Trp Glu Leu Thr Ser Asn Ala Ala Arg Ala Lys Thr Leu Glu Lys
        275                 280                 285

Glu Phe Tyr Leu Tyr Asn Ile Asp Val Leu Asp Glu Val Lys Ala Asn
    290                 295                 300

Ile Pro Phe Ile Thr Asp Leu Arg Val Glu Ile Arg Asp Lys Asp Asn
305                 310                 315                 320

Ile Arg Ser Val Cys Pro Glu Asn Trp Tyr Val Ala Gln Met Asn Pro
                325                 330                 335

Gly Thr Leu Ser Ala Tyr Asp Ile Asp Leu Asn Lys Gly Ser Gly Gly
            340                 345                 350

Lys Tyr Ile Tyr Leu Leu Tyr Arg Phe Gly Thr Asn Gln Lys Asp Arg
        355                 360                 365
```

```
Ile Thr Asp Ile Lys Ile Leu Met Gly Arg Asn Thr Thr Leu Gly Gly
    370                 375                 380

Tyr Thr Arg Ile Asp Ala Asp Leu Asn Thr Gly Ser Gly Gly Glu Tyr
385                 390                 395                 400

Ile Tyr Leu Ala Tyr Lys Lys Glu Asp Asn Lys Glu Lys Asp Gly Ile
                405                 410                 415

Tyr Gly Leu Gly Thr Thr Glu Gln Ser Ser Phe Thr Asp Asn Trp Trp
            420                 425                 430

Arg Met Ala Lys Asp Gln Asn Asn Asn Leu Ala Asp Leu Asn Lys Gly
                435                 440                 445

Ala Gly Gly Leu Phe Ile Tyr Leu Leu Thr Tyr Arg Glu Lys Tyr Leu
450                 455                 460

Asp Glu Ile Glu Arg Glu Lys Arg Glu Leu Gln Ala Leu Thr Asp Ser
465                 470                 475                 480

Leu Lys

<210> SEQ ID NO 9
<211> LENGTH: 482
<212> TYPE: PRT
<213> ORGANISM: Artificial Sequence
<220> FEATURE:
<223> OTHER INFORMATION: Lachnospiraceae spp.

<400> SEQUENCE: 9

Met Ser Asn Ile Asp Leu Leu Lys Leu Gln Ser Leu Leu Asp Asp His
1               5                   10                  15

Arg His Tyr Leu Leu Gln Gly Tyr Asn Val Val Ser Asn Pro Tyr Leu
            20                  25                  30

Arg Thr Glu Asp Ile Gln Met Ser Asn Thr Ile Leu Asp Lys Asp Lys
        35                  40                  45

Leu Asn Glu Lys Phe Pro Gly Asn Ser Phe Tyr Asn Tyr Val Ser Gly
    50                  55                  60

Asn Glu Thr Gly Ser Ile Ser Glu Thr Tyr Ala Gly Asn Thr Leu Tyr
65                  70                  75                  80

Glu Met Glu Asn Ser Phe Gly Thr Lys Asn Thr Ile Ala Tyr Asn Ser
                85                  90                  95

Val Ala Leu Asn Ala Ser Leu Ser Ala Asp Tyr Gln Thr Gly Asn Ser
            100                 105                 110

Ile Leu Asp Asn Asn Ile Phe Leu Lys Gln Tyr Gln Ala His Val Leu
        115                 120                 125

Gly His Ile Tyr Ser Arg Gly Asp Val Ser Asp Leu Arg Glu Cys Leu
    130                 135                 140

Asp Ala His Phe Arg Glu Asp Leu Glu Asn Met Glu Pro Arg Lys Leu
145                 150                 155                 160

Phe Phe Lys Phe Gly Thr His Leu Leu Arg Asp Phe Ser Val Gly Gly
                165                 170                 175

Cys Ile Met Leu Asp Met Arg Tyr His Asn His Met His Lys Thr Val
            180                 185                 190

Gln Gln Val Ser Ala Asp Ala Ala Ala Tyr Ser Gly Leu Ser Leu
        195                 200                 205

Asp Ser Ser Thr Ser Ala Tyr Lys Asn Ala Val Ser Phe Tyr Gln Asn
    210                 215                 220

Val Ser Val Arg Ile Arg Ser Val Gly Gly Asn Ser Phe Ser Ala Phe
225                 230                 235                 240

Ser Val Ser Asp Phe Asn Ser Gln Ser Lys Ala Trp Met Asp Ser Leu
```

-continued

```
                245                 250                 255
Ala Asp Lys Ala Val Pro Phe Arg Ile Asn Arg Asn Gly Ser Leu Pro
            260                 265                 270

Ile Trp Glu Leu Thr Ser Asn Ala Ala Arg Ala Lys Thr Leu Glu Lys
        275                 280                 285

Glu Phe Tyr Leu Tyr Asn Ile Asp Val Leu Asp Glu Val Lys Ala Asn
    290                 295                 300

Ile Pro Phe Ile Thr Asp Leu Arg Val Glu Ile Arg Asp Lys Asp Asn
305                 310                 315                 320

Ile Arg Ser Val Cys Pro Glu Asn Trp Tyr Val Ala Gln Met Asn Pro
                325                 330                 335

Gly Thr Leu Ser Ala Tyr Asp Ile Asp Leu Asn Lys Gly Ser Gly Gly
            340                 345                 350

Lys Tyr Ile Tyr Leu Leu Tyr Arg Phe Gly Thr Asn Gln Lys Asp Arg
        355                 360                 365

Ile Thr Asp Ile Lys Ile Leu Met Gly Arg Asn Thr Thr Leu Gly Gly
    370                 375                 380

Tyr Thr Arg Ile Asp Ala Asp Leu Asn Thr Gly Ser Gly Gly Glu Tyr
385                 390                 395                 400

Ile Tyr Leu Ala Tyr Lys Lys Glu Asp Asn Lys Glu Lys Asp Gly Ile
                405                 410                 415

Tyr Gly Leu Gly Thr Thr Glu Gln Ser Ser Phe Thr Asn Tyr Trp
            420                 425                 430

Arg Met Ala Lys Asp Gln Asn Asn Asn Leu Ala Asp Leu Asn Lys Gly
        435                 440                 445

Ala Gly Gly Leu Phe Ile Tyr Leu Leu Thr Tyr Arg Glu Lys Tyr Leu
    450                 455                 460

Asp Glu Ile Glu Arg Glu Lys Arg Glu Leu Gln Ala Leu Thr Asp Ser
465                 470                 475                 480

Leu Lys

<210> SEQ ID NO 10
<211> LENGTH: 482
<212> TYPE: PRT
<213> ORGANISM: Artificial Sequence
<220> FEATURE:
<223> OTHER INFORMATION: Lachnospiraceae spp.

<400> SEQUENCE: 10

Met Ser Asn Ile Asp Leu Leu Lys Leu Gln Ser Leu Leu Asp Asp His
1               5                   10                  15

Arg His Tyr Leu Leu Gln Gly Tyr Asn Val Val Ser Asn Pro Tyr Leu
            20                  25                  30

Arg Thr Glu Asp Ile Gln Met Ser Asn Thr Ile Leu Asp Lys Asp Lys
        35                  40                  45

Leu Asn Glu Lys Phe Pro Gly Asn Ser Phe Tyr Asn Tyr Val Ser Gly
    50                  55                  60

Asn Glu Thr Gly Ser Ile Ser Glu Thr Tyr Ala Gly Asn Thr Leu Tyr
65                  70                  75                  80

Glu Met Glu Asn Ser Phe Gly Thr Lys Asn Thr Ile Ala Tyr Asn Ser
            85                  90                  95

Val Ala Leu Asn Ala Ser Leu Ser Ala Asp Tyr Gln Thr Gly Asn Ser
        100                 105                 110

Ile Leu Asp Asn Asn Ile Phe Leu Lys Gln Tyr Gln Ala His Val Leu
    115                 120                 125
```

Gly His Ile Tyr Ser Arg Gly Asp Val Ser Asp Leu Arg Glu Cys Leu
    130                 135                 140

Asp Ala His Phe Arg Glu Asp Leu Glu Asn Met Glu Pro Arg Lys Leu
145                 150                 155                 160

Phe Phe Lys Phe Gly Ser His Leu Ile Arg Asp Phe Ser Val Gly Gly
                165                 170                 175

Cys Ile Met Leu Asp Met Arg Tyr His Asn His Met His Lys Thr Val
            180                 185                 190

Gln Gln Val Ser Ala Asp Ala Ala Ala Tyr Ser Gly Leu Ser Leu
        195                 200                 205

Asp Ser Ser Thr Ser Ala Tyr Lys Asn Ala Val Ser Phe Tyr Gln Asn
210                 215                 220

Val Ser Val Arg Ile Arg Ser Val Gly Gly Asn Ser Phe Ser Ala Phe
225                 230                 235                 240

Ser Val Ser Asp Phe Asn Ser Gln Ser Lys Ala Trp Met Asp Ser Leu
                245                 250                 255

Ala Asp Lys Ala Val Pro Phe Arg Ile Asn Arg Asn Gly Ser Leu Pro
            260                 265                 270

Ile Trp Glu Leu Thr Ser Asn Ala Ala Arg Ala Lys Thr Leu Glu Lys
        275                 280                 285

Glu Phe Tyr Leu Tyr Asn Ile Asp Val Leu Asp Glu Val Lys Ala Asn
290                 295                 300

Ile Pro Phe Ile Thr Asp Leu Arg Val Glu Ile Arg Asp Lys Asp Asn
305                 310                 315                 320

Ile Arg Ser Val Cys Pro Glu Asn Trp Tyr Val Ala Gln Met Asn Pro
                325                 330                 335

Gly Thr Leu Ser Ala Tyr Asp Ile Asp Leu Asn Lys Gly Ser Gly Gly
            340                 345                 350

Lys Tyr Ile Tyr Leu Leu Tyr Arg Phe Gly Thr Asn Gln Lys Asp Arg
        355                 360                 365

Ile Thr Asp Ile Lys Ile Leu Met Gly Arg Asn Thr Thr Leu Gly Gly
370                 375                 380

Tyr Thr Arg Ile Asp Ala Asp Leu Asn Thr Gly Ser Gly Gly Glu Tyr
385                 390                 395                 400

Ile Tyr Leu Ala Tyr Lys Lys Glu Asp Asn Lys Glu Lys Asp Gly Ile
                405                 410                 415

Tyr Gly Leu Gly Thr Thr Glu Gln Ser Ser Phe Thr Asp Asn Tyr Trp
            420                 425                 430

Arg Met Ala Lys Asp Gln Asn Asn Asn Leu Ala Asp Leu Asn Lys Gly
        435                 440                 445

Ala Gly Gly Leu Phe Ile Tyr Leu Leu Thr Tyr Arg Glu Lys Tyr Leu
450                 455                 460

Asp Glu Ile Glu Arg Glu Lys Arg Glu Leu Gln Ala Leu Thr Asp Ser
465                 470                 475                 480

Leu Lys

<210> SEQ ID NO 11
<211> LENGTH: 13
<212> TYPE: PRT
<213> ORGANISM: Unknown
<220> FEATURE:
<223> OTHER INFORMATION: Lachnospiraceae bacterium.

<400> SEQUENCE: 11

Tyr Gly Thr His Leu Ile Arg Asp Phe Ser Val Gly Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Lachnospiraceae spp.

<400> SEQUENCE: 12

Trp Gly Thr His Leu Ile Arg Asp Phe Ser Val Gly Gly
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Lachnospiraceae spp.

<400> SEQUENCE: 13

Phe Gly Thr His Leu Ile Arg Asp Phe Ser Val Gly Gly
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Lachnospiraceae spp.

<400> SEQUENCE: 14

Tyr Gly Thr His Leu Leu Arg Asp Phe Ser Val Gly Gly
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Lachnospiraceae spp.

<400> SEQUENCE: 15

Trp Gly Thr His Leu Leu Arg Asp Phe Ser Val Gly Gly
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Lachnospiraceae spp.

<400> SEQUENCE: 16

Phe Gly Thr His Leu Leu Arg Asp Phe Ser Val Gly Gly
1               5                   10

<210> SEQ ID NO 17
<211> LENGTH: 1449
<212> TYPE: DNA
<213> ORGANISM: Unknown
<220> FEATURE:
<223> OTHER INFORMATION: Lachnospiraceae bacterium.

<400> SEQUENCE: 17
atgtcaaaca ttgatctttt aaaattacaa tctcttttgg atgaccaccg tcattatctg      60

-continued

```
cttcagggat ataatgtagt cagcaacccc tatctcagaa ccgaggatat ccagatgtcc      120
aataccattc tggataaaga taagcttaat gaaaaattcc cgggcaacag cttttataat      180
tacgtgagtg gaaatgaaac aggttccatt tccgaaacct atgcaggaaa tactctttat      240
gagatggaaa acagctttgg gacgaagaat accattgcct acaattcggt agccctcaat      300
gccagccttt ctgcagatta ccagacagga aactccattc tggacaataa tattttctta      360
aagcaatatc aggcgcatgt ccttggccat atctattcca gaggagatgt ttccgacctg      420
cgcgaatgcc tggatgcaca tttccgggag atctggaaa acatggaacc agaaagtta       480 tttttttaaat atggtaccca cctaatccgt gatttcagtg tgggaggatg tatcatgctg     540
gatatgcgtt atcacaacca tatgcataaa accgtacagc aggtttccgc ggatgccgcc      600
gccgcttatt cgggtctcag cctcgattcc tccaccagcg catacaaaaa cgccgtttct      660
ttttatcaga atgtcagcgt caggatacgt tctgtcggcg gaaattcttt ctcggcgttt      720
tctgtcagcg attttaacag tcagagtaag gcctggatgg attctctggc ggacaaagcc      780
gttcctttcc ggattaacag aaacggcagc ctgcctatat gggaactgac gagtaatgcc      840
gcacgtgcca aaacgctgga aaagaattt tatctatata atatagatgt cctggacgaa       900
gtgaaggcaa atattccttt tataaccgac ctccgtgtag aaataaggga taaagataat      960
atccgttccg tctgccctga aaactggtat gttgcccaga tgaatccggg gactctctct      1020
gcttatgata ttgacctgaa caaggatcg ggaggaaaat atatttaccct gctctatcgt      1080 tttggtacaa atcaaaagga cagaattaca gatattaaaa ttctgatggg acgtaataca      1140 acgtcggcg gctataccag gatagatgcc gatttgaata caggatccgg aggtgaatat      1200
atctatcttg catataaaaa agaagataat aaggaaaaag acgggattta cggcctggga      1260
accactgaac agtcatcctt tacggataat tactggagga tggcaaagga tcagaacaat      1320
aatcttgctg atctgaacaa gggagccgga gggcttttta tttatctgtt aacctatcgt      1380
gagaaatatc ttgatgaaat tgaaagggaa aagagagaac tgcaggcgct gactgacagt      1440
ctgaaataa                                                             1449
```

<210> SEQ ID NO 18
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 18

```
atgtcaaaca ttgacctgct gaagttgcag agccttctgg acgatcaccg tcactacctg      60
ctgcagggct acaatgtggt ctcaaacccg tacctgcgta cggaagacat ccagatgtcg      120
aacacaatcc tggataagga taaacttaac gagaaatttc ccggcaatag cttttacaat      180
tatgttagtg ggaacgaaac cggtagtatt tcggaaacct acgctgggaa caccttatac      240
gaaatggaaa actctttcgg aactaaaaac acaatcgcct acaattctgt tgcgcttaat      300
gcgagccttt ctgcagacta ccagaccggt aacagcatcc tggataataa tatctttctg      360
aaacaatatc aggcgcatgt gttgggtcat atctatagcc gcggtgatgt ttccgacctg      420
cgcgaatgcc tggatgcgca cttccgcgag atctcgaga acatggagcc gcgtaaactg      480 tttttttaaat acggtactca tttaattcgt gatttctccg ttggcggctg catcatgctc      540
gatatgcgct accacaatca catgcacaaa accgtccaac aagtgagcgc ggatgcagcc      600
```

| | |
|---|---|
| gccgcgtact caggcctgag cctggacagc tcgacttctg cctacaaaaa cgcggtctca | 660 |
| ttttatcaga acgtctcggt tcgcatccgc agcgttggcg gcaactcgtt ttcggcattc | 720 |
| tctgtttccg atttcaactc ccagtctaaa gcttggatgg acagcctggc agataaggca | 780 |
| gtgccattcc gtattaaccg taacggctct ctgccgattt gggaactgac cagcaatgcc | 840 |
| gcgcgcgcca aaacgctcga aaagaatttt acctgtata acattgatgt actcgatgaa | 900 |
| gtgaaggcga acattccgtt tatcactgat ctgcgggtcg aaatccgcga taaagacaac | 960 |
| attcggtccg tgtgtcctga aaattggtat gtggcccaga tgaacccggg caccctgtct | 1020 |
| gcgtatgata tcgatctcaa caaaggctct ggcggcaagt acatttatct gttgtaccgc | 1080 |
| ttcggaacca accagaaaga tcggatcacg gacatcaaaa tcctgatggg tcgtaatacg | 1140 |
| actcttggcg gttacacccg catcgacgca gatctcaata ctggttccgg cggtgaatac | 1200 |
| atctacctgg catataaaaa agaagataat aaagaaaaag atggcatcta cgggctgggg | 1260 |
| accaccgaac aatcaagttt taccgacaac tattggcgta tggctaaaga ccagaacaat | 1320 |
| aacctcgccg atttgaacaa aggcgcgggc ggccttttca tttacctcct gacgtatcgg | 1380 |
| gaaaagtacc tcgacgaaat tgaacgtgag aaacgtgaac tccaggcctt aaccgacagt | 1440 |
| cttaaataa | 1449 |

<210> SEQ ID NO 19
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 19

| | |
|---|---|
| atgtcaaaca ttgacctgct gaagttgcag agccttctgg acgatcaccg tcactacctg | 60 |
| ctgcagggct acaatgtggt ctcaaacccg tacctgcgta cggaagacat ccagatgtcg | 120 |
| aacacaatcc tggataagga taaacttaac gagaaatttc ccggcaatag cttttacaat | 180 |
| tatgttagtg ggaacgaaac cggtagtatt tcggaaacct acgctgggaa caccttatac | 240 |
| gaaatggaaa actctttccgg aactaaaaac acaatcgcct acaattctgt tgcgcttaat | 300 |
| gcgagccttt ctgcagacta ccagaccggt aacagcatcc tggataataa tatctttctg | 360 |
| aaacaatatc aggcgcatgt gttgggtcat atctatagcc gcggtgatgt ttccgacctg | 420 |
| cgcgaatgcc tggatgcgca cttccgcgag gatctcgaga acatggagcc gcgtaaactg | 480 |
| ttttttaaat ggggtactca tttaattcgt gatttctccg ttggcggctg catccatgctc | 540 |
| gatatgcgct accacaatca catgcacaaa accgtccaac aagtgagcgc ggatgcagcc | 600 |
| gccgcgtact caggcctgag cctggacagc tcgacttctg cctacaaaaa cgcggtctca | 660 |
| ttttatcaga acgtctcggt tcgcatccgc agcgttggcg gcaactcgtt ttcggcattc | 720 |
| tctgtttccg atttcaactc ccagtctaaa gcttggatgg acagcctggc agataaggca | 780 |
| gtgccattcc gtattaaccg taacggctct ctgccgattt gggaactgac cagcaatgcc | 840 |
| gcgcgcgcca aaacgctcga aaagaatttt acctgtata acattgatgt actcgatgaa | 900 |
| gtgaaggcga acattccgtt tatcactgat ctgcgggtcg aaatccgcga taaagacaac | 960 |
| attcggtccg tgtgtcctga aaattggtat gtggcccaga tgaacccggg caccctgtct | 1020 |
| gcgtatgata tcgatctcaa caaaggctct ggcggcaagt acatttatct gttgtaccgc | 1080 |
| ttcggaacca accagaaaga tcggatcacg gacatcaaaa tcctgatggg tcgtaatacg | 1140 |
| actcttggcg gttacacccg catcgacgca gatctcaata ctggttccgg cggtgaatac | 1200 |

```
atctacctgg catataaaaa agaagataat aaagaaaaag atggcatcta cgggctgggg    1260
accaccgaac aatcaagttt taccgacaac tattggcgta tggctaaaga ccagaacaat    1320
aacctcgccg atttgaacaa aggcgcgggc ggccttttca tttacctcct gacgtatcgg    1380
gaaaagtacc tcgacgaaat tgaacgtgag aaacgtgaac tccaggcctt aaccgacagt    1440
cttaaataa                                                            1449

<210> SEQ ID NO 20
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 20
atgtcaaaca ttgacctgct gaagttgcag agccttctgg acgatcaccg tcactacctg      60
ctgcagggct acaatgtggt ctcaaacccg tacctgcgta cggaagacat ccagatgtcg     120
aacacaatcc tggataagga taaacttaac gagaaatttc ccggcaatag cttttacaat     180
tatgttagtg ggaacgaaac cggtagtatt tcggaaacct acgctgggaa caccttatac     240
gaaatggaaa actctttcgg aactaaaaac acaatcgcct acaattctgt tgcgcttaat     300
gcgagccttt ctgcagacta ccagaccggt aacagcatcc tggataataa tatctttctg     360
aaacaatatc aggcgcatgt gttgggtcat atctatagcc gcggtgatgt ttccgacctg     420
cgcgaatgcc tggatgcgca cttccgcgag gatctcgaga catggagcc gcgtaaactg     480 tttttaaat ttggtactca tttaattcgt gatttctccg ttggcggctg catcatgctc     540
gatatgcgct accacaatca catgcacaaa accgtccaac aagtgagcgc ggatgcagcc     600
gccgcgtact caggcctgag cctggacagc tcgacttctg cctacaaaaa cgcggtctca     660
ttttatcaga acgtctcggt tcgcatccgc agcgttggcg gcaactcgtt ttcggcattc     720
tctgtttccg atttcaactc ccagtctaaa gcttggatgg acagcctggc agataaggca     780
gtgccattcc gtattaaccg taacggctct ctgccgattt gggaactgac cagcaatgcc     840
gcgcgcgcca aaacgctcga aaagaattt tacctgtata acattgatgt actcgatgaa     900
gtgaaggcga acattccgtt tatcactgat ctgcgggtcg aaatccgcga taaagacaac     960
attcggtccg tgtgtcctga aaattggtat gtggcccaga tgaacccggg caccctgtct    1020
gcgtatgata tcgatctcaa caaaggctct ggcggcaagt acattttatct gttgtaccgc    1080 ttcggaacca accagaaaga tcggatcacg gacatcaaaa tcctgatggg tcgtaatacg    1140
actcttggcg gttacacccg catcgacgca gatctcaata ctggttccgg cggtgaatac    1200
atctacctgg catataaaaa agaagataat aaagaaaaag atggcatcta cgggctgggg    1260
accaccgaac aatcaagttt taccgacaac tattggcgta tggctaaaga ccagaacaat    1320
aacctcgccg atttgaacaa aggcgcgggc ggccttttca tttacctcct gacgtatcgg    1380
gaaaagtacc tcgacgaaat tgaacgtgag aaacgtgaac tccaggcctt aaccgacagt    1440
cttaaataa                                                            1449

<210> SEQ ID NO 21
<211> LENGTH: 1449
<212> TYPE: DNA
<213> ORGANISM: Artificial Sequence
<220> FEATURE:
<223> OTHER INFORMATION: Lachnospiraceae spp.
```

<400> SEQUENCE: 21

```
atgtcaaaca ttgacctgct gaagttgcag agccttctgg acgatcaccg tcactacctg      60
ctgcagggct acaatgtggt ctcaaacccg tacctgcgta cggaagacat ccagatgtcg     120
aacacaatcc tggataagga taaacttaac gagaaatttc ccggcaatag cttttacaat     180
tatgttagtg ggaacgaaac cggtagtatt tcggaaacct acgctgggaa caccttatac     240
gaaatggaaa actctttcgg aactaaaaac acaatcgcct acaattctgt tgcgcttaat     300
gcgagccttt ctgcagacta ccagaccggt aacagcatcc tggataataa tatctttctg     360
aaacaatatc aggcgcatgt gttgggtcat atctatagcc gcggtgatgt ttccgacctg     420
cgcgaatgcc tggatgcgca cttccgcgag gatctcgaga acatggagcc gcgtaaactg     480
ttttttaaat ggggtactca tttactgcgt gatttctccg ttggcggctg catcatgctc     540
gatatgcgct accacaatca catgcacaaa accgtccaac aagtgagcgc ggatgcagcc     600
gccgcgtact caggcctgag cctggacagc tcgacttctg cctacaaaaa cgcggtctca     660
tttatcaga acgtctcggt tcgcatccgc agcgttggcg gcaactcgtt ttcggcattc     720
tctgtttccg atttcaactc ccagtctaaa gcttggatgg acagcctggc agataaggca     780
gtgccattcc gtattaaccg taacggctct ctgccgattt gggaactgac cagcaatgcc     840
gcgcgcgcca aaacgctcga aaagaatttt tacctgtata acattgatgt actcgatgaa     900
gtgaaggcga acattccgtt tatcactgat ctgcgggtcg aaatccgcga taaagacaac     960
attcggtccg tgtgtcctga aaattggtat gtggcccaga tgaacccggg cacccctgtct   1020
gcgtatgata tcgatctcaa caaaggctct ggcggcaagt acatttatct gttgtaccgc    1080
ttcggaacca accagaaaga tcggatcacg gacatcaaaa tcctgatggg tcgtaatacg    1140
actcttggcg gttacacccg catcgacgca gatctcaata ctggttccgg cggtgaatac    1200
atctacctgg catataaaaa agaagataat aaagaaaaag atggcatcta cgggctgggg    1260
accaccgaac aatcaagttt taccgacaac tattggcgta tggctaaaga ccagaacaat    1320
aacctcgccg atttgaacaa aggcgcgggc ggccttttca tttacctcct gacgtatcgg    1380
gaaaagtacc tcgacgaaat tgaacgtgag aaacgtgaac tccaggcctt aaccgacagt    1440
cttaaataa                                                            1449
```

<210> SEQ ID NO 22
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 22

```
atgtcaaaca ttgacctgct gaagttgcag agccttctgg acgatcaccg tcactacctg      60
ctgcagggct acaatgtggt ctcaaacccg tacctgcgta cggaagacat ccagatgtcg     120
aacacaatcc tggataagga taaacttaac gagaaatttc ccggcaatag cttttacaat     180
tatgttagtg ggaacgaaac cggtagtatt tcggaaacct acgctgggaa caccttatac     240
gaaatggaaa actctttcgg aactaaaaac acaatcgcct acaattctgt tgcgcttaat     300
gcgagccttt ctgcagacta ccagaccggt aacagcatcc tggataataa tatctttctg     360
aaacaatatc aggcgcatgt gttgggtcat atctatagcc gcggtgatgt ttccgacctg     420
cgcgaatgcc tggatgcgca cttccgcgag gatctcgaga acatggagcc gcgtaaactg     480
ttttttaaat ggggtactca tttaattcgt gatttctccg ttggcggctg catcatgctc     540
```

| | | |
|---|---|---|
| gatatgcgct accacaatca catgcacaaa accgtccaac aagtgagcgc ggatgcagcc | 600 | |
| gccgcgtact caggcctgag cctggacagc tcgacttctg cctacaaaaa cgcggtctca | 660 | |
| ttttatcaga acgtctcggt tcgcatccgc agcgttggcg gcaactcgtt ttcggcattc | 720 | |
| tctgtttccg atttcaactc ccagtctaaa gcttggatgg acagcctggc agataaggca | 780 | |
| gtgccattcc gtattaaccg taacggctct ctgccgattt gggaactgac cagcaatgcc | 840 | |
| gcgcgcgcca aaacgctcga aaagaatttt acctgtata acattgatgt actcgatgaa | 900 | |
| gtgaaggcga acattccgtt tatcactgat ctgcgggtcg aaatccgcga taaagacaac | 960 | |
| attcggtccg tgtgtcctga aaattggtat gtggcccaga tgaacccggg caccctgtct | 1020 | |
| gcgtatgata tcgatctcaa caaaggctct ggcggcaagt acatttatct gttgtaccgc | 1080 | |
| ttcggaacca accagaaaga tcggatcacg gacatcaaaa tcctgatggg tcgtaatacg | 1140 | |
| actcttggcg gttggacccg catcgacgca gatctcaata ctggttccgg cggtgaatac | 1200 | |
| atctacctgg catataaaaa agaagataat aaagaaaaag atggcatcta cgggctgggg | 1260 | |
| accaccgaac aatcaagttt taccgacaac tattggcgta tggctaaaga ccagaacaat | 1320 | |
| aacctcgccg atttgaacaa aggcgcgggc ggccttttca tttacctcct gacgtatcgg | 1380 | |
| gaaaagtacc tcgacgaaat tgaacgtgag aaacgtgaac tccaggcctt aaccgacagt | 1440 | |
| cttaaataa | 1449 | |

<210> SEQ ID NO 23
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 23

| | | |
|---|---|---|
| atgtcaaaca ttgacctgct gaagttgcag agccttctgg acgatcaccg tcactacctg | 60 | |
| ctgcagggct acaatgtggt ctcaaacccg tacctgcgta cggaagacat ccagatgtcg | 120 | |
| aacacaatcc tggataagga taaacttaac gagaaatttc ccggcaatag cttttacaat | 180 | |
| tatgttagtg ggaacgaaac cggtagtatt tcggaaacct acgctgggaa caccttatac | 240 | |
| gaaatggaaa actctttcgg aactaaaaac acaatcgcct acaattctgt tgcgcttaat | 300 | |
| gcgagccttt ctgcagacta ccagaccggt aacagcatcc tggataataa tatctttctg | 360 | |
| aaacaatatc aggcgcatgt gttgggtcat atctatagcc gcggtgatgt ttccgacctg | 420 | |
| cgcgaatgcc tggatgcgca cttccgcgag gatctcgaga catggagcc gcgtaaactg | 480 | |
| ttttttaaat ggggtactca tttaattcgt gatttctccg ttggcggctg catcatgctc | 540 | |
| gatatgcgct accacaatca catgcacaaa accgtccaac aagtgagcgc ggatgcagcc | 600 | |
| gccgcgtact caggcctgag cctggacagc tcgacttctg cctacaaaaa cgcggtctca | 660 | |
| ttttatcaga acgtctcggt tcgcatccgc agcgttggcg gcaactcgtt ttcggcattc | 720 | |
| tctgtttccg atttcaactc ccagtctaaa gcttggatgg acagcctggc agataaggca | 780 | |
| gtgccattcc gtattaaccg taacggctct ctgccgattt gggaactgac cagcaatgcc | 840 | |
| gcgcgcgcca aaacgctcga aaagaatttt acctgtata acattgatgt actcgatgaa | 900 | |
| gtgaaggcga acattccgtt tatcactgat ctgcgggtcg aaatccgcga taaagacaac | 960 | |
| attcggtccg tgtgtcctga aaattggtat gtggcccaga tgaacccggg caccctgtct | 1020 | |
| gcgtatgata tcgatctcaa caaaggctct ggcggcaagt acatttatct gttgtaccgc | 1080 | |

```
ttcggaacca accagaaaga tcggatcacg gacatcaaaa tcctgatggg tcgtaatacg    1140
actcttggcg gttacacccg catcgacgca gatctcaata ctggttccgg cggtgaatgg    1200
atctacctgg catataaaaa agaagataat aaagaaaaag atggcatcta cgggctgggg    1260
accaccgaac aatcaagttt taccgacaac tattggcgta tggctaaaga ccagaacaat    1320
aacctcgccg atttgaacaa aggcgcgggc ggccttttca tttacctcct gacgtatcgg    1380
gaaaagtacc tcgacgaaat tgaacgtgag aaacgtgaac tccaggcctt aaccgacagt    1440
cttaaataa                                                            1449

<210> SEQ ID NO 24
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 24
atgtcaaaca ttgacctgct gaagttgcag agccttctgg acgatcaccg tcactacctg     60
ctgcagggct acaatgtggt ctcaaacccg tacctgcgta cggaagacat ccagatgtcg    120
aacacaatcc tggataagga taaacttaac gagaaatttc ccggcaatag cttttacaat    180
tatgttagtg ggaacgaaac cggtagtatt tcggaaacct acgctgggaa caccttatac    240
gaaatggaaa actctttcgg aactaaaaac acaatcgcct acaattctgt tgcgcttaat    300
gcgagccttt ctgcagacta ccagaccggt aacagcatcc tggataataa tatctttctg    360
aaacaatatc aggcgcatgt gttgggtcat atctatagcc gcggtgatgt ttccgacctg    420
cgcgaatgcc tggatgcgca cttccgcgag gatctcgaga acatggagcc gcgtaaactg    480 tttttttaaat ggggtactca tttaattcgt gatttctccg ttggcggctg catcatgctc    540
gatatgcgct accacaatca catgcacaaa accgtccaac aagtgagcgc ggatgcagcc    600
gccgcgtact caggcctgag cctggacagc tcgacttctg cctacaaaaa cgcggtctca    660
ttttatcaga acgtctcggt tcgcatccgc agcgttggcg gcaactcgtt ttcggcattc    720 tctgttccg atttcaactc ccagtctaaa gcttggatgg acagcctggc agataaggca    780
gtgccattcc gtattaaccg taacggctct ctgccgattt gggaactgac cagcaatgcc    840
gcgcgcgcca aaacgctcga aaagaatttt tacctgtata acattgatgt actcgatgaa    900
gtgaaggcga acattccgtt tatcactgat ctgcgggtcg aaatccgcga taaagacaac    960
attcggtccg tgtgtcctga aaattggtat gtggcccaga tgaacccggg cacccctgtct   1020 gcgtatgata tcgatctcaa caaaggctct ggcggcaagt acatttatct gttgtaccgc    1080
ttcggaacca accagaaaga tcggatcacg gacatcaaaa tcctgatggg tcgtaatacg    1140
actcttggcg gttacacccg catcgacgca gatctcaata ctggttccgg cggtgaatac    1200
atctggctgg catataaaaa agaagataat aaagaaaaag atggcatcta cgggctgggg    1260
accaccgaac aatcaagttt taccgacaac tattggcgta tggctaaaga ccagaacaat    1320
aacctcgccg atttgaacaa aggcgcgggc ggccttttca tttacctcct gacgtatcgg    1380
gaaaagtacc tcgacgaaat tgaacgtgag aaacgtgaac tccaggcctt aaccgacagt    1440
cttaaataa                                                            1449

<210> SEQ ID NO 25
<211> LENGTH: 1449
<212> TYPE: DNA
<213> ORGANISM: Artificial Sequence
```

```
<220> FEATURE:
<223> OTHER INFORMATION: Lachnospiraceae spp.

<400> SEQUENCE: 25
atgtcaaaca ttgacctgct gaagttgcag agccttctgg acgatcaccg tcactacctg      60
ctgcagggct acaatgtggt ctcaaacccg tacctgcgta cggaagacat ccagatgtcg     120
aacacaatcc tggataagga taaacttaac gagaaatttc ccggcaatag cttttacaat     180
tatgttagtg ggaacgaaac cggtagtatt tcggaaacct acgctgggaa caccttatac     240
gaaatggaaa actctttcgg aactaaaaac acaatcgcct acaattctgt tgcgcttaat     300
gcgagccttt ctgcagacta ccagaccggt aacagcatcc tggataataa tatctttctg     360
aaacaatatc aggcgcatgt gttgggtcat atctatagcc gcggtgatgt ttccgacctg     420
cgcgaatgcc tggatgcgca cttccgcgag gatctcgaga acatggagcc gcgtaaactg     480
ttttttaaat ggggtactca tttaattcgt gatttctccg ttggcggctg catcatgctc     540
gatatgcgct accacaatca catgcacaaa accgtccaac aagtgagcgc ggatgcagcc     600
gccgcgtact caggcctgag cctggacagc tcgacttctg cctacaaaaa cgcggtctca     660
ttttatcaga acgtctcggt tcgcatccgc agcgttggcg gcaactcgtt ttcggcattc     720
tctgtttccg atttcaactc ccagtctaaa gcttggatgg acagcctggc agataaggca     780
gtgccattcc gtattaaccg taacggctct ctgccgattt gggaactgac cagcaatgcc     840
gcgcgcgcca aaacgctcga aaagaatttt tacctgtata acattgatgt actcgatgaa     900
gtgaaggcga acattccgtt tatcactgat ctgcgggtcg aaatccgcga taaagacaac     960
attcggtccg tgtgtcctga aaattggtat gtggcccaga tgaacccggg caccctgtct    1020
gcgtatgata tcgatctcaa caaaggctct ggcggcaagt acatttatct gttgtaccgc    1080
ttcggaacca accagaaaga tcggatcacg gacatcaaaa tcctgatggg tcgtaatacg    1140
actcttggcg ttacacccg catcgacgca gatctcaata ctggttccgg cggtgaatac    1200
atctacctgg catataaaaa agaagataat aaagaaaaag atggcatcta cgggctgggg    1260
accaccgaac aatcaagttt taccgacaac tggtggcgta tggctaaaga ccagaacaat    1320
aacctcgccg atttgaacaa aggcgcgggc ggccttttca tttacctcct gacgtatcgg    1380
gaaaagtacc tcgacgaaat tgaacgtgag aaacgtgaac tccaggcctt aaccgacagt    1440
cttaaataa                                                             1449

<210> SEQ ID NO 26
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 26
atgtcaaaca ttgacctgct gaagttgcag agccttctgg acgatcaccg tcactacctg      60
ctgcagggct acaatgtggt ctcaaacccg tacctgcgta cggaagacat ccagatgtcg     120
aacacaatcc tggataagga taaacttaac gagaaatttc ccggcaatag cttttacaat     180
tatgttagtg ggaacgaaac cggtagtatt tcggaaacct acgctgggaa caccttatac     240
gaaatggaaa actctttcgg aactaaaaac acaatcgcct acaattctgt tgcgcttaat     300
gcgagccttt ctgcagacta ccagaccggt aacagcatcc tggataataa tatctttctg     360
aaacaatatc aggcgcatgt gttgggtcat atctatagcc gcggtgatgt ttccgacctg     420
```

```
cgcgaatgcc tggatgcgca cttccgcgag atctcgaga acatggagcc gcgtaaactg    480 tttttaaat  ttggtactca tttacttcgt gatttctccg ttggcggctg catcatgctc    540
gatatgcgct accacaatca catgcacaaa accgtccaac aagtgagcgc ggatgcagcc    600
gccgcgtact caggcctgag cctggacagc tcgacttctg cctacaaaaa cgcggtctca    660
ttttatcaga acgtctcggt tcgcatccgc agcgttggcg gcaactcgtt ttcggcattc    720
tctgtttccg atttcaactc ccagtctaaa gcttggatgg acagcctggc agataaggca    780
gtgccattcc gtattaaccg taacggctct ctgccgattt gggaactgac cagcaatgcc    840
gcgcgcgcca aaacgctcga aaagaatttt tacctgtata acattgatgt actcgatgaa    900
gtgaaggcga acattccgtt tatcactgat ctgcgggtcg aaatccgcga taaagacaac    960
attcggtccg tgtgtcctga aaattggtat gtggcccaga tgaacccggg caccctgtct   1020
gcgtatgata tcgatctcaa caaaggctct ggcggcaagt acatttatct gttgtaccgc   1080
ttcggaacca accagaaaga tcggatcacg gacatcaaaa tcctgatggg tcgtaatacg   1140
actcttggcg gttacacccg catcgacgca gatctcaata ctggttccgg cggtgaatac   1200
atctacctgg catataaaaa agaagataat aaagaaaaag atggcatcta cgggctgggg   1260
accaccgaac aatcaagttt taccgacaac tattggcgta tggctaaaga ccagaacaat   1320
aacctcgccg atttgaacaa aggcgcgggc ggcctttcca tttacctcct gacgtatcgg   1380
gaaaagtacc tcgacgaaat tgaacgtgag aacgtgaac tccaggcctt aaccgacagt   1440
cttaaataa                                                          1449
```

<210> SEQ ID NO 27  
<211> LENGTH: 1449  
<212> TYPE: DNA  
<213> ORGANISM: Artificial Sequence  
<220> FEATURE:  
<223> OTHER INFORMATION: Lachnospiraceae spp.

<400> SEQUENCE: 27

```
atgtcaaaca ttgacctgct gaagttgcag agccttctgg acgatcaccg tcactacctg     60
ctgcagggct acaatgtggt ctcaaacccg tacctgcgta cggaagacat ccagatgtcg    120
aacacaatcc tggataagga taaacttaac gagaaatttc ccggcaatag cttttacaat    180
tatgttagtg ggaacgaaac cggtagtatt tcggaaccct acgctgggaa caccttatac    240
gaaatggaaa actctttcgg aactaaaaac acaatcgcct acaattctgt tgcgcttaat    300
gcgagccttt ctgcagacta ccagaccggt aacagcatcc tggataataa tatcttttctg    360 aaacaatatc aggcgcatgt gttgggtcat atctatagcc gcggtgatgt ttccgacctg    420
cgcgaatgcc tggatgcgca cttccgcgag atctcgaga acatggagcc gcgtaaactg    480 tttttaaat  ttggtagcca tttaattcgt gatttctccg ttggcggctg catcatgctc    540
gatatgcgct accacaatca catgcacaaa accgtccaac aagtgagcgc ggatgcagcc    600
gccgcgtact caggcctgag cctggacagc tcgacttctg cctacaaaaa cgcggtctca    660
ttttatcaga acgtctcggt tcgcatccgc agcgttggcg gcaactcgtt ttcggcattc    720
tctgtttccg atttcaactc ccagtctaaa gcttggatgg acagcctggc agataaggca    780
gtgccattcc gtattaaccg taacggctct ctgccgattt gggaactgac cagcaatgcc    840
gcgcgcgcca aaacgctcga aaagaatttt tacctgtata acattgatgt actcgatgaa    900
gtgaaggcga acattccgtt tatcactgat ctgcgggtcg aaatccgcga taaagacaac    960
attcggtccg tgtgtcctga aaattggtat gtggcccaga tgaacccggg caccctgtct   1020
```

```
gcgtatgata tcgatctcaa caaaggctct ggcggcaagt acatttatct gttgtaccgc    1080
ttcggaacca accagaaaga tcggatcacg gacatcaaaa tcctgatggg tcgtaatacg    1140
actcttggcg gttacacccg catcgacgca gatctcaata ctggttccgg cggtgaatac    1200
atctacctgg catataaaaa agaagataat aaagaaaaag atggcatcta cgggctgggg    1260
accaccgaac aatcaagttt taccgacaac tattggcgta tggctaaaga ccagaacaat    1320
aacctcgccg atttgaacaa aggcgcgggc ggccttttca tttacctcct gacgtatcgg    1380
gaaaagtacc tcgacgaaat tgaacgtgag aaacgtgaac tccaggcctt aaccgacagt    1440
cttaaataa                                                           1449
```

<210> SEQ ID NO 28
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 28

```
atgtctaata ttgacctcct caagctccag tcgctgctcg atgaccatag gcactacctc      60
ctccagggct acaacgtcgt gtctaacccg tacctccgca cagaggacat ccagatgagc     120
aacactattc tcgacaagga taagctgaat gagaagttcc ccggcaattc cttctacaac     180
tacgtgagcg gcaacgagac cgggtcaatc tccgagacat acgccggcaa cactctgtac     240
gagatggaga attctttcgg gaccaagaat acgattgcgt acaacagcgt cgccctcaat     300
gcgagcctgt cggctgacta ccagacgggc aactccatcc tcgataacaa tattttcctg     360
aagcagtacc aggcccatgt tctcggccac atctacagcc gcggggacgt gtcggatctc     420
agggagtgcc tggacgcgca tttcagggag gatctggaga acatggagcc gcggaagctc     480
ttcttcaagt acggcaccca cctgatccgg gacttctcgg tgggcgggtg cattatgctg     540
gatatgcgct accacaacca tatgcacaag accgttcagc aggtgagcgc ggacgcggcc     600
gctgcttact caggcctgtc cctggactcc agcacgtcgg cctacaagaa cgctgtttct     660
ttctaccaga atgtgtctgt ccgcatcagg tcagtcggcg ggaactcttt ctcagccttc     720
tccgttagcg acttcaattc gcagtctaag gcgtggatgg actccctcgc tgataaggcc     780
gtcccgttcc ggatcaatcg caacggctca ctccccattt gggagctgac gagcaacgcc     840
gctagggcta agaccctcga gaaggagttc tacctgtaca acatcgacgt cctcgatgag     900
gttaaggcga atatcccgtt cattacagac ctgagggtcg agatccggga caaggataac     960
attaggtccg tgtgcccaga gaactggtat gtggctcaga tgaatcctgg cactctgagc    1020
gcctacgaca tcgatctcaa caaggggtcg gcgggaagt acatctacct cctgtaccgg     1080
ttcggcacca accagaagga ccgcatcacg gatatcaaga ttctgatggg gaggaacacc    1140 acctcggcg gtacacaag gatcgacgct gatctcaata ctggctccgg cggggagtac    1200
atctacctcg cgtacaagaa ggaggacaac aaggagaagg atggcatcta cggcctcggg    1260
acaactgagc agtcgtcttt cacagacaac tactggagga tggccaagga ccagaacaat    1320
aacctcgccg atctgaataa gggcgctggc ggcctgttca tctacctcct gacgtaccgg    1380
gagaagtacc tggatgagat tgagagggag aagagggagc tgcaggcgct gactgactcg    1440
ctgaagtga                                                           1449
```

<210> SEQ ID NO 29

<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 29

| | |
|---|---|
| atgtctaata ttgacctcct caagctccag tcgctgctcg atgaccatag cactacctc | 60 |
| ctccagggct acaacgtcgt gtctaacccg tacctccgca cagaggacat ccagatgagc | 120 |
| aacactattc tcgacaagga taagctgaat gagaagttcc ccggcaattc cttctacaac | 180 |
| tacgtgagcg gcaacgagac cgggtcaatc tccgagacat acgccggcaa cactctgtac | 240 |
| gagatggaga attctttcgg gaccaagaat acgattgcgt acaacagcgt cgccctcaat | 300 |
| gcgagcctgt cggctgacta ccagacgggc aactccatcc tcgataacaa tattttcctg | 360 |
| aagcagtacc aggcccatgt tctcggccac atctacagcc gcgggacgt gtcggatctc | 420 |
| agggagtgcc tggacgcgca tttcaggag atctggaga acatggagcc gcggaagctc | 480 |
| ttcttcaagt ggggcaccca cctgatccgg acttctcgg tgggcgggtg cattatgctg | 540 |
| gatatgcgct accacaacca tatgcacaag accgttcagc aggtgagcgc ggacgcggcc | 600 |
| gctgcttact caggcctgtc cctggactcc agcacgtcgg cctacaagaa cgctgtttct | 660 |
| ttctaccaga atgtgtctgt ccgcatcagg tcagtcggcg ggaactcttt ctcagccttc | 720 |
| tccgttagcg acttcaattc gcagtctaag gcgtggatgg actccctcgc tgataaggcc | 780 |
| gtcccgttcc ggatcaatcg caacggctca ctccccattt gggagctgac gagcaacgcc | 840 |
| gctagggcta agaccctcga gaaggagttc tacctgtaca catcgacgt cctcgatgag | 900 |
| gttaaggcga atatcccgtt cattacagac ctgagggtcg agatccggga caaggataac | 960 |
| attaggtccg tgtgcccaga gaactggtat gtggctcaga tgaatcctgg cactctgagc | 1020 |
| gcctacgaca tcgatctcaa caaggggtcg ggcgggaagt acatctacct cctgtaccgg | 1080 |
| ttcggcacca accagaagga ccgcatcacg gatatcaaga ttctgatggg gaggaacacc | 1140 |
| accctcggcg ggtacacaag gatcgacgct gatctcaata ctggctccgg cggggagtac | 1200 |
| atctacctcg cgtacaagaa ggaggacaac aaggagaagg atggcatcta cggcctcggg | 1260 |
| acaactgagc agtcgtcttt cacagacaac tactggagga tggccaagga ccagaacaat | 1320 |
| aacctcgccg atctgaataa gggcgctggc ggcctgttca tctacctcct gacgtaccgg | 1380 |
| gagaagtacc tggatgagat tgagagggag aagagggagc tgcaggcgct gactgactcg | 1440 |
| ctgaagtga | 1449 |

<210> SEQ ID NO 30
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 30

| | |
|---|---|
| atgtctaata ttgacctcct caagctccag tcgctgctcg atgaccatag cactacctc | 60 |
| ctccagggct acaacgtcgt gtctaacccg tacctccgca cagaggacat ccagatgagc | 120 |
| aacactattc tcgacaagga taagctgaat gagaagttcc ccggcaattc cttctacaac | 180 |
| tacgtgagcg gcaacgagac cgggtcaatc tccgagacat acgccggcaa cactctgtac | 240 |
| gagatggaga attctttcgg gaccaagaat acgattgcgt acaacagcgt cgccctcaat | 300 |
| gcgagcctgt cggctgacta ccagacgggc aactccatcc tcgataacaa tattttcctg | 360 |

```
aagcagtacc aggcccatgt tctcggccac atctacagcc gcggggacgt gtcggatctc    420
agggagtgcc tggacgcgca tttcagggag gatctggaga acatggagcc gcggaagctc    480
ttcttcaagt tcggcaccca cctgatccgg gacttctcgg tgggcgggtg cattatgctg    540
gatatgcgct accacaacca tatgcacaag accgttcagc aggtgagcgc ggacgcggcc    600
gctgcttact caggcctgtc cctggactcc agcacgtcgg cctacaagaa cgctgtttct    660
ttctaccaga atgtgtctgt ccgcatcagg tcagtcggcg ggaactcttt ctcagccttc    720
tccgttagcg acttcaattc gcagtctaag gcgtggatgg actccctcgc tgataaggcc    780
gtcccgttcc ggatcaatcg caacggctca ctccccattt gggagctgac gagcaacgcc    840
gctagggcta agaccctcga aggagttc tacctgtaca acatcgacgt cctcgatgag    900
gttaaggcga atatcccgtt cattacagac ctgagggtcg agatccggga caaggataac    960
attaggtccg tgtgcccaga gaactggtat gtggctcaga tgaatcctgg cactctgagc    1020
gcctacgaca tcgatctcaa caaggggtcg ggcgggaagt acatctacct cctgtaccgg    1080
ttcggcacca accagaagga ccgcatcacg gatatcaaga ttctgatggg gaggaacacc    1140
accctcggcg ggtacacaag gatcgacgct gatctcaata ctggctccgg cggggagtac    1200
atctacctcg cgtacaagaa ggaggacaac aaggagaagg atggcatcta cggcctcggg    1260
acaactgagc agtcgtcttt cacagacaac tactggagga tggccaagga ccagaacaat    1320
aacctcgccg atctgaataa gggcgctggc ggcctgttca tctacctcct gacgtaccgg    1380
gagaagtacc tggatgagat tgagagggag aagagggagc tgcaggcgct gactgactcg    1440
ctgaagtga                                                             1449

<210> SEQ ID NO 31
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 31
atgtctaata ttgacctcct caagctccag tcgctgctcg atgaccatag gcactacctc     60
ctccagggct acaacgtcgt gtctaacccg tacctccgca cagaggacat ccagatgagc    120
aacactattc tcgacaagga taagctgaat gagaagttcc ccgcaattc cttctacaac    180 tacgtgagcg gcaacgagac cgggtcaatc tccgagacat acgccggcaa cactctgtac    240
gagatggaga attctttcgg gaccaagaat acgattgcgt acaacagcgt cgccctcaat    300
gcgagcctgt cggctgacta ccagacgggc aactccatcc tcgataacaa tattttcctg    360
aagcagtacc aggcccatgt tctcggccac atctacagcc gcggggacgt gtcggatctc    420
agggagtgcc tggacgcgca tttcagggag gatctggaga acatggagcc gcggaagctc    480
ttcttcaagt tcggcaccca cctgctgcgg gacttctcgg tgggcgggtg cattatgctg    540
gatatgcgct accacaacca tatgcacaag accgttcagc aggtgagcgc ggacgcggcc    600
gctgcttact caggcctgtc cctggactcc agcacgtcgg cctacaagaa cgctgtttct    660
ttctaccaga atgtgtctgt ccgcatcagg tcagtcggcg ggaactcttt ctcagccttc    720
tccgttagcg acttcaattc gcagtctaag gcgtggatgg actccctcgc tgataaggcc    780
gtcccgttcc ggatcaatcg caacggctca ctccccattt gggagctgac gagcaacgcc    840
gctagggcta agaccctcga aggagttc tacctgtaca acatcgacgt cctcgatgag    900
```

| | |
|---|---|
| gttaaggcga atatcccgtt cattacagac ctgagggtcg agatccggga caaggataac | 960 |
| attaggtccg tgtgcccaga gaactggtat gtggctcaga tgaatcctgg cactctgagc | 1020 |
| gcctacgaca tcgatctcaa caaggggtcg ggcgggaagt acatctacct cctgtaccgg | 1080 |
| ttcggcacca accagaagga ccgcatcacg gatatcaaga ttctgatggg gaggaacacc | 1140 |
| accctcggcg ggtacacaag gatcgacgct gatctcaata ctggctccgg cggggagtac | 1200 |
| atctacctcg cgtacaagaa ggaggacaac aaggagaagg atggcatcta cggcctcggg | 1260 |
| acaactgagc agtcgtcttt cacagacaac tactggagga tggccaagga ccagaacaat | 1320 |
| aacctcgccg atctgaataa gggcgctggc ggcctgttca tctacctcct gacgtaccgg | 1380 |
| gagaagtacc tggatgagat tgagagggag aagagggagc tgcaggcgct gactgactcg | 1440 |
| ctgaagtga | 1449 |

<210> SEQ ID NO 32
<211> LENGTH: 1449
<212> TYPE: DNA
<213> ORGANISM: Artificial Sequence
<220> FEATURE:
<223> OTHER INFORMATION: Lachnospiracae spp.

<400> SEQUENCE: 32

| | |
|---|---|
| atgtctaata ttgacctcct caagctccag tcgctgctcg atgaccatag gcactacctc | 60 |
| ctccagggct acaacgtcgt gtctaacccg tacctccgca cagaggacat ccagatgagc | 120 |
| aacactattc tcgacaagga taagctgaat gagaagttcc ccggcaattc cttctacaac | 180 |
| tacgtgagcg gcaacgagac cgggtcaatc tccgagacat acgccggcaa cactctgtac | 240 |
| gagatggaga attctttcgg gaccaagaat acgattgcgt acaacagcgt cgccctcaat | 300 |
| gcgagcctgt cggctgacta ccagacgggc aactccatcc tcgataacaa tattttcctg | 360 |
| aagcagtacc aggcccatgt tctcggccac atctacagcc gcggggacgt gtcggatctc | 420 |
| agggagtgcc tggacgcgca tttcagggag gatctggaga acatggagcc gcggaagctc | 480 |
| ttcttcaagt ggggcaccca cctgatccgg gacttctcgg tgggcgggtg cattatgctg | 540 |
| gatatgcgct accacaacca tatgcacaag accgttcagc aggtgagcgc ggacgcggcc | 600 |
| gctgcttact caggcctgtc cctggactcc agcacgtcgg cctacaagaa cgctgtttct | 660 |
| ttctaccaga atgtgtctgt ccgcatcagg tcagtcggcg ggaactcttt ctcagccttc | 720 |
| tccgttagcg acttcaattc gcagtctaag gcgtggatgg actccctcgc tgataaggcc | 780 |
| gtcccgttcc ggatcaatcg caacggctca ctccccattt gggagctgac gagcaacgcc | 840 |
| gctagggcta agaccctcga gaaggagttc tacctgtaca acatcgacgt cctcgatgag | 900 |
| gttaaggcga atatcccgtt cattacagac ctgagggtcg agatccggga caaggataac | 960 |
| attaggtccg tgtgcccaga gaactggtat gtggctcaga tgaatcctgg cactctgagc | 1020 |
| gcctacgaca tcgatctcaa caaggggtcg ggcgggaagt acatctacct cctgtaccgg | 1080 |
| ttcggcacca accagaagga ccgcatcacg gatatcaaga ttctgatggg gaggaacacc | 1140 |
| accctcggcg ggtggacaag gatcgacgct gatctcaata ctggctccgg cggggagtac | 1200 |
| atctacctcg cgtacaagaa ggaggacaac aaggagaagg atggcatcta cggcctcggg | 1260 |
| acaactgagc agtcgtcttt cacagacaac tactggagga tggccaagga ccagaacaat | 1320 |
| aacctcgccg atctgaataa gggcgctggc ggcctgttca tctacctcct gacgtaccgg | 1380 |
| gagaagtacc tggatgagat tgagagggag aagagggagc tgcaggcgct gactgactcg | 1440 |
| ctgaagtga | 1449 |

<210> SEQ ID NO 33
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 33

| | |
|---|---|
| atgtctaata ttgacctcct caagctccag tcgctgctcg atgaccatag gcactacctc | 60 |
| ctccagggct acaacgtcgt gtctaacccg tacctccgca cagaggacat ccagatgagc | 120 |
| aacactattc tcgacaagga taagctgaat gagaagttcc ccggcaattc cttctacaac | 180 |
| tacgtgagcg gcaacgagac cgggtcaatc tccgagacat acgccggcaa cactctgtac | 240 |
| gagatggaga attctttcgg gaccaagaat acgattgcgt acaacagcgt cgccctcaat | 300 |
| gcgagcctgt cggctgacta ccagacgggc aactccatcc tcgataacaa tattttcctg | 360 |
| aagcagtacc aggcccatgt tctcggccac atctacagcc gcgggacgt gtcggatctc | 420 |
| agggagtgcc tggacgcgca tttcagggag gatctggaga acatggagcc gcggaagctc | 480 |
| ttcttcaagt ggggcaccca cctgatccgg gacttctcgg tgggcgggtg cattatgctg | 540 |
| gatatgcgct accacaacca tatgcacaag accgttcagc aggtgagcgc ggacgcggcc | 600 |
| gctgcttact caggcctgtc cctggactcc agcacgtcgg cctacaagaa cgctgtttct | 660 |
| ttctaccaga atgtgtctgt ccgcatcagg tcagtcggcg ggaactcttt ctcagccttc | 720 |
| tccgttagcg acttcaattc gcagtctaag gcgtggatgg actccctcgc tgataaggcc | 780 |
| gtcccgttcc ggatcaatcg caacggctca ctccccattt gggagctgac gagcaacgcc | 840 |
| gctagggcta agaccctcga gaaggagttc tacctgtaca acatcgacgt cctcgatgag | 900 |
| gttaaggcga atatcccgtt cattacagac ctgagggtcg agatccggga caaggataac | 960 |
| attaggtccg tgtgcccaga gaactggtat gtggctcaga tgaatcctgg cactctgagc | 1020 |
| gcctacgaca tcgatctcaa caaggggtcg ggcgggaagt acatctacct cctgtaccgg | 1080 |
| ttcggcacca accagaagga ccgcatcacg gatatcaaga ttctgatggg gaggaacacc | 1140 |
| accctcggcg ggtacacaag gatcgacgct gatctcaata ctggctccgg cggggagtgg | 1200 |
| atctacctcg cgtacaagaa ggaggacaac aaggagaagg atggcatcta cggcctcggg | 1260 |
| acaactgagc agtcgtcttt cacagacaac tactggagga tggccaagga ccagaacaat | 1320 |
| aacctcgccg atctgaataa gggcgctggc ggcctgttca tctacctcct gacgtaccgg | 1380 |
| gagaagtacc tggatgagat tgagagggag aagagggagc tgcaggcgct gactgactcg | 1440 |
| ctgaagtga | 1449 |

<210> SEQ ID NO 34
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 34

| | |
|---|---|
| atgtctaata ttgacctcct caagctccag tcgctgctcg atgaccatag gcactacctc | 60 |
| ctccagggct acaacgtcgt gtctaacccg tacctccgca cagaggacat ccagatgagc | 120 |
| aacactattc tcgacaagga taagctgaat gagaagttcc ccggcaattc cttctacaac | 180 |
| tacgtgagcg gcaacgagac cgggtcaatc tccgagacat acgccggcaa cactctgtac | 240 |

```
gagatggaga attctttcgg gaccaagaat acgattgcgt acaacagcgt cgccctcaat    300
gcgagcctgt cggctgacta ccagacgggc aactccatcc tcgataacaa tattttcctg    360
aagcagtacc aggcccatgt tctcggccac atctacagcc gcgggacgt gtcggatctc    420 agggagtgcc tggacgcgca tttcagggag gatctggaga acatggagcc gcggaagctc    480
ttcttcaagt ggggcaccca cctgatccgg gacttctcgg tgggcgggtg cattatgctg    540
gatatgcgct accacaacca tatgcacaag accgttcagc aggtgagcgc ggacgcggcc    600
gctgcttact caggcctgtc cctggactcc agcacgtcgg cctacaagaa cgctgtttct    660
ttctaccaga atgtgtctgt ccgcatcagg tcagtcggcg ggaactcttt ctcagccttc    720
tccgttagcg acttcaattc gcagtctaag gcgtggatgg actccctcgc tgataaggcc    780
gtcccgttcc ggatcaatcg caacggctca ctccccattt gggagctgac gagcaacgcc    840
gctagggcta agaccctcga aaggagttc tacctgtaca acatcgacgt cctcgatgag    900
gttaaggcga atatcccgtt cattacagac ctgagggtcg agatccggga caaggataac    960
attaggtccg tgtgcccaga gaactggtat gtggctcaga tgaatcctgg cactctgagc    1020
gcctacgaca tcgatctcaa caaggggtcg gcgggaagt acatctacct cctgtaccgg    1080
ttcggcacca accagaagga ccgcatcacg gatatcaaga ttctgatggg gaggaacacc    1140
accctcggcg ggtacacaag gatcgacgct gatctcaata ctggctccgg cggggagtac    1200
atctggctcg cgtacaagaa ggaggacaac aaggagaagg atggcatcta cggcctcggg    1260
acaactgagc agtcgtcttt cacagacaac tactggagga tggccaagga ccagaacaat    1320
aacctcgccg atctgaataa gggcgctggc ggcctgttca tctacctcct gacgtaccgg    1380
gagaagtacc tggatgagat tgagagggag aagagggagc tgcaggcgct gactgactcg    1440
ctgaagtga                                                             1449
```

<210> SEQ ID NO 35
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 35

```
atgtctaata ttgacctcct caagctccag tcgctgctcg atgaccatag gcactacctc     60
ctccagggct acaacgtcgt gtctaacccg tacctccgca cagaggacat ccagatgagc    120
aacactattc tcgacaagga taagctgaat gagaagttcc ccggcaattc cttctacaac    180
tacgtgagcg gcaacgagac cgggtcaatc tccgagacat acgccggcaa cactctgtac    240
gagatggaga attctttcgg gaccaagaat acgattgcgt acaacagcgt cgccctcaat    300
gcgagcctgt cggctgacta ccagacgggc aactccatcc tcgataacaa tattttcctg    360
aagcagtacc aggcccatgt tctcggccac atctacagcc gcgggacgt gtcggatctc    420 agggagtgcc tggacgcgca tttcagggag gatctggaga acatggagcc gcggaagctc    480
ttcttcaagt ggggcaccca cctgatccgg gacttctcgg tgggcgggtg cattatgctg    540
gatatgcgct accacaacca tatgcacaag accgttcagc aggtgagcgc ggacgcggcc    600
gctgcttact caggcctgtc cctggactcc agcacgtcgg cctacaagaa cgctgtttct    660
ttctaccaga atgtgtctgt ccgcatcagg tcagtcggcg ggaactcttt ctcagccttc    720
tccgttagcg acttcaattc gcagtctaag gcgtggatgg actccctcgc tgataaggcc    780
gtcccgttcc ggatcaatcg caacggctca ctccccattt gggagctgac gagcaacgcc    840
```

```
gctagggcta agaccctcga gaaggagttc tacctgtaca acatcgacgt cctcgatgag    900
gttaaggcga atatcccgtt cattacagac ctgagggtcg agatccggga caaggataac    960
attaggtccg tgtgcccaga gaactggtat gtggctcaga tgaatcctgg cactctgagc   1020
gcctacgaca tcgatctcaa caaggggtcg gcgggaagt acatctacct cctgtaccgg   1080
ttcggcacca accagaagga ccgcatcacg gatatcaaga ttctgatggg gaggaacacc   1140
accctcggcg ggtacacaag gatcgacgct gatctcaata ctggctccgg cggggagtac   1200
atctacctcg cgtacaagaa ggaggacaac aaggagaagg atggcatcta cggcctcggg   1260
acaactgagc agtcgtcttt cacagacaac tggtggagga tggccaagga ccagaacaat   1320
aacctcgccg atctgaataa gggcgctggc ggcctgttca tctacctcct gacgtaccgg   1380
gagaagtacc tggatgagat tgagagggag aagagggagc tgcaggcgct gactgactcg   1440
ctgaagtga                                                           1449
```

<210> SEQ ID NO 36
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 36

```
atgtctaata ttgacctcct caagctccag tcgctgctcg atgaccatag gcactacctc     60
ctccagggct acaacgtcgt gtctaacccg tacctccgca cagaggacat ccagatgagc    120
aacactattc tcgacaagga taagctgaat gagaagttcc ccggcaattc cttctacaac    180
tacgtgagcg gcaacgagac cgggtcaatc tccgagacat acgccggcaa cactctgtac    240
gagatggaga attctttcgg gaccaagaat acgattgcgt acaacagcgt cgccctcaat    300
gcgagcctgt cggctgacta ccagacgggc aactccatcc tcgataacaa tattttcctg    360
aagcagtacc aggcccatgt tctcggccac atctacagcc gcggggacgt gtcggatctc    420
agggagtgcc tggacgcgca tttcaggag atctggaga acatggagcc gcggaagctc    480
ttcttcaagt ggggcaccca cctgctgcgg gacttctcgg tgggcgggtg cattatgctg    540
gatatgcgct accacaacca tatgcacaag accgttcagc aggtgagcgc ggacgcggcc    600
gctgcttact caggcctgtc cctggactcc agcacgtcgg cctacaagaa cgctgttttct    660 ttctaccaga atgtgtctgt ccgcatcagg tcagtcggcg ggaactcttt ctcagccttc    720
tccgttagcg acttcaattc gcagtctaag gcgtggatgg actccctcgc tgataaggcc    780
gtcccgttcc ggatcaatcg caacggctca ctccccattt gggagctgac gagcaacgcc    840
gctagggcta agaccctcga gaaggagttc tacctgtaca acatcgacgt cctcgatgag    900
gttaaggcga atatcccgtt cattacagac ctgagggtcg agatccggga caaggataac    960
attaggtccg tgtgcccaga gaactggtat gtggctcaga tgaatcctgg cactctgagc   1020
gcctacgaca tcgatctcaa caaggggtcg gcgggaaat acatctacct cctgtaccgg   1080
ttcggaacca accagaagga ccgcatcacg gacataaaga ttctgatggg gaggaacacc   1140
accctcggcg ggtacacaag gatcgacgct gatctcaata ctggctccgg cggggaatac   1200
atctacctcg cgtacaagaa ggaggacaac aaggagaagg atggcatcta cggcctcggg   1260
acaactgagc agtcgtcttt cacagacaac tactggagga tggccaagga ccagaacaat   1320
aacctcgccg atctgaataa gggcgctggc ggcctgttca tctacctcct gacgtaccgg   1380
```

```
gagaagtacc tggatgagat tgagagggag aagagggagc tgcaggcgct gactgactcg    1440
ctgaagtga                                                            1449

<210> SEQ ID NO 37
<211> LENGTH: 1449
<212> TYPE: DNA
<213> ORGANISM: Artificial Sequence
<220> FEATURE:
<223> OTHER INFORMATION: Lachnospiraceae spp.

<400> SEQUENCE: 37
atgtctaata ttgacctcct caagctccag tcgctgctcg atgaccatag gcactacctc      60
ctccagggct acaacgtcgt gtctaacccg tacctccgca cagaggacat ccagatgagc     120
aacactattc tcgacaagga taagctgaat gagaagttcc ccggcaattc cttctacaac     180
tacgtgagcg gcaacgagac cgggtcaatc tccgagacat acgccggcaa cactctgtac     240
gagatggaga attctttcgg gaccaagaat acgattgcgt acaacagcgt cgccctcaat     300
gcgagcctgt cggctgacta ccagacgggc aactccatcc tcgataacaa tattttcctg     360
aagcagtacc aggcccatgt tctcggccac atctacagcc gcggggacgt gtcggatctc     420
agggagtgcc tggacgcgca tttcaggag gatctggaga acatggagcc gcggaagctc      480
ttcttcaagt ggggcagcca cctgatccgg gacttctcgg tgggcgggtg cattatgctg     540
gatatgcgct accacaacca tatgcacaag accgttcagc aggtgagcgc ggacgcggcc     600
gctgcttact caggcctgtc cctggactcc agcacgtcgg cctacaagaa cgctgtttct     660
ttctaccaga atgtgtctgt ccgcatcagg tcagtcggcg ggaactcttt ctcagccttc     720
tccgttagcg acttcaattc gcagtctaag gcgtggatgg actccctcgc tgataaggcc     780
gtcccgttcc ggatcaatcg caacggctca ctccccattt gggagctgac gagcaacgcc     840
gctagggcta agaccctcga gaaggagttc tacctgtaca acatcgacgt cctcgatgag     900
gttaaggcga atatcccgtt cattacagac ctgagggtcg agatccggga caaggataac     960
attaggtccg tgtgcccaga gaactggtat gtggctcaga tgaatcctgg cactctgagc    1020
gcctacgaca tcgatctcaa caaggggtcg ggcgggaagt acatctacct cctgtaccgg    1080
ttcggcacca accagaagga ccgcatcacg gatatcaaga ttctgatggg gaggaacacc    1140
accctcggcg ggtacacaag gatcgacgct gatctcaata ctggctccgg cggggagtac    1200
atctacctcg cgtacaagaa ggaggacaac aaggagaagg atggcatcta cggcctcggg    1260
acaactgagc agtcgtcttt cacagacaac tactggagga tggccaagga ccagaacaat    1320
aacctcgccg atctgaataa gggcgctggc ggcctgttca tctacctcct gacgtaccgg    1380
gagaagtacc tggatgagat tgagagggag aagagggagc tgcaggcgct gactgactcg    1440
ctgaagtga                                                            1449
```

UNITED STATES PATENT AND TRADEMARK OFFICE
CERTIFICATE OF CORRECTION

PATENT NO. : 11,661,610 B2  
APPLICATION NO. : 17/468905  
DATED : May 30, 2023  
INVENTOR(S) : Clarence Michael Reynolds Page 1 of 1

It is certified that error appears in the above-identified patent and that said Letters Patent is hereby corrected as shown below:

On the Title Page

Item (73) Assignee: "Syngenta Participations SG" should be amended to "Syngenta Participations AG"

In the Claims

Claim 1, Column 97, Line 61, "SECS ID NO: 1" should be amended to "SEQ ID NO: 1"

Signed and Sealed this  
Eighteenth Day of July, 2023

Katherine Kelly Vidal  
*Director of the United States Patent and Trademark Office*